United States Patent
Takahashi et al.

(10) Patent No.: US 7,833,939 B2
(45) Date of Patent: Nov. 16, 2010

(54) HERBICIDE COMPOSITIONS

(75) Inventors: Satoru Takahashi, Tokyo (JP); Ryohei Ueno, Tokyo (JP); Yoshihiro Yamaji, Tokyo (JP); Makoto Fujinami, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 1574 days.

(21) Appl. No.: 10/521,755

(22) PCT Filed: Aug. 7, 2003

(86) PCT No.: PCT/JP03/10073

§ 371 (c)(1),
(2), (4) Date: Jan. 19, 2005

(87) PCT Pub. No.: WO2004/014138

PCT Pub. Date: Feb. 19, 2004

(65) Prior Publication Data

US 2005/0256004 A1    Nov. 17, 2005

(30) Foreign Application Priority Data

Aug. 7, 2002 (JP) .............................. 2002-230028

(51) Int. Cl.
*A01N 43/02* (2006.01)
*A01N 43/10* (2006.01)
(52) U.S. Cl. .................. 504/156; 504/116.1
(58) Field of Classification Search ............ 504/116.1, 504/156
See application file for complete search history.

(56) References Cited

U.S. PATENT DOCUMENTS

| | | | |
|---|---|---|---|
| 6,037,311 | A | 3/2000 | Gosset et al. |
| 6,534,444 | B1 * | 3/2003 | Sievernich et al. ......... 504/128 |
| 7,238,689 | B2 * | 7/2007 | Nakatani et al. ......... 514/227.8 |
| 2003/0130120 | A1 * | 7/2003 | Ziemer et al. ............... 504/105 |

FOREIGN PATENT DOCUMENTS

| | | |
|---|---|---|
| JP | 8-225548 | 9/1996 |
| JP | 9-328483 | 12/1997 |
| JP | 09328483 A * | 12/1997 |
| WO | 92/22204 | 12/1992 |
| WO | 99/65314 | 12/1999 |
| WO | 02/062770 | 8/2002 |
| WO | 03/000686 | 1/2003 |
| WO | 03/010165 | 2/2003 |
| WO | WO 2006024820 A1 * | 3/2006 |

OTHER PUBLICATIONS

U.S. Appl. No. 11/948,542, filed Nov. 30, 2007, Yamaji et al.

* cited by examiner

*Primary Examiner*—Johann R Richter
*Assistant Examiner*—Courtney Brown
(74) *Attorney, Agent, or Firm*—Oblon, Spivak, McClelland, Maier & Neustadt, L.L.P.

(57) ABSTRACT

A herbicidal composition which comprises i) an isoxazoline derivative represented by the following general formula (I) or its salt and ii) at least one compound selected from the Group A:

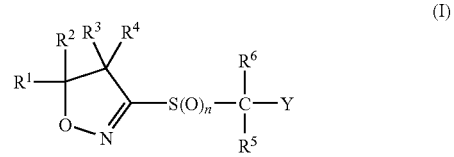

(I)

wherein $R^1$, $R^2$, $R^3$, $R^4$, $R^5$ and $R^6$ are defined in the specification.

28 Claims, No Drawings

HERBICIDE COMPOSITIONS

CROSS REFERENCES TO RELATED APPLICATIONS

This application is a national stage application of International Patent Application No. PCT/JP03/10073, filed on Aug. 7, 2003, and claims priority to Japanese Patent Application No. 2002-230028, filed on Aug. 7, 2002, both of which are incorporated herein by reference in their entities.

TECHNICAL FIELD

The present invention relates to a herbicidal composition.

BACKGROUND ART

As a result of research and development for a long time, various kinds of various agrochemicals have been developed and practically used, and these herbicides have contributed to improvement in productivity of agricultural crops or contributed to elimination or reduction of labor of removing weeds. However even today, it is demanded to develop a new agrochemical having a more satisfactory herbicidal property.

It is demanded to provide a herbicidal agent used for useful crops, which achieves a satisfactory herbicidal effect at a small dose and has an excellent selectivity between aimed crops and weeds by being applied to soil or plant foliage.

DISCLOSURE OF THE INVENTION

An isoxazoline compound of the formula (I) which is one of active ingredients in the herbicidal composition of the present invention is safe to rice, wheat, barley, corn, grain sorghum, soybeans, cotton, sugar beet, turf, fruit trees and the like, and has an excellent herbicidal effect by itself.

The present inventors have discovered that by combining an isoxazoline derivative of the formula (I) with at least one herbicide of Group A at a predetermined ratio, not a simple total herbicidal effect but a synergistic herbicidal effect can be achieved. Thus, by combining at least two agrochemical agents, a herbicidal spectrum is broadened as compared with a herbicidal application range by each agent, and a herbicidal effect is achieved at an earlier stage and is retained for a longer time, and a satisfactory herbicidal effect can be achieved at a smaller dose than a dose by a single use of each agent. Also, the herbicidal composition prepared by combining at least two agrochemical agents is safe to rice, wheat, barley, corn, grain sorghum, soybeans, cotton, sugar beet, turf, fruit trees and the like, and achieves a satisfactory herbicidal effect by one treatment. The present invention has been accomplished on the basis of this discovery.

The present invention is characterized by having the following features.

1. A herbicidal composition which comprises i) an isoxazoline derivative represented by the following general formula (I) or its salt and ii) at least one compound selected from the following Group A:

i) Formula (I)

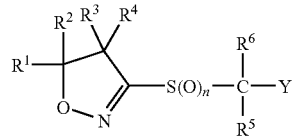

wherein $R^1$ and $R^2$ are respectively independently a hydrogen atom, a C1 to C10 alkyl group, a C3 to C8 cycloalkyl group or a C3 to C8 cycloalkyl C1 to C3 alkyl group; or $R^1$ and $R^2$ may be bonded to each other to form a C3 to C7 spiro ring together with the carbon atoms to which they bond;

$R^3$ and $R^4$ are respectively independently a hydrogen atom, a C1 to C10 alkyl group or a C3 to C8 cycloalkyl group; or $R^3$ and $R^4$ may be bonded to each other to form a C3 to C7 spiro ring together with the carbon atoms to which they bond; or $R^1$, $R^2$, $R^3$ and $R^4$ may form a 5- to 8-membered ring together with the carbon atoms to which they bond;

$R^5$ and $R^6$ are respectively independently a hydrogen atom or a C1 to C10 alkyl group;

Y is a 5- to 6-membered aromatic heterocyclic group or condensed aromatic heterocyclic group having one or more hetero atoms selected from a nitrogen atom, an oxygen atom and a sulfur atom; the heterocyclic group may be substituted with 0 to 6 same or different groups selected from the following substituent group α; when the heterocyclic group is substituted at the two adjacent positions with two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group, all selected from the substituent group α, the two groups may form, together with the atoms to which they bond, a 5- to 8-membered ring which may be substituted with 1 to 4 halogen atoms; the hetero atom of the heterocyclic group, when it is a nitrogen atom, may be oxidized to become N-oxide;

n is an integer of 0 to 2;

(Substituent Group α)

Hydroxyl group; thiol group; halogen atoms; C1 to C10 alkyl groups; C1 to C10 alkyl groups each mono-substituted with a group selected from the following substituent group β, C1 to C4 haloalkyl groups; C3 to C8 cycloalkyl groups; C1 to C10 alkoxy groups; C1 to C10 alkoxy groups each mono-substituted with a group selected from the following substituent group γ; C1 to C4 haloalkoxy groups; C3 to C8 cycloalkyloxy groups; C3 to C8 cycloalkyl C1 to C3 alkyloxy groups; C1 to C10 alkylthio groups; C1 to C10 alkylthio groups each mono-substituted with a group selected from the substituent group γ; C1 to C4 haloalkylthio groups; C2 to C6 alkenyl groups; C2 to C6 alkenyloxy groups; C2 to C6 alkynyl groups; C2 to C6 alkynyloxy groups; C1 to C10 alkylsulfinyl groups; C1 to C10 alkylsulfinyl groups each mono-substituted with a group selected from the substituent group γ; C1 to C10 alkylsulfonyl groups; C1 to C10 alkylsulfonyl groups each mono-substituted with a group selected from the substituent group γ; C1 to C4 haloalkylsulfinyl groups; C1 to C10 alkylsulfonyloxy groups each mono-substituted with a group selected from the substituent group γ; C1 to C4 haloalkylsulfonyl groups; C1 to C10 alkylsulfonyloxy groups; C1 to C4 haloalkylsulfonyloxy groups; optionally substituted phenyl group; optionally substituted phenoxy group; optionally substituted phenylthio group; optionally substituted aromatic heterocyclic groups; optionally substituted aromatic heterocyclic oxy groups; optionally substituted aromatic heterocyclic thio groups; optionally substituted phenylsulfinyl groups; optionally substituted phenylsulfonyl groups; optionally substituted aromatic heterocyclic sulfonyl groups; optionally substituted phenylsulfonyloxy groups; acyl groups; C1 to C4 haloalkylcarbonyl groups; optionally substituted benzylcarbonyl group; optionally substituted benzoyl group; carboxyl group; C1 to C10 alkoxycarbonyl groups; optionally substituted benzyloxycarbonyl group; optionally substituted phenoxycarbonyl group; cyano group; carbamoyl group (its nitrogen atom may be substituted with same or different groups selected from C1 to C10 alkyl groups and optionally substituted phenyl group); C1 to C6 acyloxy groups; C1 to C4 haloalkylcarbonyloxy groups; optionally substituted benzylcarbonyloxy group; optionally substituted benzoyloxy group; nitro group; and amino group (its nitrogen atom may be substituted with same or different groups selected from C1 to C10 alkyl groups, optionally substituted phenyl group, C1 to C6 acyl groups, C1 to C4 haloalkylcarbonyl groups, optionally substituted benzylcarbonyl group, optionally substituted benzoyl group, C1 to C10 alkylsulfonyl group, C1 to C4 haloalkylsulfonyl groups, optionally substituted benzylsulfonyl group, and optionally substituted phenylsulfonyl group);

(Substituent Group β)

Hydroxyl group; C3 to C8 cycloalkyl groups (which may be substituted with halogen atom or alkyl group); C1 to C10 alkoxy groups; C1 to C10 alkylthio groups; C1 to C10 alkylsulfonyl groups; C1 to C10 alkoxycarbonyl groups; C2 to C6 haloalkenyl groups; amino group (its nitrogen atom may be substituted with same or different groups selected from C1 to C10 alkyl groups, C1 to C6 acyl groups; C1 to C4 haloalkylcarbonyl groups, C1 to C10 alkylsulfonyl groups and C1 to C4 haloalkylsulfonyl groups); carbamoyl group (its nitrogen atom may be substituted with same or different C1 to C10 alkyl groups); C1 to C6 acyl groups; C1 to C4 haloalkylcarbonyl groups; C1 to C10 alkoxyimino groups; cyano group; optionally substituted phenyl group; and optionally substituted phenoxy group;

(Substituent Group γ)

C1 to C10 alkoxycarbonyl groups; optionally substituted phenyl group; optionally substituted aromatic heterocyclic groups; cyano group; and carbamoyl group (its nitrogen atom may be substituted with same or different C1 to C10 alkyl groups); and ii) Group A atrazine, simazine, cyanazine, isoxaflutole, mesotrione, flumetsulam, imazethapyr, imazapyr, dicamba, clopyralid, prosulfuron, halosulfuron-methyl, rimsulfuron, bentazone, carfentrazone-ethyl, metribuzin, thifensulfuron-methyl, nicosulfuron, primisulfuron, cloransulam-methyl, glufosinate, glyphosate, glyphosate-trimesium, pendimethalin, linuron, prometryn, diflufenican, flumioxazin, and metolachlor.

2. The herbicidal composition according to Feature 1, wherein the isoxazoline derivative of the formula (I) or its salt has a substituent selected from the substituent group α on the heterocycle which may be substituted with 0 to 6 same or different groups, including hydroxyl group; halogen atoms; C1 to C10 alkyl groups; C1 to C10 alkyl groups each monosubstituted with a group selected from the substituent group β, C1 to C4 haloalkyl groups; C3 to C8 cycloalkyl groups; C1 to C10 alkoxy groups; C1 to C10 alkoxy groups each monosubstituted with a group selected from the substituent group γ; C1 to C4 haloalkoxy groups; C3 to C8 cycloalkyloxy groups; C3 to C8 cycloalkyl C1 to C3 alkyloxy groups; C1 to C10 alkylthio groups; C1 to C10 alkylthio groups each monosubstituted with a group selected from the substituent group γ; C1 to C4 haloalkylthio groups; C2 to C6 alkenyl groups; C2 to C6 alkenyloxy groups; C2 to C6 alkynyl groups; C2 to C6 alkynyloxy groups; C1 to C10 alkylsulfonyl groups; C1 to C4 haloalkylsulfonyl groups; optionally substituted phenyl group; optionally substituted phenoxy group; optionally substituted phenylthio group; optionally substituted aromatic heterocyclic groups; optionally substituted aromatic heterocyclic oxy groups; optionally substituted aromatic heterocyclic thio groups; optionally substituted phenylsulfonyl groups; optionally substituted aromatic heterocyclic sulfonyl groups; C1 to C6 acyl groups; C1 to C4 haloalkylcarbonyl groups; optionally substituted benzylcarbonyl group; optionally substituted benzoyl group; carboxyl group; C1 to C10 alkoxycarbonyl groups; cyano group; carbamoyl group (its nitrogen atom may be substituted with same or different groups selected from C1 to C10 alkyl groups and optionally substituted phenyl group); nitro group; and amino group (its nitrogen atom may be substituted with same or different groups selected from C1 to C10 alkyl groups, optionally substituted phenyl group, C1 to C6 acyl groups, C1 to C4 haloalkylcarbonyl groups, optionally substituted benzylcarbonyl group, optionally substituted benzoyl group, C1 to C10 alkylsulfonyl groups, C1 to C4 haloalkylsulfonyl groups, optionally substituted benzylsulfonyl group, and optionally substituted phenylsulfonyl group); when the heterocyclic group is substituted at the two adjacent positions with two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group, the two groups may form, together with the atoms to which they bond, a 5- to 8-membered ring which may be substituted with 1 to 4 halogen atoms.

3. The herbicidal composition according to Feature 2, wherein the isoxazoline derivative of the formula (I) or its salt has a substituent selected from the substituent group α on the heterocycle which may be substituted with 0 to 6 same or different groups, including halogen atoms; C1 to C10 alkyl groups; C1 to C4 haloalkyl groups; C1 to C10 alkoxy C1 to C3 alkyl groups; C3 to C8 cycloalkyl groups (which may be substituted with halogen atom or alkyl group); C1 to C10 alkoxy groups; C1 to C4 haloalkoxy groups; C3 to C8 cycloalkyl C1 to C3 alkyloxy groups; optionally substituted phenoxy group; C1 to C10 alkylthio groups; C1 to C10 alkylsulfonyl groups; acyl groups; C1 to C4 haloalkylcarbonyl groups; C1 to C10 alkoxycarbonyl groups; cyano group and carbamoyl group (its nitrogen atom may be substituted with same or different C1 to C10 alkyl groups).

4. The herbicidal composition according to any of Feature 1, 2 or 3, wherein $R^1$ and $R^2$ may be the same or different and are each a methyl group or an ethyl group; and $R^3$, $R^4$, $R^5$ and $R^6$ are each a hydrogen atom.

5. The herbicidal composition according to any of Feature 1, 2, 3 or 4, wherein Y is a 5- or 6-membered aromatic heterocyclic group having a hetero atom selected from a nitrogen atom, an oxygen atom and a sulfur atom.

6. The herbicidal composition according to Feature 5, wherein Y is a thienyl group, a pyrazolyl group, an isoxazolyl group, an isothiazolyl group, a pyridyl group or a pyrimidinyl group.

7. The herbicidal composition according to Feature 6, wherein Y is a thiophen-3-yl group, a pyrazol-4-yl group, a pyrazol-5-yl group, an isoxazol-4-yl group, an isothiazol-4-yl group, a pyridyn-3-yl group or a pyrimidin-5-yl group.

8. The herbicidal composition according to Feature 7, wherein Y is a thiophen-3-yl group and the thiophene ring is substituted with the substituent group α at the 2- and 4-positions.

9. The herbicidal composition according to Feature 7, wherein Y is a pyrazol-4-yl group and the pyrazole ring is substituted at the 3- and 5-positions with the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (its nitrogen atom may be substituted with same or different groups selected from C1 to C10 alkyl groups and optionally substituted phenyl group), or an amino group (its nitrogen atom may be substituted with same or different groups selected from C1 to C10 alkyl groups, an optionally substituted phenyl group, acyl groups, C1 to C4 haloalkylcarbonyl groups, an optionally substituted benzylcarbonyl group, an optionally substituted benzoyl group, C1 to C10 alkylsulfonyl groups, C1 to C4 haloalkylsulfonyl groups, an optionally substituted benzylsulfonyl group and an optionally substituted phenylsulfonyl group).

10. The herbicidal composition according to Feature 7, wherein Y is a pyrazol-5-yl group and the pyrazole ring is substituted at the 4-position with the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (its nitrogen atom may be substituted with same or different groups selected from C1 to C10 alkyl groups and an optionally substituted phenyl group), or an amino group (its nitrogen atom may be substituted with same or different groups selected from C1 to C10 alkyl groups, an optionally substituted phenyl group, acyl groups, C1 to C4 haloalkylcarbonyl groups, an optionally substituted benzylcarbonyl group, an optionally substituted benzoyl group, C1 to C10 alkylsulfonyl groups, C1 to C4 haloalkylsulfonyl groups, an optionally substituted benzylsulfonyl group and an optionally substituted phenylsulfonyl group).

11. The herbicidal composition according to Feature 7, wherein Y is an isoxazol-4-yl group and the isoxazole ring is substituted with the substituent group α at the 3- and 5-positions.

12. The herbicidal composition according to Feature 7, wherein Y is an isothiazol-4-yl group and the isothiazole ring is substituted with the substituent group α at the 3- and 5-positions.

13. The herbicidal composition according to Feature 7, wherein Y is a pyridin-3-yl group and the pyridine ring is substituted with the substituent group α at the 2- and 4-positions.

14. The herbicidal composition according to Feature 7, wherein Y is a pyrimidin-5-yl group and the pyrimidine ring is substituted with the substituent group α at the 4- and 6-positions.

15. The herbicidal composition according to any of Features 1 to 14, wherein n is an integer of 2.

16. The herbicidal composition according to any of Features 1 to 14, wherein the compound of Group A is at least one compound selected from the group consisting of atrazine, cyanazine, simazine and prometryn.

17. The herbicidal composition according to any of Features 1 to 14, wherein the compound of Group A is at least one compound selected from the group consisting of glyphosate, glufosinate, linuron and flumetsulam.

18. A herbicidal composition which comprises i) the isoxazoline derivative or its salt is a compound as defined in Feature 9 and ii) the compound of Group A is at least one compound selected from the group consisting of atrazine, cyanazine, simazine, prometryn, glyphosate, glufosinate, linuron, flumetsulam, metribuzin, isoxaflutole, mesotrione, diflufenican, pendimethalin and flumioxazin.

19. A herbicidal composition which comprises i) the isoxazoline derivative or its salt is a compound as defined in Feature 9 and ii) the compound of Group A is at least one compound selected from the group consisting of atrazine, cyanazine, simazine and prometryn.

20. A herbicidal composition which comprises i) the isoxazoline derivative or its salt is a compound as defined in Feature 9 and ii) the compound of Group A is at least one compound selected from the group consisting of glyphosate, glufosinate, linuron and flumetsulam.

21. The herbicidal composition according to any of Features 1 to 20, wherein ii) at least one compound of Group A is contained in an amount of from 0.001 to 100 parts by weight to 1 part by weight of i) an isoxazoline derivative represented by the Formula (I) or its salt.

22. The herbicidal composition according to any of Features 1 to 21, which is used as an agrochemical product containing i) an isoxazoline derivative of the Formula (I) or its salt and ii) at least one compound of Group A in a total amount of from 0.5 to 90 wt %.

The definitions of the terms used in the present specification are given below.

The expression of "C1 to C10", etc. indicates that the substituent appearing after the expression has 1 to 10 carbon atoms in the case of "C1 to C10".

Halogen atom refers to a fluorine atom, a chlorine atom, a bromine atom or an iodine atom.

C1 to C10 alkyl group refers to a straight or branched chain alkyl group of 1 to 10 carbon atoms unless other wise specified; and there can be mentioned, for example, methyl group, ethyl group, n-propyl group, isopropyl group, n-butyl group, isobutyl group, sec-butyl group, tert-butyl group, n-pentyl group, isopentyl group, neopentyl group, n-hexyl group, isohexyl group, 3,3-dimethylbutyl group, heptyl group and octyl group.

C3 to C8 cycloalkyl group refers to a cycloalkyl group of 3 to 8 carbon atoms; and there can be mentioned, for example, cyclopropyl group, cyclobutyl group, cyclopentyl group and cyclohexyl group.

C3 to C8 cycloalkyl C1 to C3 alkyl group (which may be substituted with halogen atom or alkyl group) refers, unless otherwise specified, to a C1 to C3 alkyl group substituted with a C3 to C8 cycloalkyl group which may be substituted with 1 to 4 same or different halogen atoms or C1 to C3 alkyl group; and there can be mentioned, for example, cyclopropylmethyl group, 1-cyclopropylethyl group, 2-cyclopropylethyl group, 1-cyclopropylpropyl group, 2-cyclopropylpropyl group, 3-cyclopropylpropyl group, cyclobutylmethyl group, cyclopentylmethyl group, cyclohexylmethyl group, 2-chlorocyclopropylmethyl group, 2,2-dichlorocyclopropylmethyl group, 2-fluorocyclopropylmethyl group, 2,2-difluorocyclopropylmethyl group, 2-methylcyclopropylmethyl group, 2,2-dimethylcyclopropylmethyl group and 2-methylcyclopropylethyl group.

C3 to C8 cycloalkyl C1 to C3 alkyl group refers to a alkyl group of 1 to 3 carbon atoms, substituted with a cycloalkyl group of 3 to 8 carbon atoms; and there can be mentioned, for example, cyclopropylmethyl group, 1-cyclopropylethyl group, 2-cyclopropylethyl group, 1-cyclopropylpropyl group, 2-cyclopropylpropyl group, 3-cyclopropylpropyl group, cyclobutylmethyl group, cyclopentylmethyl group and cyclohexylmethyl group.

C1 to C4 haloalkyl group refers, unless otherwise specified, to a straight or branched chain alkyl group of 1 to 4 carbon atoms, substituted with 1 to 9 same or different halogen atoms; and there can be mentioned, for example, fluoromethyl group, chloromethyl group, bromomethyl group, difluoromethyl group, trifluoromethyl group, 2,2-difluoroethyl group, 2,2,2-trifluoroethyl group and pentafluoroethyl group.

C2 to C6 alkenyl group refers to a straight or branched chain alkenyl group of 2 to 6 carbon atoms; and there can be mentioned, for example, ethenyl group, 1-propenyl group, 2-propenyl group, isopropenyl group, 1-butenyl group, 2-butenyl group, 3-butenyl group and 2-pentenyl group.

C2 to C6 alkynyl group refers to a straight or branched chain alkynyl group of 2 to 6 carbon atoms; and there can be mentioned, for example, ethynyl group, 2-propynyl group, 1-methyl-2-propynyl group, 2-butynyl group, 3-butynyl group and 2-methyl-3-butynyl group.

C2 to C6 haloalkenyl group refers, unless otherwise specified, to a straight or branched alkenyl group of 2 to 6 carbon atoms, substituted with 1 to 4 same or different halogen atoms; and there can be mentioned, for example, 3-chloro-2-propenyl group and 2-chloro-2-propenyl group.

C1 to C10 alkoxy group refers to an (alkyl)-O— group wherein the alkyl moiety has the above definition; and there can be mentioned, for example, methoxy group, ethoxy group, n-propoxy group, isopropoxy group, tert-butoxy group, n-butoxy group, sec-butoxy group and isobutoxy group.

C1 to C4 haloalkoxy group refers to a (haloalkyl)-O— group wherein the haloalkyl moiety has the above definition; and there can be mentioned, for example, difluoromethoxy group, trifluoromethoxy group, 2,2-difluoroethoxy group and 2,2,2-trifluoroethoxy group.

C3 to C8 cycloalkyloxy group refers to a (cycloalkyl)-O— group wherein the cycloalkyl moiety has the above definition; and there can be mentioned, for example, cyclopropyloxy group, cyclobutyloxy group, cyclopentyloxy group and cyclohexyloxy group.

C3 to C8 cycloalkyl C1 to C3 alkyloxy group refers to a (cycloalkylalkyl)-O— group wherein the cycloalkylalkyl moiety has the above definition; and there can be mentioned, for example, cyclopropylmethoxy group, 1-cyclopropylethoxy group, 2-cyclopropylethoxy group, 1-cyclopropylpropoxy group, 2-cyclopropylpropoxy group, 3-cyclopropylpropoxy group, cyclobutylmethoxy group, cyclopentylmethoxy group and cyclohexylmethoxy group.

C2 to C6 alkenyloxy group and C2 to C6 alkynyloxy group refer, respectively, to an (alkenyl)-O— group and an (alkynyl)-O— group, in each of which the alkenyl or alkynyl moiety has the above definition; and there can be mentioned, for example, 2-propenyloxy group and 2-propynyloxy group.

C1 to C10 alkoxyimino group refers to an (alkoxy)-N═ group wherein the alkoxy moiety has the above definition; and there can be mentioned, for example, methoxyimino group and ethoxyimino group.

C1 to C10 alkylthio group, C1 to C10 alkylsulfinyl group and C1 to C10 alkylsulfonyl group refer, respectively, to an (alkyl)-S— group, an (alkyl)-SO— group and an (alkyl)-SO$_2$— group, in each of which the alkyl moiety has the above definition; and there can be mentioned, for example, methylthio group, ethylthio group, n-propylthio group, isopropylthio group, methylsulfinyl group, methylsulfonyl group, ethylsulfonyl group, n-propylsulfonyl group and isopropylsulfonyl group.

C1 to C10 alkylsulfonyloxy group refers to an (alkylsulfonyl)-O— group wherein the alkylsulfonyl moiety has the above definition, and there can be mentioned, for example, methylsulfonyloxy group and ethylsulfonyloxy group.

C1 to C10 alkoxycarbonyl group refers to an (alkoxy)-CO— group wherein the alkoxy moiety has the above definition, and there can be mentioned, for example, methoxycarbonyl group, ethoxycarbonyl group, n-propoxycarbonyl group and isopropoxycarbonyl group.

C1 to C6 acryl group refers to a straight or branched chain aliphatic acyl group of 1 to 6 carbon atoms, and there can be mentioned, for example, formyl group, acetyl group, propionyl group, isopropionyl group, butyryl group and pivaloyl group.

C1 to C10 acyloxy group refers to an (acyl)-O— group wherein the acyl moiety has the above definition; and there can be mentioned, for example, acetoxy group, propionyloxy group, ispropionyloxy group and pivaloyloxy group.

C1 to C4 haloalkylcarbonyl group, C1 to C4 haloalkylthio group and C1 to C4 haloalkylsulfonyl group refers, respectively, to a (haloalkyl)-CO— group, a (haloalkyl)-S— group and a (haloalkyl)-SO$_2$— group, in each of which the haloalkyl moiety has the above definition; and there can be mentioned, for example, chloroacetyl group, trifluoroacetyl group, pentafluoropropyl group, difluoromethylthio group, trifluoromethylthio group, chloromethylsulfonyl group, difluoromethylsulfonyl group and trifluoromethylsulfonyl group.

C1 to C4 haloalkylcarbonyloxy group and C1 to C4 haloalkylsulfonyloxy group refer, respectively, to a (haloalkylcarbonyl)-O— group and a (haloalkylsulfonyl)-O— group, in each of which the haloalkylcarbonyl moiety or the haloalkylsulfonyl moiety has the above definition; and there can be mentioned, for example, chloroacetyloxy group, trifluoroacetyloxy group, chloromethylsulfonyloxy group and trifluoromethylsulfonyloxy group.

"Optionally substituted" in (optionally substituted) phenyl group, (optionally substituted) aromatic heterocyclic group, (optionally substituted) phenoxy group, (optionally substituted aromatic heterocyclic oxy group, (optionally substituted) phenylthio group, (optionally substituted) aromatic heterocyclic thio group, (optionally substituted) phenylsulfonyl group, (optionally substituted) phenylsulfonyloxy group, (optionally substituted) aromatic heterocyclic sulfonyl group, (optionally substituted) benzylcarbonyl group, (optionally substituted) benzylcarbonyloxy group, (optionally substituted) benzylsulfonyl group, (optionally substituted) benzoyl group, (optionally substituted) benzoyloxy group, (optionally substituted) benzyloxycarbonyl group and (optionally substituted) phenoxycarbonyl group, refers to being optionally substituted with, for example, halogen atom, C1 to C10 alkyl group, C1 to C4 haloalkyl group, C1 to C10 alkoxyalkyl group, C1 to C10 alkoxy group, C1 to C10 alkylthio group, C1 to C10 alkylsulfonyl group, acyl group, C1 to C10 alkoxycarbonyl group, cyano group, carbamoyl group (its nitrogen atom may be substituted with same or different C1 to C10 alkyl groups), nitro group or amino group (its nitrogen atom may be substituted with same or different groups selected from C1 to C10 alkyl groups, C1 to C6 acyl groups, C1 to C4 haloalkylcarbonyl groups, C1 to C10 alkylsulfonyl groups and C1 to C4 haloalkylsulfonyl groups).

5- to 6-membered aromatic heterocyclic group having a hetero atom selected from a nitrogen atom, an oxygen atom and a sulfur atom includes, for example, furyl group, thienyl group, pyrrolyl group, pyrazolyl group, isoxazolyl group, isothiazolyl group, oxazolyl group, thiazolyl group, imidazolyl group, pyridyl group, pyridazinyl group, pyrimidinyl group, pyrazinyl group, triazinyl group, triazolyl group, oxadiazolyl group and thiadiazolyl group, each having 1 to 3 hetero atoms.

Fused aromatic heterocyclic group refers to a group having 1 to 3 hetero atoms randomly selected from nitrogen atom, oxygen atom and sulfur atom; and there can be mentioned, for example, benzofuryl group, benzothienyl group, indolyl group, benzoxazolyl group, benzothiazolyl group, benzimidazolyl group, benzisoxazolyl group, benzisothiazolyl group, indazolyl group, quinolyl group, isoquinolyl group, phthalazinyl group, quinoxalinyl group, quinazolinyl group, cinnolinyl group and benzotriazolyl group.

Aromatic heterocycle in (optionally substituted) aromatic heterocyclic group, (optionally substituted) aromatic heterocyclic oxy group, (optionally substituted) aromatic heterocyclic thio group and (optionally substituted) aromatic heterocyclic sulfonyl group, refers to a 5- to 6-membered group having 1 to 3 hetero atoms randomly selected from nitrogen atom, oxygen atom and sulfur atom; and there can be mentioned, for example, furyl group, thienyl group, pyrrolyl group, pyrazolyl group, isoxazolyl group, isothiazolyl group, oxazolyl group, thiazolyl group, imidazolyl group, pyridyl group, pyridazinyl group, pyrimidinyl group, pyrazinyl group, triazinyl group, triazolyl group, oxadiazolyl group and thiadiazolyl group.

Pharmaceutically acceptable salt is a salt of a compound of the general formula [I] having, in the structure, hydroxyl group, carboxyl group, amino group or the like, with a metal or an organic base or with a mineral acid or an organic acid. As the metal, there can be mentioned alkali metals such as sodium, potassium and the like; and alkaline earth metals such as magnesium, calcium and the like. As the organic base, there can be mentioned triethylamine, diisopropylamine, etc. As the mineral acids, there can be mentioned hydrochloric acid, sulfuric acid, etc. As the organic acid, there can be mentioned acetic acid, methanesulfonic acid, p-toluenesulfonic acid, etc.

In the above-mentioned general formula [I], it is preferred that $R^1$ and $R^2$ may be the same or different and are each a methyl group or an ethyl group;

$R^3$, $R^4$, $R^5$ and $R^6$ are each a hydrogen atom;

n is an integer of 2; and

Y is a thiophen-3-yl group [the 2- and 4-positions of the group are substituted with same or different groups selected from halogen atoms, alkyl groups, haloalkyl groups, alkoxyalkyl groups, cycloalkyl groups, alkoxy groups, haloalkoxy groups, acyl groups, haloalkylcarbonyl groups, alkoxycarbonyl groups, cyano group and carbamoyl group (its nitrogen atom may be substituted with same or different alkyl groups)], or a pyrazol-4-yl group [the 3- and 5-positions of the group are substituted with same or different groups selected from halogen atoms, alkyl groups, haloalkyl groups, alkoxyalkyl groups, cycloalkyl groups, alkoxy groups, haloalkoxy groups, cycloalkylalkyloxy groups, optionally substituted phenoxy group, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups); the 1-position is substituted with hydrogen atom, alkyl group, alkyl group mono-substituted with a group selected from the substituent group β, haloalkyl group, cycloalkyl group, alkenyl group, alkynyl group, alkylsulfonyl group, alkylsulfonyl group mono-substituted with a group selected from the substituent group γ, haloalkylsulfonyl group, optionally substituted phenyl group, optionally substituted aromatic heterocyclic group, optionally substituted phenylsulfonyl group, optionally substituted aromatic heterocyclicsulfonyl group, acyl group, haloalkylcarbonyl group, optionally substituted benzylcarbonyl group, optionally substituted benzoyl group, alkoxycarbonyl group, optionally substituted benzyloxycarbonyl group, optionally substituted phenoxycarbonyl group or carbamoyl group (its nitrogen atom may be substituted with same or different groups selected from alkyl groups and optionally substituted phenyl group)], or a pyrazol-5-yl group [the 4-position of the group is substituted with halogen atom, alkyl group, haloalkyl group, alkoxyalkyl group, haloalkoxy group, acyl group, haloalkylcarbonyl group, alkoxycarbonyl group, cyano group or carbamoyl group (its nitrogen atom may be substituted with same or different alkyl groups); the 1-position is substituted with hydrogen atom, alkyl group, alkyl group mono-substituted with a group selected from the substituent group β, haloalkyl group, cycloalkyl group, or optionally substituted phenyl group], or an isoxazol-4-yl group [the 3- and 5-positions of the group are substituted with same or different groups selected from halogen atoms, alkyl groups, haloalkyl groups, alkoxyalkyl groups, cycloalkyl groups, alkoxy groups, haloalkoxy groups, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups)], or an isothiazol-4-yl group [the 3- and 5-positions of the group are substituted with same or different groups selected from halogen atoms, alkyl groups, haloalkyl groups, alkoxyalkyl groups, cycloalkyl groups, alkoxy groups, haloalkoxy groups, optionally substituted phenoxy group, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups)], or a pyridin-3-yl group [the 2- and 4-positions of the group are substituted with same or different groups selected from halogen atoms, alkyl groups, haloalkyl groups, alkoxyalkyl groups, cycloalkyl groups, alkoxy groups, haloalkoxy groups, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups)], or a pyrimidin-5-yl group [the 4- and 6-positions of the group are substituted with same or different groups selected from halogen atoms, alkyl groups, haloalkyl groups, alkoxyalkyl groups, cycloalkyl groups, alkoxy groups, haloalkoxy groups, alkylthio groups, alkylsulfonyl groups, acyl groups, haloalkylcarbonyl groups, alkoxycarbonyl groups, cyano group and carbamoyl group (its nitrogen atom may be substituted with same or different alkyl groups)].

BEST MODE FOR CARRYING OUT THE INVENTION

Although it depends on relative activities of respective ingredients, the composition of the present invention contains at least one compound of the formula (I) generally in an amount of from 0.001 to 100 parts by weight, preferably from 0.01 to 50 parts by weight, more preferably from 0.05 to 30 parts by weight to 1 part by weight of an isoxazoline derivative of the formula (I) or its salt.

One active ingredient in the composition of the present invention is a compound of the formula (I), and achieves an excellent herbicidal effect by itself.

Particularly, it does not have a substantial phytotoxicity to rice, wheat, barley, corn, grain sorghum, soybeans, cotton, sugar beet, turf, fruit trees and the like, but achieves an excellent herbicidal effect at a small dose to various weeds growing on an upland field in a wide term range of from before germination to growing season, such as gramineous weeds including barnyard grass (*Echinochloa crusglli* var. *crusgalli*), crabgrass (*Digitaria ciliaris*), green foxtail (*Setaria viridis*), annual bluegrass (*Poa annua*), johnsongrass (*Sorghum halepense* Pers.), blackgrass (*Alopecurus myosuroides*), wild oats (*Avena fatua*), and the like, broad leaf weeds including pale persicaria (*Polygonum lapathifolia*), slender amaranth (*Amaranthus viridis*), common lambsquarters (*Chenopodium album* L.), common chickweed (*Stellaria media* Villars), velvetleaf (*Abutilon theophrasti* Medic), prickly sida (*Sida spinosa* L.), Hemp sesbania (*Sesbania exaltata* Cory), common ragweed (*Ambrosia artemisiifolia*), morningglory, and the like, and annual and perennial sedge weeds including purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

Further, the composition of the present invention achieves an excellent herbicidal effect at a small dose to various weeds growing on a paddy field in a wide term range of from before germination to growing season, such as annual weeds including watergrass (*Echinochloa oryzicola*), smallflower umbrella plant (*Cyperus difformis*), konagi (*Monochoria vaginalis*), aze-na (*Lindernia procumbens*) and the like, and perennial weeds including mizu-gayatsuri (*Cyperus serotinus*), kuroguwai (*Eleocharis kuroguwai*), inu-hotaru-i (*Scirpus juncoides*), and the like.

A compound of the following Group A which is another active ingredient to be used in combination with an isoxazoline derivative of the formula (I) or its salt, has less phytotoxicity to gramineous crops such as corn wheat and the like, but has a herbicidal activity to only a part of gramineous weeds such as green foxtail and broad leaf weeds such as barnyardgrass, common lambsquarters and velvetleaf, and its herbicidal spectrum is narrow.

Group A atrazine, simazine, cyanazine, isoxaflutole, mesotrione, flumetsulam, imazethapyr, imazapyr, dicamba, clopyralid, prosulfuron, halosulfuron-methyl, rimsulfuron, bentazone, carfentrazone-ethyl, metribuzin, thifensulfuron-methyl, nicosulfuron, primisulfuron, cloransulam-methyl, glufosinate, glyphosate, glyphosate-trimesium, pendimethalin, linuron, prometryn, diflufenican, flumioxazin, and metolachlor.

The present invention provides a herbicidal composition effective for applying to a new cultivation method such as non-tillage cultivation in order to selectively control a wide range of weeds. The herbicidal composition of the present invention is particularly effective for killing main weeds in a corn field, such as dicotyledons including wild buckwheat (*Fallopia convolvulua* A.), sanae-tade (*Polygonum scabrum*), common purslane (*Portulaca oleracea* L.), common lambsquarters (*Chenopodium album* L.), common amaranth (*Amaranthus retroflexus* L.), wild mustard (*Sinapis Arvensis* L.), hemp sesbania (*Sesbania oxaltata* Cory), sicklepod (*Cassia obtusifolia* L.), velvetleaf (*Abutilon theophrasti* Medic), prickly sida (*Sida spinosa* L.), ivyleaf morningglory (*Ipomoea hederacea* Jacq), common morning glory (*Ipomoea purpurea*), jimsonweek (*Datura stramonium*), black nightshade (*Solanum nigrum* L.), common cocklebur (*Xanthium strumarium* L.), sunflower, field bindweed (*Convolvulus arvensis*), sun spurge (*Euphorbia helioscopia*), devils beggarticks (*Bidens frondosa* L.), common ragweed (*Ambrosia artemisiifolia*) and the like, and monocotyledons including barnyardgrass (*Echinochloa crusglli* var. *crus-galli*), green foxtail (*Setaria viridis*), giant foxtail (*Setari faberi*), yellow foxtail (*Setari glacuca*), crabgrass (*Digitaria ciliaris*), goosegrass (*Eleusine indica* Gaertn), johnsongrass (*Sorghum halepense* Pers.), quackgrass (*Agropyron repens* P.), shattercane (*Sorghum vulgare*), and the like, but does not have phytotoxicity to aimed crops such as corn and soybeans which grow after corn.

The herbicidal composition of the present invention contains at least one compound of Group A in an amount of from 0.001 to 100 parts by weight, preferably from 0.01 to 50 parts by weight, more preferably from 0.05 to 30 parts by weight to 1 part by weight of an isoxazoline derivative of the formula (I) or its salt. If the amount of a herbicide of Group A is less than 0.001 part by weight, a satisfactory effect can not be achieved, and if this amount exceeds 100 parts by weight, safety to aimed crops becomes insufficient.

Among compounds of Group A, at least one compound selected from the group consisting of atrazine, cyanazine, simazine and prometryn, or at least one compound selected from the group consisting of glyphosate, glufosinate, linuron and flumetsulam, is preferable. Particularly, cyanazine or atrazine is preferable.

Next, representative examples of the present compound represented by the general formula (I) are shown in Tables 1 to 14. However, the present compound is not restricted to these examples.

The following abbreviated expressions used in the Tables refer to the following groups.

Me: methyl group Et: ethyl group
Pr: n-propyl group Pr-i: isopropyl group
Pr-c: cyclopropyl group Bu: n-butyl group
Bu-i: isobutyl group Bu-s: sec-butyl group
Bu-t: tert-butyl group Bu-c: cyclobutyl group
Pen: n-pentyl group Pen-c: cyclopentyl group
Hex: n-hexyl group Hex-c: cyclohexyl group
Ph: phenyl group For example, (4-Cl)Ph indicates 4-chlorophenyl group, and 3-Hex indicates 3-hexyl group.

When the present compound contains hydroxyl group as a substituent, there may exist keto-enol tautomers. Any of these tautomers and any mixture of these tautomers are included in the present compound.

TABLE 1

| Comp. No. | $R^1$ | $R^2$ | $R^3$ | $R^4$ | n | $R^5$ | $R^6$ | $Z_1$ | $R^{22}$ | $R^{23}$ | $R^{24}$ | Melting point (° C.) or refractive index ($n_D^{20}$) |
|---|---|---|---|---|---|---|---|---|---|---|---|---|
| 1-0001 | Me | Me | H | H | 2 | H | H | S | Me | H | H | 66-68 |
| 1-0002 | Me | Me | H | H | 2 | H | H | S | Cl | Me | H | 87-88 |
| 1-0003 | Me | Me | H | H | 2 | H | H | S | H | H | Me | 95-97 |
| 1-0004 | Me | Me | H | H | 2 | H | H | S | Cl | H | H | 70-72 |
| 1-0005 | Me | Me | H | H | 2 | H | H | S | H | H | Cl | 118-119 |
| 1-0006 | Me | Me | H | H | 2 | H | H | O | H | H | H | Unmesurable |
| 1-0007 | Me | Me | H | H | 2 | H | H | O | H | H | C(=O)OMe | 124-125 |

TABLE 2

| Comp. No. | $R^1$ | $R^2$ | $R^3$ | $R^4$ | n | $R^5$ | $R^6$ | $Z^2$ | $R^{25}$ | $R^{26}$ | $R^{27}$ | Melting point (° C.) or refractive index ($n_D^{20}$) |
|---|---|---|---|---|---|---|---|---|---|---|---|---|
| 2-0001 | Me | Me | H | H | 2 | H | H | S | Me | C(=NOMe)Me | Me | 95-96 |
| 2-0002 | Me | Me | H | H | 0 | H | H | S | Me | C(=NOMe)Me | Me | |
| 2-0003 | Me | Me | H | H | 2 | H | H | S | H | H | H | 99-101 |
| 2-0004 | Me | Me | H | H | 2 | H | H | S | H | OMe | H | 96-97 |
| 2-0005 | Me | Me | H | H | 2 | H | H | S | Cl | H | Cl | 125-127 |
| 2-0006 | Me | Me | H | H | 2 | H | H | S | Cl | Cl | Cl | 158-160 |
| 2-0007 | Me | Me | H | H | 2 | H | H | S | Me | Me | Me | 117-117 |
| 2-0008 | Me | Me | H | H | 2 | H | H | S | Me | C(=O)Me | Me | 146-148 |
| 2-0009 | Me | Me | H | H | 2 | H | H | S | Ph | C(=O)Me | Me | 1.5730 |
| 2-0010 | Me | Me | H | H | 2 | H | H | S | Ph | C(=NOMe)Me | Me | 129-131 |
| 2-0011 | Me | Me | H | H | 2 | H | H | S | Cl | C(=O)OMe | Cl | 157-158 |
| 2-0012 | Me | Me | H | H | 2 | H | H | S | Cl | C(=O)NHMe | Cl | 178-180 |
| 2-0013 | Me | Me | H | H | 2 | H | H | O | H | H | H | 58-61 |
| 2-0014 | Me | Me | H | H | 2 | H | H | O | Me | H | Cl | 180-181 |

TABLE 3

| Comp. No. | R¹ | R² | R³ | R⁴ | n | R⁵ | R⁶ | R²⁹ | R²⁸ | R³⁰ | Melting point (° C.) or refractive index ($n_D^{20}$) |
|---|---|---|---|---|---|---|---|---|---|---|---|
| 3-0001 | Me | Me | H | H | 0 | H | H | CF₃ | Ph | Cl | 89-90 |
| 3-0002 | Me | Me | H | H | 2 | H | H | CF₃ | Ph | Cl | 132-133 |
| 3-0003 | Me | Me | H | H | 1 | H | H | Ph | Me | Cl | Unmesurable |
| 3-0004 | Me | Me | H | H | 2 | H | H | CF₃ | Ph | SO₂Et | 158-160 |
| 3-0005 | Me | Me | H | H | 2 | H | H | CF₃ | Ph | N(Me)₂ | 150-151 |
| 3-0006 | Me | Me | H | H | 0 | H | H | CF₃ | Bu-t | Cl | 79-81 |
| 3-0007 | Me | Me | H | H | 0 | H | H | CF₃ | H | Cl | 120-122 |
| 3-0008 | Me | Me | H | H | 0 | H | H | CF₃ | CHF₂ | Cl | 41-42 |
| 3-0009 | Me | Me | H | H | 0 | H | H | Cl | CHF₂ | CF₃ | 89-90 |
| 3-0010 | Me | Me | H | H | 2 | H | H | CF₃ | CHF₂ | Cl | 126-127 |
| 3-0011 | Me | Me | H | H | 2 | H | H | Cl | CHF₂ | CF₃ | 136-137 |
| 3-0012 | Me | Me | H | H | 2 | H | H | OEt | Me | CF₃ | 124-125 |
| 3-0013 | Me | Me | H | H | 2 | H | H | CF₃ | Me | OMe | 113-114 |
| 3-0014 | Me | Me | H | H | 2 | H | H | CF₃ | Me | O(2-Cl)Ph | 67-70 |
| 3-0015 | Me | Me | H | H | 2 | H | H | CF₃ | Me | OPen-c | 113-114 |
| 3-0016 | Me | Me | H | H | 2 | H | H | CF₃ | Me | CN | 105-108 |
| 3-0017 | Me | Me | H | H | 2 | H | H | Cl | Et | Cl | 105-107 |
| 3-0018 | Me | Me | H | H | 2 | H | H | CHF₂ | Me | Cl | 78-79 |
| 3-0019 | Me | Me | H | H | 2 | H | H | CF₃ | —(CH₂)₃O— | | 151-152 |
| 3-0020 | Me | Me | H | H | 0 | H | H | CHF₂ | Me | Cl | 1.5183 |
| 3-0021 | Me | Me | H | H | 0 | H | H | CF₃ | Ph | F | |
| 3-0022 | Me | Me | H | H | 0 | H | H | CF₃ | Ph | SEt | |
| 3-0023 | Me | Me | H | H | 0 | H | H | CF₃ | Ph | N(Me)2 | |
| 3-0024 | Me | Me | H | H | 0 | H | H | OMe | Me | CF₃ | |
| 3-0025 | Me | Me | H | H | 0 | H | H | OH | Me | CF₃ | |
| 3-0026 | Me | Me | H | H | 0 | H | H | OEt | Me | CF₃ | |
| 3-0027 | Me | Me | H | H | 0 | H | H | CF₃ | Me | F | |
| 3-0028 | Me | Me | H | H | 0 | H | H | CF₃ | Me | OMe | |
| 3-0029 | Me | Me | H | H | 0 | H | H | CF₃ | Me | O(2-Cl)Ph | |
| 3-0030 | Me | Me | H | H | 0 | H | H | CF₃ | Me | OPen-c | |
| 3-0031 | Me | Me | H | H | 0 | H | H | CF₃ | Me | CN | |
| 3-0032 | Me | Me | H | H | 0 | H | H | Cl | Et | Cl | |
| 3-0033 | Me | Me | H | H | 0 | H | H | CF₃ | —(CH₂)₃O— | | |
| 3-0034 | Me | Me | H | H | 2 | H | H | CF₃ | H | Cl | 138-140 |

TABLE 4

| Comp. No. | R¹ | R² | R³ | R⁴ | n | R⁵ | R⁶ | R²⁹ | R²⁸ | R³⁰ | Melting point (° C.) or refractive index ($n_D^{20}$) |
|---|---|---|---|---|---|---|---|---|---|---|---|
| 3-0035 | Me | Me | H | H | 2 | H | H | H | Me | Cl | 105-106 |
| 3-0036 | Me | Me | H | H | 2 | H | H | Me | Me | Me | 148-150 |
| 3-0037 | Me | Me | H | H | 2 | H | H | Me | Me | Cl | 99-101 |
| 3-0038 | Me | Me | H | H | 2 | H | H | Cl | Me | Cl | 143-145 |
| 3-0039 | Me | Me | H | H | 2 | H | H | CF₃ | Me | Cl | 115-116 |
| 3-0040 | Me | Me | H | H | 2 | H | H | Cl | Me | CF₃ | 120-122 |
| 3-0041 | Me | Me | H | H | 2 | H | H | CF₃ | Me | F | 79-82 |
| 3-0042 | Me | Me | H | H | 2 | H | H | CF₃ | Me | OH | 90-92 |
| 3-0043 | Me | Me | H | H | 2 | H | H | OMe | Me | CF₃ | 125-126 |
| 3-0044 | Me | Me | H | H | 2 | H | H | CF₃ | Me | OEt | 92-94 |
| 3-0045 | Me | Me | H | H | 2 | H | H | CF₃ | Me | OPr-i | 69-71 |
| 3-0046 | Me | Me | H | H | 2 | H | H | CF₃ | Me | OPr | 82-83 |
| 3-0047 | Me | Me | H | H | 2 | H | H | CF₃ | Me | OBu-t | 86-89 |
| 3-0048 | Me | Me | H | H | 2 | H | H | CF₃ | Me | OBu | 61-62 |
| 3-0049 | Me | Me | H | H | 2 | H | H | CF₃ | Me | OHex-c | 124-125 |
| 3-0050 | Me | Me | H | H | 2 | H | H | CF₃ | Me | OCH₂Pr-c | 93-94 |
| 3-0051 | Me | Me | H | H | 2 | H | H | CF₃ | Me | OCH₂Pen-c | 112-113 |
| 3-0052 | Me | Me | H | H | 2 | H | H | CF₃ | Me | OCH₂Hex-c | 56-59 |

TABLE 4-continued

| Comp. No. | $R^1$ | $R^2$ | $R^3$ | $R^4$ | n | $R^5$ | $R^6$ | $R^{29}$ | $R^{28}$ | $R^{30}$ | Melting point (° C.) or refractive index ($n_D^{20}$) |
|---|---|---|---|---|---|---|---|---|---|---|---|
| 3-0053 | Me | Me | H | H | 2 | H | H | $CF_3$ | Me | $OCH_2C\equiv CH$ | 92-93 |
| 3-0054 | Me | Me | H | H | 2 | H | H | $CF_3$ | Me | $OCHF_2$ | 129-130 |
| 3-0055 | Me | Me | H | H | 2 | H | H | $OCHF_2$ | Me | $CF_3$ | Unmesurable |
| 3-0056 | Me | Me | H | H | 2 | H | H | $CF_3$ | Me | $OCH_2CHF_2$ | 89-91 |
| 3-0057 | Me | Me | H | H | 2 | H | H | $CF_3$ | Me | $OCH_2CF_3$ | 93-95 |
| 3-0058 | Me | Me | H | H | 2 | H | H | $CF_3$ | Me | $OCH_2CN$ | 1.4872 |
| 3-0059 | Me | Me | H | H | 2 | H | H | $CF_3$ | Me | $OCH_2Ph$ | 79-81 |
| 3-0060 | Me | Me | H | H | 2 | H | H | $CF_3$ | Me | OPh | 122-123 |
| 3-0061 | Me | Me | H | H | 2 | H | H | $CF_3$ | Me | O(3-Cl)Ph | Unmesurable |
| 3-0062 | Me | Me | H | H | 2 | H | H | $CF_3$ | Me | O(3-OMe)Ph | 1.5059 |
| 3-0063 | Me | Me | H | H | 2 | H | H | $CF_3$ | Me | O(4-Cl)Ph | 68-69 |
| 3-0064 | Me | Me | H | H | 2 | H | H | $CF_3$ | Me | O(4-Me)Ph | 132-133 |
| 3-0065 | Me | Me | H | H | 2 | H | H | $CF_3$ | Me | O(4-OMe)Ph | 115-117 |
| 3-0066 | Me | Me | H | H | 2 | H | H | $CF_3$ | Me | OC(=O)Me | 130-131 |
| 3-0067 | Me | Me | H | H | 2 | H | H | $CF_3$ | Me | $SO_2Me$ | 168-169 |
| 3-0068 | Me | Me | H | H | 2 | H | H | $CF_3$ | Me | SEt | 100-102 |
| 3-0069 | Me | Me | H | H | 2 | H | H | $CF_3$ | Me | $SO_2Et$ | 107-108 |
| 3-0070 | Me | Me | H | H | 2 | H | H | $CF_3$ | Me | $SO_2Ph$ | 166-168 |
| 3-0071 | Me | Me | H | H | 2 | H | H | $CF_3$ | Me | Me | 105-107 |
| 3-0072 | Me | Me | H | H | 2 | H | H | Ph | Me | Cl | 127-129 |
| 3-0073 | Me | Me | H | H | 2 | H | H | $CF_3$ | Et | Cl | 111-112 |

TABLE 5

| Comp. No. | $R^1$ | $R^2$ | $R^3$ | $R^4$ | n | $R^5$ | $R^6$ | $R^{29}$ | $R^{28}$ | $R^{30}$ | Melting point (° C.) or refractive index ($n_D^{20}$) |
|---|---|---|---|---|---|---|---|---|---|---|---|
| 3-0074 | Me | Me | H | H | 2 | H | H | Cl | Et | $CF_3$ | 112-114 |
| 3-0075 | Me | Me | H | H | 2 | H | H | $CF_3$ | Pr-i | Cl | 157-158 |
| 3-0076 | Me | Me | H | H | 2 | H | H | Cl | Pr-i | $CF_3$ | 135-136 |
| 3-0077 | Me | Me | H | H | 2 | H | H | $CF_3$ | Pr | Cl | 89-90 |
| 3-0078 | Me | Me | H | H | 2 | H | H | Cl | Pr | $CF_3$ | 111-113 |
| 3-0079 | Me | Me | H | H | 2 | H | H | $CF_3$ | Bu-t | H | 101-103 |
| 3-0080 | Me | Me | H | H | 2 | H | H | $CF_3$ | Bu-t | Cl | 118-119 |
| 3-0081 | Me | Me | H | H | 2 | H | H | $CF_3$ | Bu-s | Cl | 110-112 |
| 3-0082 | Me | Me | H | H | 2 | H | H | Cl | Bu-s | $CF_3$ | 110-111 |
| 3-0083 | Me | Me | H | H | 2 | H | H | $CF_3$ | Bu-i | Cl | 96-98 |
| 3-0084 | Me | Me | H | H | 2 | H | H | Cl | Bu-i | $CF_3$ | 140-141 |
| 3-0085 | Me | Me | H | H | 2 | H | H | $CF_3$ | Bu | Cl | 89-90 |
| 3-0086 | Me | Me | H | H | 2 | H | H | Cl | Bu | $CF_3$ | 108-110 |
| 3-0087 | Me | Me | H | H | 2 | H | H | $CF_3$ | $CH_2Ph$ | Cl | 132-133 |
| 3-0088 | Me | Me | H | H | 2 | H | H | Cl | $CH_2Ph$ | $CF_3$ | 118-120 |
| 3-0089 | Me | Me | H | H | 2 | H | H | $CF_3$ | Pen-c | Cl | 130-131 |
| 3-0090 | Me | Me | H | H | 2 | H | H | Cl | Pen-c | $CF_3$ | 147-148 |
| 3-0091 | Me | Me | H | H | 2 | H | H | $CF_3$ | Hex-c | Cl | 151-152 |
| 3-0092 | Me | Me | H | H | 2 | H | H | $CF_3$ | $CH_2Pr$-c | Cl | 93-95 |
| 3-0093 | Me | Me | H | H | 2 | H | H | Cl | $CH_2Pr$-c | $CF_3$ | 129-130 |
| 3-0094 | Me | Me | H | H | 2 | H | H | $CF_3$ | 1-cyclopropylethyl | Cl | 87-89 |
| 3-0095 | Me | Me | H | H | 2 | H | H | Cl | 1-cyclopropylethyl | $CF_3$ | 121-123 |
| 3-0096 | Me | Me | H | H | 2 | H | H | $CF_3$ | $CH_2$(2-Methylcyclopropyl) | Cl | 102-103 |
| 3-0097 | Me | Me | H | H | 2 | H | H | Cl | $CH_2$(2-Methylcyclopropyl) | $CF_3$ | 118-119 |
| 3-0098 | Me | Me | H | H | 2 | H | H | $CF_3$ | $CH_2Bu$-c | Cl | 94-96 |
| 3-0099 | Me | Me | H | H | 2 | H | H | Cl | $CH_2Bu$-c | $CF_3$ | 141-142 |
| 3-0100 | Me | Me | H | H | 2 | H | H | $CF_3$ | $CH_2Pen$-c | Cl | 127-129 |
| 3-0101 | Me | Me | H | H | 2 | H | H | Cl | $CH_2Pen$-c | $CF_3$ | 146-149 |
| 3-0102 | Me | Me | H | H | 2 | H | H | $CF_3$ | $CH_2Hex$-c | Cl | 152-154 |
| 3-0103 | Me | Me | H | H | 2 | H | H | Cl | $CH_2Hex$-c | $CF_3$ | 115-117 |
| 3-0104 | Me | Me | H | H | 2 | H | H | $CF_3$ | $CH_2CH=CH_2$ | Cl | 78-80 |
| 3-0105 | Me | Me | H | H | 2 | H | H | Cl | $CH_2CH=CH_2$ | $CF_3$ | 105-106 |
| 3-0106 | Me | Me | H | H | 2 | H | H | $CF_3$ | $CH_2C\equiv CH$ | Cl | 73-74 |
| 3-0107 | Me | Me | H | H | 2 | H | H | Cl | $CH_2C\equiv CH$ | $CF_3$ | 108-109 |
| 3-0108 | Me | Me | H | H | 2 | H | H | $CF_3$ | $CHMeC\equiv CH$ | Cl | 95-96 |
| 3-0109 | Me | Me | H | H | 2 | H | H | Cl | $CHMeC\equiv CH$ | $CF_3$ | 116-118 |
| 3-0110 | Me | Me | H | H | 2 | H | H | $CF_3$ | $CH_2C\equiv CMe$ | Cl | 114-115 |
| 3-0111 | Me | Me | H | H | 2 | H | H | Cl | $CH_2C\equiv CMe$ | $CF_3$ | 115-116 |
| 3-0112 | Me | Me | H | H | 2 | H | H | $CF_3$ | $CHF_2$ | OMe | 72-74 |

TABLE 6

| Comp. No. | R¹ | R² | R³ | R⁴ | n | R⁵ | R⁶ | R²⁹ | R²⁸ | R³⁰ | Melting point (° C.) or refractive index ($n_D^{20}$) |
|---|---|---|---|---|---|---|---|---|---|---|---|
| 3-0113 | Me | Me | H | H | 2 | H | H | OMe | CHF$_2$ | CF$_3$ | 108-109 |
| 3-0114 | Me | Me | H | H | 2 | H | H | CF$_3$ | CH$_2$CHF$_2$ | Cl | 99-100 |
| 3-0115 | Me | Me | H | H | 2 | H | H | Cl | CH$_2$CHF$_2$ | CF$_3$ | 107-109 |
| 3-0116 | Me | Me | H | H | 2 | H | H | CF$_3$ | CH$_2$CF$_3$ | Cl | 135-136 |
| 3-0117 | Me | Me | H | H | 2 | H | H | Cl | CH$_2$CF$_3$ | CF$_3$ | 112-115 |
| 3-0118 | Me | Me | H | H | 2 | H | H | CF$_3$ | CH$_2$OMe | Cl | 87-89 |
| 3-0119 | Me | Me | H | H | 2 | H | H | Cl | CH$_2$OMe | CF$_3$ | 125-128 |
| 3-0120 | Me | Me | H | H | 2 | H | H | CF$_3$ | CH$_2$OEt | Cl | 97-98 |
| 3-0121 | Me | Me | H | H | 2 | H | H | Cl | CH$_2$OEt | CF$_3$ | 128-129 |
| 3-0122 | Me | Me | H | H | 2 | H | H | CF$_3$ | CH$_2$CH$_2$OH | Cl | 79-81 |
| 3-0123 | Me | Me | H | H | 2 | H | H | Cl | CH$_2$CH$_2$OH | CF$_3$ | 93-94 |
| 3-0124 | Me | Me | H | H | 2 | H | H | CF$_3$ | CH$_2$CH$_2$OMe | Cl | 102-104 |
| 3-0125 | Me | Me | H | H | 2 | H | H | Cl | CH$_2$CH$_2$OMe | CF$_3$ | 118-119 |
| 3-0126 | Me | Me | H | H | 2 | H | H | CF$_3$ | CH$_2$CH$_2$OEt | Cl | 56-59 |
| 3-0127 | Me | Me | H | H | 2 | H | H | Cl | CH$_2$CH$_2$OEt | CF$_3$ | 118-119 |
| 3-0128 | Me | Me | H | H | 2 | H | H | CF$_3$ | CH$_2$SMe | Cl | 103-105 |
| 3-0129 | Me | Me | H | H | 2 | H | H | Cl | CH$_2$SMe | CF$_3$ | 128-129 |
| 3-0130 | Me | Me | H | H | 2 | H | H | CF$_3$ | CH$_2$SO$_2$Me | Cl | 157-159 |
| 3-0131 | Me | Me | H | H | 2 | H | H | Cl | CH$_2$SO$_2$Me | CF$_3$ | 165-166 |
| 3-0132 | Me | Me | H | H | 2 | H | H | CF$_3$ | CH$_2$CH$_2$SO$_2$Me | Cl | 155-157 |
| 3-0133 | Me | Me | H | H | 2 | H | H | Cl | CH$_2$CH$_2$SO$_2$Me | CF$_3$ | 166-168 |
| 3-0134 | Me | Me | H | H | 2 | H | H | CF$_3$ | CH$_2$CN | Cl | 128-129 |
| 3-0135 | Me | Me | H | H | 2 | H | H | Cl | CH$_2$CN | CF$_3$ | 117-118 |
| 3-0136 | Me | Me | H | H | 2 | H | H | CF$_3$ | CH$_2$C(=O)OEt | Cl | 127-129 |
| 3-0137 | Me | Me | H | H | 2 | H | H | Cl | CH$_2$C(=O)OEt | CF$_3$ | 143-145 |
| 3-0138 | Me | Me | H | H | 2 | H | H | CF$_3$ | CH$_2$C(=O)NH$_2$ | Cl | 173-174 |
| 3-0139 | Me | Me | H | H | 2 | H | H | Cl | CH$_2$C(=O)NH$_2$ | CF$_3$ | 182-183 |
| 3-0140 | Me | Me | H | H | 2 | H | H | CF$_3$ | CH$_2$C(=O)N(Me)$_2$ | Cl | 142-143 |
| 3-0141 | Me | Me | H | H | 2 | H | H | Cl | CH$_2$C(=O)N(Me)$_2$ | CF$_3$ | 181-182 |
| 3-0142 | Me | Me | H | H | 2 | H | H | CF$_3$ | CH$_2$C(=O)Me | Cl | 148-149 |
| 3-0143 | Me | Me | H | H | 2 | H | H | Cl | CH$_2$C(=O)Me | CF$_3$ | 163-164 |
| 3-0144 | Me | Me | H | H | 2 | H | H | CF$_3$ | CH$_2$CH$_2$C(=O)Me | Cl | 89-91 |
| 3-0145 | Me | Me | H | H | 2 | H | H | Me | Ph | Me | 140-141 |
| 3-0146 | Me | Me | H | H | 2 | H | H | Me | Ph | Cl | 124-125 |
| 3-0147 | Me | Me | H | H | 2 | H | H | Et | Ph | Cl | 112-113 |
| 3-0148 | Me | Me | H | H | 2 | H | H | Pr | Ph | Cl | 122-123 |
| 3-0149 | Me | Me | H | H | 2 | H | H | Pr-i | Ph | Cl | 116-117 |
| 3-0150 | Me | Me | H | H | 2 | H | H | Bu-t | Ph | Cl | 100-102 |
| 3-0151 | Me | Me | H | H | 2 | H | H | CF$_3$Lr$_3$ | Ph | H | 111-112 |

TABLE 7

| Comp. No. | R¹ | R² | R³ | R⁴ | n | R⁵ | R⁶ | R²⁹ | R²⁸ | R³⁰ | Melting point (° C.) or refractive index ($n_D^{20}$) |
|---|---|---|---|---|---|---|---|---|---|---|---|
| 3-0152 | Me | Me | H | H | 2 | H | H | CF$_3$ | Ph | Me | 129-132 |
| 3-0153 | Me | Me | H | H | 2 | H | H | CF$_3$ | Ph | CF$_3$ | 112-113 |
| 3-0154 | Me | Me | H | H | 2 | H | H | CF$_3$ | Ph | F | 90-91 |
| 3-0155 | Me | Me | H | H | 2 | H | H | CF$_3$ | Ph | OMe | 104-106 |
| 3-0156 | Me | Me | H | H | 2 | H | H | CF$_3$ | Ph | OEt | 129-131 |
| 3-0157 | Me | Me | H | H | 2 | H | H | CF$_3$ | Ph | OPr-i | 86-88 |
| 3-0158 | Me | Me | H | H | 2 | H | H | CF$_3$ | Ph | OPr | 117-118 |
| 3-0159 | Me | Me | H | H | 2 | H | H | CF$_3$ | Ph | OBu-t | 105-108 |
| 3-0160 | Me | Me | H | H | 2 | H | H | CF$_3$ | Ph | OCHF$_2$ | 90-92 |
| 3-0161 | Me | Me | H | H | 2 | H | H | CF$_3$ | Ph | SO$_2$Me | 167-168 |
| 3-0162 | Me | Me | H | H | 2 | H | H | CF$_3$ | Ph | CN | 113-115 |
| 3-0163 | Me | Me | H | H | 2 | H | H | CF$_3$ | (2-Cl)Ph | Cl | 153-154 |
| 3-0164 | Me | Me | H | H | 2 | H | H | CF$_3$ | (3-Cl)Ph | Cl | 106-107 |
| 3-0165 | Me | Me | H | H | 2 | H | H | CF$_3$ | (4-Cl)Ph | Cl | 142-143 |
| 3-0166 | Me | Me | H | H | 2 | H | H | CF$_3$ | (4-F)Ph | Cl | 135-138 |
| 3-0167 | Me | Me | H | H | 2 | H | H | CF$_3$ | (4-OMe)Ph | Cl | 136-138 |
| 3-0168 | Me | Me | H | H | 2 | H | H | CF$_3$ | (4-Me)Ph | Cl | 129-130 |
| 3-0169 | Me | Me | H | H | 2 | H | H | CF$_3$ | (4-NO$_2$)Ph | Cl | 145-147 |
| 3-0170 | Me | Me | H | H | 2 | H | H | CF$_3$ | (4-CN)Ph | Cl | 91-93 |
| 3-0171 | Me | Me | H | H | 2 | H | H | CF$_3$ | (4-C(=O)Me)Ph | Cl | 133-135 |
| 3-0172 | Me | Me | H | H | 2 | H | H | CF$_3$ | (4-C(=O)OMe)Ph | Cl | 121-124 |
| 3-0173 | Me | Me | H | H | 2 | H | H | CF$_3$ | Pyrmidin-2-yl | Cl | 148-150 |

TABLE 7-continued

| Comp. No. | R¹ | R² | R³ | R⁴ | n | R⁵ | R⁶ | R²⁹ | R²⁸ | R³⁰ | Melting point (° C.) or refractive index ($n_D^{20}$) |
|---|---|---|---|---|---|---|---|---|---|---|---|
| 3-0174 | Me | Me | H | H | 2 | H | H | CF₃ | 4,6-Dimethoxy-pyrmidin-2-yl | Cl | 117-118 |
| 3-0175 | Me | Me | H | H | 2 | H | H | CF₃ | SO₂Me | Cl | 146-148 |
| 3-0176 | Me | Me | H | H | 2 | H | H | CF₃ | SO₂Ph | Cl | 145-148 |
| 3-0177 | Me | Me | H | H | 2 | H | H | CF₃ | C(=O)Me | Cl | 130-131 |
| 3-0178 | Me | Me | H | H | 2 | H | H | CF₃ | C(=O)Ph | Cl | 114-117 |
| 3-0179 | Me | Me | H | H | 2 | H | H | CF₃ | C(=O)OMe | Cl | 104-106 |
| 3-0180 | Me | Et | H | H | 2 | H | H | CF₃ | Me | Cl | 108-110 |
| 3-0181 | Me | Me | H | H | 0 | H | H | CHF₂ | Me | Cl | 1.5183 |
| 3-0182 | Me | Me | H | H | 0 | H | H | Ph | Me | Cl | 76-77 |
| 3-0183 | Me | Me | H | H | 0 | H | H | CF₃ | Bu-t | OMe | 1.4831 |
| 3-0184 | Me | Me | H | H | 0 | H | H | CF₃ | CH₂C(=O)NH₂ | Cl | 179-180 |
| 3-0185 | Me | Me | H | H | 0 | H | H | Me | Ph | Cl | 58-60 |
| 3-0186 | Me | Me | H | H | 0 | H | H | CF₃ | Me | Cl | |
| 3-0187 | Me | Me | H | H | 0 | H | H | CF₃ | Me | OCHF₂ | |
| 3-0188 | Me | Me | H | H | 2 | H | H | CF₃ | Me | OCHF₂ | 129-130 |
| 3-0189 | Me | Me | H | H | 0 | H | H | CF₃ | Et | OCHF₂ | |
| 3-0190 | Me | Me | H | H | 2 | H | H | CF₃ | Et | OCHF₂ | 98-100 |

TABLE 8

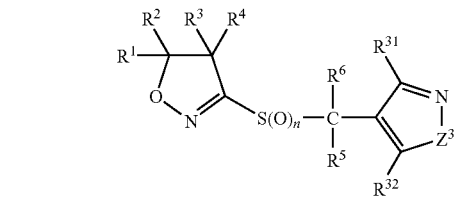

| Comp. No. | R¹ | R² | R³ | R⁴ | n | R⁵ | R⁶ | Z³ | R³¹ | R³² | Melting point (° C.) or refractive index ($n_D^{20}$) |
|---|---|---|---|---|---|---|---|---|---|---|---|
| 4-0001 | Me | Me | H | H | 2 | H | H | O | CF₃ | Me | 135-136 |
| 4-0002 | Me | Me | H | H | 2 | H | H | S | Me | Cl | 113-114 |
| 4-0003 | Me | Me | H | H | 0 | H | H | O | CF₃ | Me | |
| 4-0004 | Me | Me | H | H | 0 | H | H | S | Me | Cl | |
| 4-0005 | Me | Me | H | H | 2 | H | H | O | Me | Me | 178-179 |
| 4-0006 | Me | Me | H | H | 2 | H | H | O | CF₃ | OEt | 89-91 |
| 4-0007 | Me | Me | H | H | 2 | H | H | O | Ph | Me | 81-83 |
| 4-0008 | Me | Me | H | H | 2 | H | H | S | Me | OEt | 109-111 |

TABLE 9

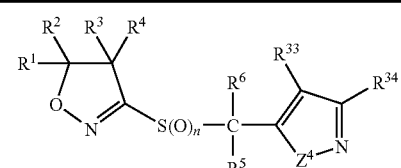

| Comp. No. | R¹ | R² | R³ | R⁴ | n | R⁵ | R⁶ | Z⁴ | R³³ | R³⁴ | Melting point (° C.) or refractive index ($n_D^{20}$) |
|---|---|---|---|---|---|---|---|---|---|---|---|
| 5-0001 | Me | Me | H | H | 2 | H | H | NMe | Cl | Me | 114-115 |
| 5-0002 | Me | Me | H | H | 2 | H | H | NMe | Cl | Et | 107-108 |
| 5-0003 | Me | Me | H | H | 2 | H | H | NMe | CF₃ | H | 142-143 |
| 5-0004 | Me | Me | H | H | 2 | H | H | NCHF₂ | —(CH₂)₄— | | 123-125 |
| 5-0005 | Me | Me | H | H | 2 | H | H | NPh | OEt | Me | 1.5397 |

TABLE 9-continued

| Comp. No. | R$^1$ | R$^2$ | R$^3$ | R$^4$ | n | R$^5$ | R$^6$ | Z$^4$ | R$^{33}$ | R$^{34}$ | Melting point (° C.) or refractive index (n$_D^{20}$) |
|---|---|---|---|---|---|---|---|---|---|---|---|
| 5-0006 | Me | Me | H | H | 2 | H | H | NPh | OCHF$_2$ | Me | 1.5339 |
| 5-0007 | Me | Me | H | H | 2 | H | H | NPh | CF$_3$ | H | 99-101 |
| 5-0008 | Me | Me | H | H | 2 | H | H | NPh | OCH$_2$CH=CH$_2$ | Me | 87-90 |
| 5-0009 | Me | Me | H | H | 1 | H | H | NPh | OCH$_2$CH=CH$_2$ | Me | 1.5702 |

TABLE 10

| Comp. No. | R$^1$ | R$^2$ | R$^3$ | R$^4$ | n | R$^5$ | R$^6$ | Z$^5$ | R$^{35}$ | R$^{36}$ | Melting point (° C.) or refractive index (n$_D^{20}$) |
|---|---|---|---|---|---|---|---|---|---|---|---|
| 6-0001 | Me | Me | H | H | 2 | H | H | NCHF$_2$ | —(CH$_2$)$_4$— | | Unmesurable |
| 6-0002 | Me | Me | H | H | 2 | H | H | NPh | H | OEt | 107-108 |
| 6-0003 | Me | Me | H | H | 2 | H | H | NPh | H | OCHF$_2$ | 1.5383 |
| 6-0004 | Me | Me | H | H | 2 | H | H | O | Me | H | 100-102 |
| 6-0005 | Me | Me | H | H | 0 | H | H | NCHF$_2$ | —(CH$_2$)$_4$— | | 1.5264 |

TABLE 11

| Comp. No. | R$^1$ | R$^2$ | R$^3$ | R$^4$ | n | R$^5$ | R$^6$ | R$^{37}$ | R$^{38}$ | R$^{39}$ | R$^{40}$ | | Melting point (° C.) or refractive index (n$_D^{20}$) |
|---|---|---|---|---|---|---|---|---|---|---|---|---|---|
| 7-0001 | Me | Me | H | H | 2 | H | H | H | CF$_3$ | H | H | — | 77-80 |
| 7-0002 | Me | Me | H | H | 2 | H | H | H | CF$_3$ | H | H | N-oxide | 114-116 |
| 7-0003 | Me | Me | H | H | 0 | H | H | H | CF$_3$ | H | H | — | |
| 7-0004 | Me | Me | H | H | 2 | H | H | H | H | H | H | — | 130-131 |
| 7-0005 | Me | Me | H | H | 2 | H | H | H | H | H | H | N-oxide | 166-168 |
| 7-0006 | Me | Me | H | H | 2 | H | H | Cl | Ph | H | H | — | 118-120 |
| 7-0007 | Me | Me | H | H | 2 | H | H | OMe | Ph | H | H | — | 105-106 |
| 7-0008 | Me | Me | H | H | 2 | H | H | Cl | Me | H | H | — | 115-116 |
| 7-0009 | Me | Me | H | H | 2 | H | H | OMe | Me | H | H | — | 134-135 |

TABLE 11-continued

| Comp. No. | R¹ | R² | R³ | R⁴ | n | R⁵ | R⁶ | R³⁷ | R³⁸ | R³⁹ | R⁴⁰ | | Melting point (° C.) or refractive index ($n_D^{20}$) |
|---|---|---|---|---|---|---|---|---|---|---|---|---|---|
| 7-0010 | Me | Me | H | H | 2 | H | H | Me | Me | H | H | N-oxide | 198-199 |
| 7-0011 | Me | Me | H | H | 2 | H | H | Ph | Ph | H | H | — | 161-162 |
| 7-0012 | Me | Me | H | H | 1 | H | H | H | H | H | H | — | 97-99 |
| 7-0013 | Me | Me | H | H | 0 | H | H | (2-Chloropyridin-3-yl)methylthio | H | H | H | — | 154-155 |

TABLE 12

| Comp. No. | R¹ | R² | R³ | R⁴ | n | R⁵ | R⁶ | R⁴¹ | R⁴² | R⁴³ | Melting point (° C.) or refractive index ($n_D^{20}$) |
|---|---|---|---|---|---|---|---|---|---|---|---|
| 8-0001 | Me | Me | H | H | 2 | H | H | H | OMe | CF₃ | 175-176 |
| 8-0002 | Me | Me | H | H | 0 | H | H | H | OMe | CF₃ | |
| 8-0003 | Me | Me | H | H | 2 | H | H | H | Cl | Cl | 119-120 |
| 8-0004 | Me | Me | H | H | 2 | H | H | H | OEt | CF₃ | 94-95 |
| 8-0005 | Me | Me | H | H | 2 | H | H | H | OMe | OMe | 186-187 |
| 8-0006 | Me | Me | H | H | 2 | H | H | Me | OMe | CF₃ | 143-144 |
| 8-0007 | Me | Me | H | H | 2 | H | H | OMe | OMe | CF₃ | 144-145 |
| 8-0008 | Me | Me | H | H | 2 | H | H | SMe | OMe | CF₃ | 160-162 |
| 8-0009 | Me | Me | H | H | 2 | H | H | SO₂Me | OMe | CF₃ | 144-146 |
| 8-0010 | Me | Me | H | H | 2 | H | H | NH₂ | OMe | CF₃ | 208-209 |
| 8-0011 | Me | Me | H | H | 2 | Pr-i | H | H | H | CF₃ | 112-113 |
| 8-0012 | Me | Me | H | H | 0 | Pr-i | H | H | H | CF₃ | 1.4986 |

TABLE 13

| Comp. No. | R¹ | R² | R³ | R⁴ | n | R⁵ | R⁶ | Y¹ | Melting point (° C.) or refractive index ($n_D^{20}$) |
|---|---|---|---|---|---|---|---|---|---|
| 9-0001 | Me | Me | H | H | 2 | H | H | Pyridin-2-yl | 116-118 |
| 9-0002 | Me | Me | H | H | 2 | H | H | Pyridin-2-yl 1-oxide | 140-143 |
| 9-0003 | Me | Me | H | H | 2 | H | H | Pyridin-4-yl | 133-136 |

TABLE 13-continued $$\begin{array}{c} R^2 \; R^3 \; R^4 \\ R^1 \diagdown \\ O \diagdown \\ N \end{array} S(O)_n - \underset{R^5}{\overset{R^6}{\underset{|}{C}}} - Y^1$$

| Comp. No. | $R^1$ | $R^2$ | $R^3$ | $R^4$ | n | $R^5$ | $R^6$ | $Y^1$ | Melting point (° C.) or refractive index ($n_D^{20}$) |
|---|---|---|---|---|---|---|---|---|---|
| 9-0004 | Me | Me | H | H | 2 | H | H | Pyridin-4-yl 1-oxide | 110-113 |
| 9-0005 | Me | Me | H | H | 2 | H | H | 1,2,4-Oxadiazol-3-yl | Unmesurable |
| 9-0006 | Me | Me | H | H | 2 | H | H | 3-Phenyl-1,2,4-oxadiazol-5-yl | 153-154 |
| 9-0007 | Me | Me | H | H | 2 | H | H | 3-Benzyl-1,2,4-oxadiazol-5-yl | 108-109 |
| 9-0008 | Me | Me | H | H | 2 | H | H | 2-Chlorothiazol-4-yl | 110-112 |
| 9-0009 | Me | Me | H | H | 2 | H | H | 1,4-Dimethylimidazol-5-yl | 163-164 |
| 9-0010 | Me | Me | H | H | 1 | H | H | Pyridin-2-yl | 81-82 |
| 9-0011 | Me | Me | H | H | 1 | H | H | Pyridin-4-yl | 94-96 |
| 9-0012 | Me | Me | H | H | 1 | H | H | 1,4-Dimethylimidazol-5-yl | 138-140 |
| 9-0013 | Me | Me | H | H | 0 | H | H | 1,4-Dimethylimidazol-5-yl | 1.5427 |

TABLE 14

$$\begin{array}{c} R^2 \; R^3 \; R^4 \\ R^1 \diagdown \\ O \diagdown \\ N \end{array} S(O)_n - \underset{R^5}{\overset{R^6}{\underset{|}{C}}} - Y^1$$

| Comp. No. | $R^1$ | $R^2$ | $R^3$ | $R^4$ | n | $R^5$ | $R^6$ | $Y^1$ | Melting point (° C.) or refractive index ($n_D^{20}$) |
|---|---|---|---|---|---|---|---|---|---|
| 10-0001 | Me | Me | H | H | 2 | H | H | Benzimidazol-2-yl | 171-174 |
| 10-0002 | Me | Me | H | H | 2 | H | H | Benzothiophen-2-yl | 181-183 |
| 10-0003 | Me | Me | H | H | 2 | H | H | 3-Chlorobenzothiophen-2-yl | 109-112 |
| 10-0004 | Me | Me | H | H | 2 | H | H | Benzotriazol-1-yl | 206-207 |
| 10-0005 | Me | Me | H | H | 2 | H | H | 1-Methylindazol-4-yl | 128-130 |
| 10-0006 | Me | Me | H | H | 2 | H | H | Benzothiazol-2-yl | 142-143 |
| 10-0007 | Me | Me | H | H | 2 | H | H | Benzothiophen-3-yl | 188-191 |
| 10-0008 | Me | Me | H | H | 2 | H | H | 5-Chlorobenzothiophen-3-yl | 129-130 |
| 10-0009 | Me | Me | H | H | 2 | H | H | Benzoxazol-2-yl | 127-129 |
| 10-0010 | Me | Me | H | H | 2 | H | H | 3-Methylbenzothiophen-2-yl | 161-163 |
| 10-0011 | Me | Me | H | H | 2 | H | H | 3-Bromobenzothiophen-2-yl | 118-119 |
| 10-0012 | Me | Me | H | H | 2 | H | H | Benzofuran-2-yl | 123-124 |
| 10-0013 | Me | Me | H | H | 2 | H | H | 2-Methylbenzofuran-7-yl | 135-137 |
| 10-0014 | Me | Me | H | H | 2 | H | H | 3-Bromobenzofuran-2-yl | 107-108 |
| 10-0015 | Me | Me | H | H | 2 | H | H | Benzothiophen-7-yl | 95-97 |
| 10-0016 | Me | Me | H | H | 2 | H | H | 1-Methylindazol-7-yl | 89-90 |
| 10-0017 | Me | Me | H | H | 2 | H | H | 3-Methylbenzofuran-2-yl | 111-112 |
| 10-0018 | Me | Me | H | H | 2 | H | H | 3-Chloro-1-methylindol-2-yl | 162-165 |

In using the composition of the present invention as a herbicide, the present composition may be used in a mixture by itself without adding other compounds, but it can also be used in the form of a wettable powder, granules, fine granules, a powder, an emulsifiable concentrate, a solution, a suspension, a flowable, etc. by mixing with a carrier, a surfactant, a dispersant, an adjuvant, etc. all generally usable in formulation.

As the carrier usable in formulation, there can be mentioned, for example, solid carriers such as talc, bentonite, clay, kaolin, diatomaceous earth, white carbon, vermiculite, calcium carbonate, slaked lime, siliceous sand, ammonium sulfate, urea and the like; and liquid carriers such as isopropyl alcohol, xylene, cyclohexane, methylnaphthalene and the like.

As the surfactant and the dispersant, there can be mentioned, for example, metal salts of alkylbenzenesulfonic acids, metal salts of an alkylnaphthalenesulfonic acid-formalin condensate, salts of alcohol sulfates, alkylarylsulfonic acid salts, ligninsulfonic acid salts, polyoxyethylene glycol ethers, polyoxyethylene alkyl aryl ethers, monoalkylates of polyoxyethylene sorbitan and the like. As the adjuvant, there can be mentioned, for example, carboxymethyl cellulose, polyethylene glycol and gum arabic.

Also, the composition of the present invention may be prepared by formulating respective active ingredients in the above-mentioned manner and then mixing the respective ingredients. The composition of the present invention thus formulated may be applied to plants as it is or may be applied after diluting with water or the like. The composition of the present invention may be mixed with other herbicides to enhance its herbicidal effect, or may be used further in combination with an insecticide, a fungicide, a plant growth-regulating agent, a fertilizer, a soil-improving agent or the like.

The composition of the present invention contains an isoxazoline derivative of the formula (I) or its salt and at least one compound selected from Group A preferably in a total amount of from 0.5 to 90 wt %, more preferably from 1 to 80 wt %.

Also, an isoxazoline derivative of the formula (I) or its salt may be mixed with two or more compounds selected from Group A, and its application amount is preferably from 0.5 to 90 wt %, more preferably from 1 to 80 wt %, in a total amount of the two ingredients.

The compound of the formula (I) used in the composition of the present invention can be prepared as illustrated in the following Preparation Examples, but should not be limited thereto.

Preparation Example 1

Production of 3-(5-chloro-1-phenyl-3-trifluoromethyl-1H-pyrazol-4-ylmethylthio)-5,5-dimethyl-2-isoxazoline (Present Compound No. 3-0001)

2.1 g of sodium hydrosulfide hydrate (purity: 70%, 26.2 mmoles) was added to a solution of 2.3 g (13.1 mmoles) of 3-methylsulfonyl-5,5-dimethyl-2-isoxazoline dissolved in 20 ml of N,N-dimethylformamide. The mixture was stirred for 2 hours. Thereto were added 1.8 g (13.1 mmoles) of anhydrous potassium carbonate, 2.0 g (13.1 mmoles) of Rongalit and 3.6 g (10.5 mmoles) of 4-bromomethyl-5-chloro-1-phenyl-3-trifluoromethyl-1H-pyrazole. The resulting mixture was stirred at room temperature for 15 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.7 g (yield: 65.5%) of 3-(5-chloro-1-phenyl-3-trifluoromethyl-1H-pyrazol-4-ylmethylthio)-5,5-dimethyl-2-isoxazoline as white crystals (melting point: 89 to 90° C.).
$^1$H-NMR [CDCl$_3$/TMS, δ (ppm)]:
7.55-7.50 (5H, m), 4.33 (2H, s), 2.83 (2H, s), 1.45 (6H, s)

Preparation Example 2

Production of 3-(5-chloro-1-phenyl-3-trifluoromethyl-1H-pyrazol-4-ylmethylsulfonyl)-5,5-dimethyl-2-isoxazoline (Present Compound No. 3-0002)

0.63 g of m-chloroperbenzoic acid (purity: 70%, 2.6 mmoles) was added, with ice-cooling, to a solution of 0.4 g (1.0 mmoles) of 3-(5-chloro-1-phenyl-3-trifluoromethyl-1H-pyrazol-4-ylmethylthio)-5,5-dimethyl-2-isoxazoline dissolved in 15 ml of chloroform. The mixture was stirred at room temperature for 22 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 0.4 g (yield: 83.2%) of 3-(5-chloro-1-phenyl-3-trifluoromethyl-1H-pyrazol-4-ylmethylsulfonyl)-5,5-dimethyl-2-isoxazoline as white crystals (melting point: 132 to 133° C.).
$^1$H-NMR [CDCl$_3$/TMS, δ (ppm)]:
7.60-7.51 (5H, m), 4.37 (2H, s), 3.14 (2H, s) 1.53 (6H, s)

Preparation Example 3

Production of 3-(5-chloro-1-methyl-3-phenyl-1H-pyrazol-4-ylmethylsulfinyl)-5,5-dimethyl-2-isoxazoline (Present Compound No. 3-0003)

0.87 g of m-chloroperbenzoic acid (purity: 70%, 3.54 mmoles) was added, with ice-cooling, to a solution of 0.85 g (2.53 mmoles) of 3-(5-chloro-1-methyl-3-phenyl-1H-pyrazol-4-ylmethylthio)-5,5-dimethyl-2-isoxazoline dissolved in 30 ml of chloroform. The mixture was stirred at room temperature for 1 hour to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.48 g (yield: 53.9%) of 3-(5-chloro-1-methyl-3-phenyl-1H-pyrazol-4-ylmethylsulfinyl)-5,5-dimethyl-2-isoxazoline as a transparent viscous substance.
$^1$H-NMR [CDCl$_3$/TMS, δ (ppm)]:
7.63-7.60 (2H, m), 7.48-7.37 (3H, m), 4.29 (2H, q), 3.91 (3H, s), 3.12 (1H, d), 2.79 (1H, d), 1.41 (3H, s), 1.35 (3H, s)

Preparation Example 4

Production of 5,5-dimethyl-3-(5-fluoro-1-phenyl-3-trifluoromethyl-1H-pyrazol-4-ylmethylthio)-2-isoxazoline (Present Compound No. 3-0021)

9.3 g of sodium hydrosulfide hydrate (purity: 70%, 116.3 mmoles) was added to a solution of 18.7 g (105.7 mmoles) of 5,5-dimethyl-3-methylsulfonyl-2-isoxazoline (present compound No. 2-1) dissolved in 300 ml of N,N-dimethylformamide. The mixture was stirred for 2 hours. The reaction system was ice-cooled. Thereto was added a solution of 30.3 g (93.8 mmoles) of 4-bromomethyl-5-fluoro-1-phenyl-3-trifluoromethyl-1H-pyrazole dissolved in 200 ml of N,N-dimethylformamide. The mixture was stirred at 0° C. for 30 minutes to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 13.11 g (yield: 37.4%) of 5,5-dimethyl-3-(5-fluoro-1-phenyl-3-trifluoromethyl-1H-pyrazol-4-ylmethylthio)-2-isoxazoline as a yellow oily substance.

$^1$H-NMR [CDCl$_3$/TMS, δ (ppm)]:
7.65-7.39 (5H, m), 4.24 (2H, s), 2.81 (2H, s), 1.43 (6H, s)

Preparation Example 5

Production of 5,5-dimethyl-3-(5-ethylthio-1-phenyl-3-trifluoromethyl-1H-pyrazol-4-ylmethylthio)-2-isoxazoline (Present Compound No. 3-0022)

0.2 g (4.0 mmoles) of sodium hydroxide and 1 ml of water were added to a solution of 0.25 g (4.0 mmoles) of ethanethiol dissolved in 10 ml of N,N-dimethylformamide. The mixture was stirred at room temperature for 30 minutes. Thereto was added a solution of 0.5 g (1.4 mmoles) of 5,5-dimethyl-3-(5-fluoro-1-phenyl-3-trifluoromethyl-1H-pyrazol-4-ylmethylthio)-2-isoxazoline dissolved in 5 ml of N,N-dimethylformamide. The resulting mixture was stirred for 1 hour to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 0.6 g (yield: 100%) of 5,5-dimethyl-3-(5-ethylthio-1-phenyl-3-trifluoromethyl-1H-pyrazol-4-ylmethylthio)-2-isoxazoline.

$^1$H-NMR [CDCl$_3$/TMS, δ (ppm)]:
7.62-7.47 (5H, m), 4.44 (2H, s), 2.83 (2H, s), 2.50 (2H, q), 1.45 (6H, s), 1.02 (3H, t)

Preparation Example 6

Production of 5,5-dimethyl-3-(5-ethylsulfonyl-1-phenyl-3-trifluoromethyl-1H-pyrazol-4-ylmethylsulfonyl)-2-isoxazoline (Present Compound No. 3-0004)

1.7 g of m-chloroperbenzoic acid (purity: 70%, 6.7 mmoles) was added, with ice-cooling, to a solution of 0.6 g (1.3 mmoles) of 5,5-dimethyl-3-(5-ethylthio-1-phenyl-3-trifluoromethyl-1H-pyrazol-4-ylmethylthio)-2-isoxazoline dissolved in 10 ml of chloroform. The mixture was stirred at room temperature for 16 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 0.6 g (yield: 93.0%) of 5,5-dimethyl-3-(5-ethylsulfonyl-1-phenyl-3-trifluoromethyl-1H-pyrazol-4-ylmethylsulfonyl)-2-isoxazoline as light yellow crystals (melting point: 158 to 160° C.).

$^1$H-NMR [CDCl$_3$/TMS, δ (ppm)]:
7.58-7.54 (5H, m), 5.16 (2H, s), 3.18 (2H, s), 3.15 (2H, q), 1.55 (6H, s), 1.24 (3H, t)

Preparation Example 7

Production of 5,5-dimethyl-3-(5-dimethylamino-1-phenyl-3-trifluoromethyl-1H-pyrazol-4-ylmethylthio)-2-isoxazoline (Present Compound 3-0023)

0.8 g (6.7 mmoles) of a 40% aqueous dimethylamine solution was added to a solution of 0.5 g (1.3 mmoles) of 5,5-dimethyl-3-(5-fluoro-1-phenyl-3-trifluoromethyl-1H-pyrazol-4-ylmethylthio)-2-isoxazoline dissolved in 10 ml of N,N-dimethylformamide. The mixture was stirred at 100° C. for 9 hours in a sealed tube. Thereto was added 3.0 g (26.6 mmoles) of a 40% aqueous dimethylamine solution, and the resulting mixture was stirred for 9 hours to give rise to a reaction. After the completion of the reaction, the reaction mixture was poured into water, followed by extraction with ethyl acetate. The resulting organic layer was washed with an aqueous sodium chloride solution and then dried over anhydrous sodium sulfate. The resulting solution was subjected to vacuum distillation to remove the solvent contained therein. The residue was purified by silica gel column chromatography (developing solvent: hexane-ethyl acetate mixed solvent) to obtain 0.4 g (yield: 80.6%) of 5,5-dimethyl-3-(5-dimethylamino-1-phenyl-3-trifluoromethyl-1H-pyrazol-4-ylmethylthio)-2-isoxazoline.

$^1$H-NMR [CDCl$_3$/TMS, δ (ppm)]:
7.58-7.38 (5H, m), 4.35 (2H, s), 2.82 (2H, s), 2.77 (6H, s), 1.45 (6H, s)

Preparation Example 8

Production of 5,5-dimethyl-3-(5-dimethylamino-1-phenyl-3-trifluoromethyl-1H-pyrazol-4-ylmethylsulfonyl)-2-isoxazoline (Present Compound 3-0005)

0.7 g of m-chloroperbenzoic acid (purity: 70%, 2.7 mmoles) was added, with ice-cooling, to a solution of 0.4 g (1.1 mmoles) of 5,5-dimethyl-3-(5-dimethylamino-1-phenyl-3-trifluoromethyl-1H-pyrazol-4-ylmethylthio)-2-isoxazoline dissolved in 10 ml of chloroform. The mixture was stirred at room temperature for 20 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 0.2 g (yield: 52.0%) of 5,5-dimethyl-3-(5-dimethylamino-1-phenyl-3-trifluoromethyl-1H-pyrazol-4-ylmethylsulfonyl)-2-isoxazoline as a white powder (melting point: 150 to 151° C.).

$^1$H-NMR [CDCl$_3$/TMS, δ (ppm)]:
7.61-7.38 (5H, m), 4.75 (2H, s), 3.13 (2H, s), 2.76 (6H, s), 1.53 (6H, s)

Preparation Example 9

Production of 3-(1-tert-butyl-5-chloro-3-trifluoromethyl-1H-pyrazol-4-ylmethylthio)-5,5-dimethyl-2-isoxazoline (Present Compound No. 3-0006)

21.8 g of sodium hydrosulfide (purity: 70%, 272.5 mmoles) was added to a solution of 24.1 g (136.0 mmoles) of 5,5-dimethyl-3-methylsulfonyl-2-isoxazoline dissolved in 200 ml of N,N-dimethylformamide. The mixture was stirred for 1 hour. Thereto were added 18.8 g (136.2 mmoles) of anhydrous potassium carbonate and 21.0 g (136.2 mmoles) of Rongalit. The resulting mixture was stirred for 2 hours. Thereto was added, with ice-cooling, 40 g (125 mmoles) of 4-bromomethyl-1-tert-butyl-5-chloro-3-trifluoromethyl-1H-pyrazole. The resulting mixture was stirred at room temperature for 2 hours to give rise to a reaction. After the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 23.0 g (yield: 57.1%) of 3-(1-tert-butyl-5-chloro-3-trifluoromethyl-1H-pyrazol-4-ylmethylthio)-5,5-dimethyl-2-isoxazoline as light pink crystals (melting point: 79.0 to 81.0° C.).

$^1$H-NMR [CDCl$_3$/TMS, δ (ppm)]:
4.24 (2H, s), 2.80 (2H, s), 1.71 (9H, s), 1.43 (6H, s)

Preparation Example 10

Production of 3-(5-chloro-3-trifluoromethyl-1H-pyrazol-4-ylmethylthio)-5,5-dimethyl-2-isoxazoline (Present Compound No. 3-0007)

19.8 g (53.4 mmoles) of 3-(1-tert-butyl-5-chloro-3-trifluoromethyl-1H-pyrazol-4-ylmethylthio)-5,5-dimethyl-2-isoxazoline was added to 170 ml of a 25% hydrogen bromide-acetic acid solution. The mixture was stirred at 40 to 50° C. for 2 hours to give rise to a reaction. After the completion of the reaction was confirmed, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 12.0 g (yield: 60.6%) of 3-(5-chloro-3-trifluoromethyl-1H-pyrazol-4-ylmethylthio)-5,5-dimethyl-2-isoxazoline as light yellow crystals (melting point: 120.0 to 122.0° C.).

$^1$H-NMR [CDCl$_3$/TMS, δ (ppm)]:
4.26 (2H, s), 2.81 (2H, s), 1.44 (6H, s)

Preparation Example 11

Production of 3-(5-chloro-1-difluoromethyl-3-trifluoromethyl-1H-pyrazol-4-ylmethylthio)-5,5-dimethyl-2-isoxazoline (Present Compound No. 3-0008) and 3-(3-chloro-1-difluoromethyl-5-trifluoromethyl-1H-pyrazol-4-ylmethylthio)-5,5-dimethyl-2-isoxazoline (Present Compound 3-0009)

3.1 g (22.5 mmoles) of anhydrous potassium carbonate was added to a solution of 2.3 g (7.3 mmoles) of 3-(5-chloro-3-trifluoromethyl-1H-pyrazol-4-ylmethylthio)-5,5-dimethyl-2-isoxazoline dissolved in 50 ml of N,N-dimethylformamide. Thereinto was blown chlorodifluoromethane. The resulting mixture was stirred at 130 to 140° C. for 3 hours to give rise to a reaction. After confirmation of the completion of the reaction, the reaction mixture was pored into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.69 g (yield: 25.8%) of 3-(5-chloro-1-difluoromethyl-3-trifluoromethyl-1H-pyrazol-4-ylmethylthio)-5,5-dimethyl-2-isoxazoline as light yellow crystals (melting point: 41.0 to 42.0° C.) and 0.54 g (yield: 20.2%) of 3-(3-chloro-1-difluoromethyl-5-trifluoromethyl-1H-pyrazol-4-ylmethylthio)-5,5-dimethyl-2-isoxazoline as a white powder (melting point: 89.0 to 90.0° C.).

3-(5-Chloro-1-difluoromethyl-3-trifluoromethyl-1H-pyrazol-4-ylmethylthio)-5,5-dimethyl-2-isoxazoline $^1$H-NMR [CDCl$_3$/TMS, δ (ppm)]:
7.22 (1H, t), 4.25 (2H, s), 2.80 (2H, s), 1.44 (6H, s)

3-(3-Chloro-1-difluoromethyl-5-trifluoromethyl-1H-pyrazol-4-ylmethylthio)-5,5-dimethyl-2-isoxazoline $^1$H-NMR [CDCl$_3$/TMS, δ (ppm)]:
7.19 (1H, t), 4.28 (2H, s), 2.80 (2H, s), 1.44 (6H, s)

Preparation Example 12

Production of 3-(5-chloro-1-difluoromethyl-3-trifluoromethyl-1H-pyrazol-4-ylmethylsulfonyl)-5,5-dimethyl-2-isoxazoline (Present Compound No. 3-0010)

1.4 g of m-chloroperbenzoic acid (purity: 70%, 8.1 mmoles) was added, with ice-cooling, to a solution of 0.69 g (1.9 mmoles) of 3-(5-chloro-1-difluoromethyl-3-trifluoromethyl-1H-pyrazol-4-ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.4 g (yield: 53.3%) of 3-(5-chloro-1-difluoromethyl-3-trifluoromethyl-1H-pyrazol-4-ylmethylsulfonyl)-5,5-dimethyl-2-isoxazoline as a white powder (melting point: 126.0 to 127.0° C.).

$^1$H-NMR [CDCl$_3$/TMS, δ (ppm)]:
7.26 (1H, t), 4.68 (2H, s), 3.11 (2H, s), 1.53 (6H, s)

Preparation Example 13

Production of 3-(3-chloro-1-difluoromethyl-5-trifluoromethyl-1H-pyrazol-4-ylmethylsulfonyl)-5,5-dimethyl-2-isoxazoline (Present Compound No. 3-0011)

1.1 g of m-chloroperbenzoic acid (purity: 70%, 6.4 mmoles) was added, with ice-cooling, to a solution of 0.54 g (1.5 mmoles) of 3-(3-chloro-1-difluoromethyl-5-trifluoromethyl-1H-pyrazol-4-ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.47 g (yield: 79.7%) of 3-(3-chloro-1-difluoromethyl-5-trifluoromethyl-1H-pyrazol-4-ylmethylsulfonyl)-5,5-dimethyl-2-isoxazoline as a white powder (melting point: 136.0 to 137.0° C.).

$^1$H-NMR [CDCl$_3$/TMS, δ (ppm)]:
7.23 (1H, t), 4.71 (2H, s), 3.11 (2H, s), 1.53 (6H, s)

Preparation Example 14

Production of 5,5-dimethyl-3-(3-methoxy-1-methyl-5-trifluoromethyl-1H-pyrazol-4-ylmethylthio)-2-isoxazoline (Present Compound No. 3-0024)

3.1 g of sodium hydrosulfide hydrate (purity: 70%, 22.0 mmoles) was added to a solution of 3.3 g (17.3 mmoles) of 5,5-dimethyl-3-ethylsulfonyl-2-isoxazoline dissolved in 10 ml of N,N-dimethylformamide. The mixture was stirred for 2 hours. Thereto were added 3.1 g (22.0 mmoles) of anhydrous potassium carbonate, 2.7 g (17.5 mmoles) of Rongalit and 4.0 g (17.5 mmoles) of 4-chloromethyl-3-methoxy-1-methyl-5-trifluoromethyl-1H-pyrazole. The resulting mixture was stirred at room temperature for 2 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.8 g (yield: 52.0%) of 5,5-dimethyl-3-(3-methoxy-1-methyl-5-trifluoromethyl-1H-pyrazol-4-ylmethylthio)-2-isoxazoline.

Preparation Example 15

Production of 5,5-dimethyl-3-(3-hydroxy-1-methyl-5-trifluoromethyl-1H-pyrazol-4-ylmethylthio)-2-isoxazoline (Present Compound No. 3-0025)

To 20 ml of a 25% hydrogen bromide acetic acid solution was added 3.3 g (10.6 mmoles) of 5,5-dimethyl-3-(3-methoxy-1-methyl-5-trifluoromethyl-1H-pyrazol-4-ylmethylthio)-2-isoxazoline. The mixture was stirred at 50° C. for 3 hours to give rise to a reaction. After the completion of the reaction, the reaction mixture was subjected to vacuum distillation to remove the solvent contained therein. The residue was poured into water. The resulting crystals were collected by filtration, washed with water and dried to obtain 3.1 g (yield: 96.0%) of intended 5,5-dimethyl-3-(3-hydroxy-1-methyl-5-trifluoromethyl-1H-pyrazol-4-ylmethylthio)-2-isoxazoline.

Preparation Example 16

Production of 5,5-dimethyl-3-(3-ethoxy-1-methyl-5-trifluoromethyl-1H-pyrazol-4-ylmethylthio)-2-isoxazoline (Present Compound No. 3-0026)

0.20 g (1.3 mmoles) of anhydrous potassium carbonate and 0.20 g (1.5 mmoles) of ethyl iodide were added to a solution of 0.30 g (1.0 mmoles) of 5,5-dimethyl-3-(3-hydroxy-1-methyl-5-trifluoromethyl-1H-pyrazol-4-ylmethylthio)-2-isoxazoline dissolved in 10 ml of N,N-dimethylformamide. The mixture was stirred at 50° C. for 3 hours to give rise to a reaction. After the completion of the reaction, the reaction mixture was poured into water, followed by extraction with ethyl acetate. The resulting-organic layer was washed with an aqueous sodium chloride solution and then dried over anhydrous magnesium sulfate. The resulting solution was subjected to vacuum distillation to remove the solvent contained therein, to obtain 0.30 g (yield: 92.0%) of intended 5,5-dimethyl-3-(3-ethoxy-1-methyl-5-trifluoromethyl-1H-pyrazol-4-ylmethylthio)-2-isoxazoline.

Preparation Example 17

Production of 5,5-dimethyl-3-(3-ethoxy-1-methyl-5-trifluoromethyl-1H-pyrazol-4-ylmethylsulfonyl)-2-isoxazoline (Present Compound No. 3-0012)

0.68 g of m-chloroperbenzoic acid (purity: 70%, 2.76 mmoles) was added, with ice-cooling, to a solution of 0.30 g (0.92 mmoles) of 5,5-dimethyl-3-(3-ethoxy-1-methyl-5-trifluoromethyl-1H-pyrazol-4-ylmethylthio)-2-isoxazoline dissolved in 10 ml of chloroform. The mixture was stirred at room temperature for 5 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 0.24 g (yield: 73.0%) of 5,5-dimethyl-3-(3-ethoxy-1-methyl-5-trifluoromethyl-1H-pyrazol-4-ylmethylsulfonyl)-2-isoxazoline as white crystals (melting point: 124 to 125° C.).

$^1$H-NMR [CDCl$_3$/TMS, δ (ppm)]:
4.50 (2H, s), 4.27 (2H, q), 3.86 (3H, s), 3.04 (2H, s), 1.49 (6H, s), 1.39 (3H, t)

Preparation Example 18

Production of 5,5-dimethyl-3-(5-fluoro-1-methyl-3-trifluoromethyl-1H-pyrazol-4-ylmethylthio)-2-isoxazoline (Present Compound No. 3-0027)

19.3 g of sodium hydrosulfide (purity: 70%, 344.6 mmoles) was added to a solution of 21.3 g (120.3 mmoles) of 5,5-dimethyl-3-methylsulfonyl-2-isoxazoline dissolved in 200 ml of N,N-dimethylformamide. The mixture was stirred for 1 hour. Thereto were added 16.7 g (121.0 mmoles) of anhydrous potassium carbonate and 18.6 g (120.7 mmoles) of Rongalit. The resulting mixture was stirred for 2 hours. Thereto was added, with ice-cooling, 31.4 g (120.3 mmoles) of 4-bromomethyl-5-fluoro-1-methyl-3-trifluoromethyl-1H-pyrazole. The resulting mixture was stirred at room temperature for 2 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 29.0 g (yield: 90.3%) of 5,5-dimethyl-3-(5-fluoro-1-methyl-3-trifluoromethyl-1H-pyrazol-4-ylmethylthio)-2-isoxazoline as a yellow oily substance.

$^1$H-NMR [CDCl$_3$/TMS, δ (ppm)]:
4.24 (2H, s), 3.90 (3H, s), 2.78 (2H, s), 1.42 (6H, s)

Preparation Example 19

Production of 5,5-dimethyl-3-(5-methoxy-1-methyl-3-trifluoromethyl-1H-pyrazol-4-ylmethylthio)-2-isoxazoline (Present Compound No. 3-0028)

0.77 g (4.0 mmoles) of sodium methoxide (a 28% methanol solution) was added to a solution of 0.5 g (1.6 mmoles) of 5,5-dimethyl-3-(5-fluoro-1-methyl-3-trifluoromethyl-1H-pyrazol-4-ylmethylthio)-2-isoxazoline dissolved in 20 ml of methanol. The mixture was stirred for 4 hours under refluxing, to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.5 g (yield: 96.7%) of 5,5-dimethyl-3-(5-methoxy-1-methyl-3-trifluoromethyl-1H-pyrazol-4-ylmethylthio)-2-isoxazoline as a yellow oily substance.

$^1$H-NMR [CDCl$_3$/TMS, δ (ppm)]:
4.26 (2H, s), 4.07 (3H, s), 3.72 (3H, s), 2.80 (2H, s), 1.43 (6H, s)

Preparation Example 20

Production of 5,5-dimethyl-3-(5-methoxy-1-methyl-3-trifluoromethyl-1H-pyrazol-4-ylmethylsulfonyl)-2-isoxazoline (Present Compound No. 3-0013)

1.3 g of m-chloroperbenzoic acid (purity: 70%, 7.5 mmoles) was added, with ice-cooling, to a solution of 0.5 g (1.5 mmoles) of 5,5-dimethyl-3-(5-methoxy-1-methyl-3-trifluoromethyl-1H-pyrazol-4-ylmethylthio)-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.31 g (yield: 58.2%) of 5,5-dimethyl-3-(5-methoxy-1-methyl-3-trifluoromethyl-1H-pyrazol-4-ylmethylsulfonyl)-2-isoxazoline as a white powder (melting point: 113.0 to 114.0° C.).

$^1$H-NMR [CDCl$_3$/TMS, δ (ppm)]:
4.60 (2H, s), 4.11 (3H, s), 3.79 (3H, s), 3.10 (2H, s), 1.51 (6H, s)

Preparation Example 21

Production of 3-(5-(2-chlorophenoxy)-1-methyl-3-trifluoromethyl-1H-pyrazol-4-ylmethylthio)-5,5-dimethyl-2-isoxazoline (Present Compound No. 3-0029)

0.2 g (8.3 mmoles) of sodium hydride (purity: 60%) was added, with ice-cooling, to a solution of 0.44 g (3.4 mmoles) of 2-chlorophenol dissolved in 30 ml of N,N-dimethylformamide. The mixture was stirred for 1 hour. Thereto was added 0.7 g (2.2 mmoles) of 5,5-dimethyl-3-(5-fluoro-1-methyl-3-trifluoromethyl-1H-pyrazol-4-ylmethylthio)-2-isoxazoline. The resulting mixture was stirred at 120 to 130° C. for 5 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.63 g (yield: 66.7%) of 3-(5-(2-chlorophenoxy)-1-methyl-3-trifluoromethyl-1H-pyrazol-4-ylmethylthio)-5,5-dimethyl-2-isoxazoline as a yellow oily substance.

Preparation Example 22

Production of 3-(5-(2-chlorophenoxy)-1-methyl-3-trifluoromethyl-1H-pyrazol-4-ylmethylsulfonyl)-5,5-dimethyl-2-isoxazoline (Present Compound No. 3-0014)

1.0 g of m-chloroperbenzoic acid (purity: 70%, 5.8 mmoles) was added, with ice-cooling, to a solution of 0.63 g (1.5 mmoles) of 3-(5-(2-chlorophenoxy)-1-methyl-3-trifluoromethyl-1H-pyrazol-4-ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.31 g (yield: 45.7%) of 3-(5-(2-chlorophenoxy)-1-methyl-3-trifluoromethyl-1H-pyrazol-4-ylmethylsulfonyl)-5,5-dimethyl-2-isoxazoline as a white powder (melting point: 67.0 to 70.0° C.).

$^1$H-NMR [CDCl$_3$/TMS, δ (ppm)]:
7.50-6.91 (4H, m), 4.45 (2H, s), 3.71 (3H, s), 3.03 (2H, s), 1.47 (6H, s)

Preparation Example 23

Production of 3-(5-cyclopentyloxy-1-methyl-3-trifluoromethyl-1H-pyrazol-4-ylmethylthio)-5,5-dimethyl-2-isoxazoline (Present Compound No. 3-0030)

To a solution of 0.43 g (1.6 mmoles) of triphenylphosphine dissolved in 10 ml of benzene were added 0.14 g (1.6 mmoles) of cyclopentanol, 0.5 g (1.6 mmoles) of 5,5-dimethyl-3-(5-hydroxy-1-methyl-3-trifluoromethyl-1H-pyrazol-4-ylmethylthio)-2-isoxazoline and 0.7 g (1.6 mmoles) of diethyl azodicarboxylate (a 40% toluene solution). The mixture was stirred at room temperature for 12 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting organic layer was subjected to vacuum distillation to remove the solvent contained therein. The residue was purified by silica gel column chromatography (developing solvent: hexane-ethyl acetate mixed solvent) to obtain 0.52 g (yield: 85.2%) of 3-(5-cyclopentyloxy-1-methyl-3-trifluoromethyl-1H-pyrazol-4-ylmethylthio)-5,5-dimethyl-2-isoxazoline as a colorless transparent oily substance.

Preparation Example 24

Production of 3-(5-cyclopentyloxy-1-methyl-3-trifluoromethyl-1H-pyrazol-4-ylmethylsulfonyl)-5,5-dimethyl-2-isoxazoline (Present Compound No. 3-0015)

0.85 g of m-chloroperbenzoic acid (purity: 70%, 4.9 mmoles) was added, with ice-cooling, to a solution of 0.52 g (1.4 mmoles) of 3-(5-(cyclopentyloxy-1-methyl-3-trifluoromethyl-1H-pyrazol-4-ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.2 g (yield: 35.5%) of 3-(5-cyclopentyloxy-1-methyl-3-trifluoromethyl-1H-pyrazol-4-ylmethylsulfonyl)-5,5-dimethyl-2-isoxazoline as a white powder (melting point: 113.0 to 114.0° C.).
$^1$H-NMR [CDCl$_3$/TMS, δ (ppm)]:
5.03 (1H, br), 4.60 (2H, s), 3.73 (3H, s), 3.05 (2H, s), 1.88-1.70 (8H, m), 1.50 (6H, s)

Preparation Example 25

Production of 3-(5-cyano-1-methyl-3-trifluoromethyl-1H-pyrazol-4-ylmethylthio)-5,5-dimethyl-2-isoxazoline (Present Compound No. 3-0031)

0.2 g (4.0 mmoles) of sodium cyanide was added to a solution of 0.5 g (1.6 mmoles) of 5,5-dimethyl-3-(5-fluoro-1-methyl-3-trifluoromethyl-1H-pyrazol-4-ylmethylthio)-2-isoxazoline dissolved in 30 ml of N,N-dimethylformamide. The mixture was stirred at 40° C. for 1 hour to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.9 g of crude 3-(5-cyano-1-methyl-3-trifluoromethyl-1H-pyrazol-4-ylmethylthio)-5,5-dimethyl-2-isoxazoline as a yellow oily substance.
$^1$H-NMR [CDCl$_3$/TMS, δ (ppm)]:
4.30 (2H, s), 4.08 (3H, s), 2.81 (2H, s), 1.43 (6H, s)

Preparation Example 26

Production of 3-(5-cyano-1-methyl-3-trifluoromethyl-1H-pyrazol-4-ylmethylsulfonyl)-5,5-dimethyl-2-isoxazoline (Present Compound No. 3-0016)

2.1 g of m-chloroperbenzoic acid (purity: 70%, 12.2 mmoles) was added, with ice-cooling, to a solution of 0.9 g of 3-(5-cyano-1-methyl-3-trifluoromethyl-1H-pyrazol-4-ylmethylthio)-5,5-dimethyl-2-isoxazoline (crude compound) dissolved in 50 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.43 g (yield: 76.4%) of 3-(5-cyano-1-methyl-3-trifluoromethyl-1H-pyrazol-4-ylmethylsulfonyl)-5,5-dimethyl-2-isoxazoline as a white powder (melting point: 105.0 to 108.0° C.).
$^1$H-NMR [CDCl$_3$/TMS, δ (ppm)]:
4.73 (2H, s), 4.16 (3H, s), 3.14 (2H, s), 1.53 (6H, s)

Preparation Example 27

Production of 3-(3,5-dichloro-1-ethyl-1H-pyrazol-4-ylmethylthio)-5,5-dimethyl-2-isoxazoline (Present Compound No. 3-0032)

0.6 g of sodium hydrosulfide (purity: 70%, 10.7 mmoles) was added to a solution of 0.7 g (3.7 mmoles) of 5,5-dimethyl-3-ethylsulfonyl-2-isoxazoline dissolved in 30 ml of N,N-dimethylformamide. The mixture was stirred for 1 hour. Thereto were added 0.51 g (3.7 mmoles) of anhydrous potassium carbonate and 0.56 g (3.6 mmoles) of Rongalit. The resulting mixture was stirred for 2 hours. Thereto was added, with ice-cooling, 0.9 g (3.5 mmoles) of 4-bromomethyl-3,5-dichloro-1-ethyl-1H-pyrazole. The resulting mixture was stirred at room temperature for 2 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.8 g (yield: 70.8%) of 3-(3,5-dichloro-1-ethyl-1H-pyrazol-4-ylmethylthio)-5,5-dimethyl-2-isoxazoline as a colorless transparent oily substance.
$^1$H-NMR [CDCl$_3$/TMS, δ (ppm)]:
4.14 (2H, s), 4.14 (2H, q), 2.81 (2H, s), 1.43 (6H, s), 1.42 (3H, t)

Preparation Example 28

Production of 3-(3,5-dichloro-1-ethyl-1H-pyrazol-4-ylmethylsulfonyl)-5,5-dimethyl-2-isoxazoline (Present Compound No. 3-0017)

2.0 g of m-chloroperbenzoic acid (purity: 70%, 11.6 mmoles) was added, with ice-cooling, to a solution of 0.8 g (2.6 mmoles) of 3-(3,5-dichloro-1-ethyl-1H-pyrazol-4-ylmethylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The resulting solid was washed with n-hexane to obtain 0.41 g (yield: 46.6%) of 3-(3,5-dichloro-1-ethyl-1H-pyrazol-4-yl-methylsulfonyl)-5,5-dimethyl-2-isoxazoline as a white powder (melting point: 105.0 to 107.0° C.).

$^1$H-NMR [CDCl$_3$/TMS, δ (ppm)]:
4.48 (2H, s), 4.19 (2H, q), 3.05 (2H, s), 1.51 (6H, s), 1.45 (3H, t)

Preparation Example 29

Production of 3-(5-chloro-3-difluoromethyl-1-methyl-1H-pyrazol-4-ylmethylthio)-5,5-dimethyl-2-isoxazoline (Present Compound No. 3-0020)

1.2 g of sodium hydrosulfide hydrate (purity: 70%, 15.0 mmoles) was added to a solution of 1.9 g (10.0 mmoles) of 5,5-dimethyl-3-ethylsulfonyl-2-isoxazoline dissolved in 30 ml of N,N-dimethylformamide. The mixture was stirred for 2 hours. Thereto were added 2.1 g (15.0 mmoles) of anhydrous potassium carbonate, 2.3 g (15.0 mmoles) of Rongalit and 2.6 g (10.0 mmoles) of 4-bromomethyl-5-chloro-3-difluoromethyl-1-methyl-1H-pyrazole. The resulting mixture was stirred at room temperature for 15 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.1 g (yield: 68.0%) of 3-(5-chloro-3-difluoromethyl-1-methyl-1H-pyrazol-4-ylmethylthio)-5,5-dimethyl-2-isoxazoline as a colorless viscous liquid ($n_D^{20}$=1.5183).

$^1$H-NMR [CDCl$_3$/TMS, δ (ppm)]:
6.70 (1H, t, J=54.2 Hz), 4.24 (2H, s), 3.86 (3H, s), 2.80 (2H, s), 1.42 (6H, s)

Preparation Example 30

Production of 3-(5-chloro-3-difluoromethyl-1-methyl-1H-pyrazol-4-ylmethylsulfonyl)-5,5-dimethyl-2-isoxazoline (Present Compound No. 3-0018)

3.6 g of m-chloroperbenzoic acid (purity: 70%, 14.5 mmoles) was added, with ice-cooling, to a solution of 1.8 g (5.8 mmoles) of 3-(5-chloro-3-difluoromethyl-1-methyl-1H-pyrazol-4-ylmethylthio)-5,5-dimethyl-2-isoxazoline dissolved in 15 ml of chloroform. The mixture was stirred at room temperature for 22 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 1.7 g (yield: 85.9%) of 3-(5-chloro-3-difluoromethyl-1-methyl-1H-pyrazol-4-ylmethylsulfonyl)-5,5-dimethyl-2-isoxazoline as white crystals (melting point: 78 to 79° C.).

$^1$H-NMR [CDCl$_3$/TMS, δ (ppm)]:
6.80 (1H, t, J=54.8 Hz), 4.60 (2H, s), 3.91 (3H, s), 3.08 (2H, s), 1.51 (6H, s)

Preparation Example 31

Production of 5,5-dimethyl-3-(5-methyl-3-trifluoromethylisoxazol-4-ylmethylthio)-2-isoxazoline (Present Compound No. 4-0003)

0.4 g of sodium hydrosulfide hydrate (purity: 70%, 4.6 mmoles) was added to a solution of 0.4 g (2.3 mmoles) of 5,5-dimethyl-3-methylsulfonyl-2-isoxazoline dissolved in 10 ml of N,N-dimethylformamide. The mixture was stirred for 2 hours. Thereto were added 0.3 g (2.3 mmoles) of potassium carbonate, 0.4 g (2.3 mmoles) of Rongalit and 0.5 g (1.8 mmoles) of 4-bromomethyl-5-methyl-3-trifluoromethylisoxazole. The resulting mixture was stirred at room temperature for 14 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.4 g (yield: 70.0%) of 5,5-dimethyl-3-(5-methyl-3-trifluoromethylisoxazol-4-ylmethylthio)-2-isoxazoline.

$^1$H-NMR [CDCl$_3$/TMS, δ (ppm)]:
4.11 (2H, s), 2.77 (2H, s), 2.54 (3H, s), 1.42 (6H, s)

Preparation Example 32

Production of 5,5-dimethyl-3-(5-methyl-3-trifluoromethylisoxazol-4-ylmethylsulfonyl)-2-isoxazoline (Present Compound No. 4-0001)

0.8 g of m-chloroperbenzoic acid (purity: 70%, 3.2 mmoles) was added, with ice-cooling, to a solution of 0.4 g (1.3 mmoles) of 5,5-dimethyl-3-(5-methyl-3-trifluoromethylisoxazol-4-ylmethylthio)-2-isoxazoline dissolved in 10 ml of chloroform. The mixture was stirred at room temperature for 4 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The resulting crystals were washed with hexane to obtain 0.4 g (yield: 95.0%) of 5,5-dimethyl-3-(5-methyl-3-trifluoromethylisoxazol-4-ylmethylsulfonyl)-2-isoxazoline as white crystals (melting point: 135 to 136° C.).

$^1$H-NMR [CDCl$_3$/TMS, δ (ppm)]:
4.54 (2H, s), 3.11 (2H, s), 2.61 (3H, s), 1.52 (6H, s)

Preparation Example 33

Production of [(5-chloro-3-methyl-isothiazol-4-yl)-methylthio]-5,5-dimethyl-2-isoxazoline (Present Compound No. 4-0004)

0.82 g of sodium hydrosulfide (purity: 70%, 10.00 mmoles) was added at the room temperature to a solution of 0.89 g (5.00 mmoles) of 5,5-dimethyl-3-methylsulfonyl-2-isoxazoline dissolved in 10 ml of N,N-dimethylformamide. The mixture was stirred for 2 hours. Thereto were added 0.70 g (5.00 mmoles) of anhydrous potassium carbonate, 0.78 g (5.00 mmoles) of Rongalit and 0.91 g (5.00 mmoles) of 5-chloro-4-chloromethyl-3-methylisothiazole. The resulting mixture was stirred at room temperature overnight to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography to obtain 1.38 g (yield: quantitative) of [(5-chloro-3-methyl-isothiazol-4-yl)-methylthio]-5,5-dimethyl-2-isoxazoline.

Preparation Example 34

Production of [(5-chloro-3-methyl-isothiazol-4-yl)-methylsulfonyl]-5,5-dimethyl-2-isoxazoline (Present Compound No. 4-0002)

2.96 g of m-chloroperbenzoic acid (purity: 70%, 12.00 mmoles) was added, with ice-cooling, to a solution of 1.38 g (5.00 mmoles) of [(5-chloro-3-methyl-isothiazol-4-yl)-methylthio]-5,5-dimethyl-2-isoxazoline dissolved in 20 ml of chloroform. The mixture was stirred for 1 hour and then at room temperature for overnight to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The reside was purified by silica gel column chromatography to obtain 0.65 g (yield: 47.0%) of [(5-chloro-3-methyl-isothiazol-4-yl)-methylsulfonyl]-5,5-dimethyl-2-isoxazoline as a light yellow powder (melting point: 113 to 114° C.).

$^1$H-NMR [CDCl$_3$/TMS, δ (ppm)]:
8.89 (1H, s), 4.67 (2H, s), 3.05 (2H, s), 2.59 (3H, s), 1.51 (6H, s)

Preparation Example 35

Production of 5,5-dimethyl-3-[2,5-dimethyl-4-(1-methoxyiminoethyl)-thiophen-3-ylmethylthio]-2-isoxazoline (Present Compound No. 2-0002)

0.57 g (6.8 mmoles) of O-methylhydroxylamine hydrochloride and 0.56 g (6.8 mmoles) of sodium acetate were added to a solution of 1.0 g (3.4 mmoles) of 3-(4-acetyl-2,5-dimethylthiophen-3-ylmethylthio)-5,5-dimethyl-2-isoxazoline dissolved in 50 ml of ethanol. The mixture was stirred for 5 hours under refluxing, to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.4 g (36.4%) of 5,5-dimethyl-3-[2,5-dimethyl-4-(1-methoxyiminoethyl)-thiophen-3-ylmethylthio]-2-isoxazoline as a yellow oily substance.

$^1$H-NMR [CDCl$_3$/TMS, δ (ppm)]:
4.21 (2H, s), 3.95 (3H, s), 2.76 (2H, s), 2.38 (3H, s), 2.34 (3H, s), 2.13 (3H, s), 1.42 (6H, s)

Preparation Example 36

Production of 5,5-dimethyl-3-[2,5-dimethyl-4-(1-methoxyiminoethyl)-thiophen-3-ylmethylsulfonyl]-2-isoxazoline (Present Compound No. 2-0001)

0.61 g of m-chloroperbenzoic acid (purity: 70%, 3.5 mmoles) was added, with ice-cooling, to a solution of 0.4 g (1.2 mmoles) of 5,5-dimethyl-3-[2,5-dimethyl-4-(1-methoxyiminoethyl)-thiophen-3-ylmethylthio]-2-isoxazoline dissolved in 30 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.35 g (80%) of 5,5-dimethyl-3-[2,5-dimethyl-4-(1-methoxyiminoethyl)-thiophen-3-ylmethylsulfonyl]-2-isoxazoline as white crystals (melting point: 95.0 to 96.0° C.).

$^1$H-NMR [CDCl$_3$/TMS, δ (ppm)]:
4.79 (2H, s), 3.95 (3H, s), 2.93 (2H, s), 2.42 (3H, s), 2.37 (3H, s), 2.17 (3H, s), 1.47 (6H, s)

Preparation Example 37

Production of 5,5-dimethyl-3-(4-trifluoromethyl-pyridin-3-ylmethylthio)-2-isoxazoline (Present Compound No. 7-0003)

0.26 g of sodium hydrosulfide (purity: 70%, 4.6 mmoles) was added to a solution of 0.3 g (1.6 mmoles) of 5,5-dimethyl-3-ethylsulfonyl-2-isoxazoline dissolved in 20 ml of N,N-dimethylformamide. The mixture was stirred for 1 hour. Thereto were added 0.22 g (1.6 mmoles) of anhydrous potassium carbonate and 0.25 g (1.6 mmoles) of Rongalit. The resulting mixture was stirred for 2 hours. Thereto was added, with ice-cooling, 0.3 g (1.3 mmoles) of 3-bromomethyl-4-trifluoromethyl-pyridine. The resulting mixture was stirred at room temperature for 2 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.45 g (yield: 98.9%) of 5,5-dimethyl-3-(4-trifluoromethyl-pyridin-3-ylmethylthio)-2-isoxazoline as a yellow oily substance.

$^1$H-NMR [CDCl$_3$/TMS, δ (ppm)]:
8.98 (1H, s), 8.70 (1H, d), 7.51 (1H, d), 4.47 (2H, s), 2.79 (2H, s), 1.43 (6H, s)

Preparation Example 38

Production of 5,5-dimethyl-3-(4-trifluoromethyl-pyridin-3-ylmethylsulfonyl)-2-isoxazoline (Present Compound No. 7-0001) and 5,5-dimethyl-3-(4-trifluoromethyl-pyridine-N-oxide-3-ylmethylsulfonyl)-2-isoxazoline (Present Compound No. 7-0002)

0.77 g of m-chloroperbenzoic acid (purity: 70%, 4.5 mmoles) was added, with ice-cooling, to a solution of 0.45 g (1.6 mmoles) of 5,5-dimethyl-3-(4-trifluoromethyl-pyridin-3-ylmethylthio)-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.06 g (yield: 12.0%) of 5,5-dimethyl-3-(4-trifluoromethyl-pyridin-3-ylmethylsulfonyl)-2-isoxazoline as light yellow crystals (melting point: 77.0 to 80.0° C.) and 0.12 g (yield: 23.1%) of 5,5-dimethyl-3-(4-trifluoromethyl-pyridin-N-oxide-3-ylmethylsulfonyl)-2-isoxazoline as white crystals (melting point: 114.0 to 116.0° C.).

5,5-Dimethyl-3-(4-trifluoromethyl-pyridin-3-ylmethylsulfonyl)-2-isoxazoline $^1$H-NMR [CDCl$_3$/TMS, δ (ppm)]:
8.98 (1H, s), 8.84 (1H, d), 7.64 (1H, d), 4.92 (2H, s), 3.09 (2H, s), 1.52 (6H, s)

5,5-Dimethyl-3-(4-trifluoromethyl-pyridin-N-oxide-3-ylmethylsulfonyl)-2-isoxazoline $^1$H-NMR [CDCl$_3$/TMS, δ (ppm)]:
8.50 (1H, s), 8.25 (1H, d), 7.59 (1H, d), 4.81 (2H, s), 3.12 (2H, s), 1.53 (6H, s)

Preparation Example 39

Production of 5,5-dimethyl-[(4-methoxy-6-trifluoromethylpyrimidin-5-yl)-methylthio]-2-isoxazoline (Present Compound No. 8-0002)

0.32 g of sodium hydrosulfide (purity: 70%, 4.00 mmoles) was added, at room temperature, to a solution of 0.35 g (2.00 mmoles) of 5,5-dimethyl-3-methylsulfonyl-2-isoxazoline dissolved in 10 ml of dimethylformamide. The mixture was stirred for 2 hours. To the reaction mixture were added 0.28 g (2.00 mmoles) of anhydrous potassium carbonate, 0.31 g (2.00 mmoles) of Rongalit and 0.45 g (2.00 mmoles) of 5-chloromethyl-4-methoxy-6-trifluoromethylpyrimidine. The resulting mixture was stirred at room temperature for 2 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography to obtain 0.55 g (yield: 85.9%) of 5,5-dimethyl-[(4-methoxy-6-trifluoromethylpyrimidin-5-yl)-methylthio]-2-isoxazoline.

$^1$H-NMR [CDCl$_3$/TMS, δ (ppm)]:
8.81 (1H, s), 4.44 (2H, d), 4.12 (3H, s), 2.81 (2H, s), 1.45 (6H, s)

Preparation Example 40

Production of 5,5-dimethyl-[(4-methoxy-6-trifluoromethylpyrimidin-5-yl)-methylsulfonyl]-2-isoxazoline (Present Compound No. 8-0001)

1.05 g of m-chloroperbenzoic acid (purity: 70%, 4.28 mmoles) was added, with ice-cooling, to a solution of 0.55 g (1.71 mmoles) of 5,5-dimethyl-[(4-methoxy-6-trifluoromethylpyrimidin-5-yl)-methylthio]-2-isoxazoline dissolved in 20 ml of chloroform. The mixture was stirred for 1 hour and then at room temperature for 4 hours to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution and an aqueous sodium chloride solution in this order and then dried over anhydrous magnesium sulfate. The resulting solution was subjected to vacuum distillation to remove the solvent contained therein. The residue was purified by silica gel column chromatography to obtain 0.45 g (yield: 75.0%) of 5,5-dimethyl-[(4-methoxy-6-trifluoromethylpyrimidin-5-yl)-methylsulfonyl]-2-isoxazoline as white feather-like crystals (melting point: 175 to 176° C.).

$^1$H-NMR [CDCl$_3$/TMS, δ (ppm)]:
8.89 (1H, s), 5.00 (2H, d), 4.11 (3H, s), 3.11 (2H, s), 1.53 (6H, s)

Preparation Example 41

Production of 3-(5,5-dimethyl-2-isoxazolin-3-ylthiomethyl)-2-trifluoromethyl-6,7-dihydro-5H-pyrazolo[5,1-b][1,3]oxazine (Present Compound No. 3-0033)

A solution of 0.82 g (2.3 mmoles) of 3-[5-chloro-1-(3-hydroxypropyl)-3-trifluoromethyl-1H-pyrazol-4-ylmethylthio]-5,5-dimethyl-2-isoxazole dissolved in 5 ml of N,N-dimethylformamide was dropwise added to a suspension of 0.11 g (2.8 mmoles) of sodium hydride in 15 ml of N,N-dimethylformamide. After the completion of the dropwise addition, the resulting mixture was stirred at room temperature for 30 minutes, then heated to 100° C., and stirred for 1 hour to give rise to a reaction. After confirmation of the completion of the reaction, the reaction mixture was poured into water, followed by extraction with ethyl acetate. The resulting organic layer was washed with an aqueous citric acid solution and an aqueous sodium chloride solution, and then dried over magnesium sulfate. The resulting solution was subjected to vacuum distillation to obtain 0.77 g (yield: 100%) of 3-(5,5-dimethyl-2-isoxazolin-3-ylthiomethyl)-2-trifluoromethyl-6,7-dihydro-5H-pyrazolo[5,1-b][1,3]oxazine.

$^1$H-NMR [CDCl$_3$/TMS, δ (ppm)]:
4.37 (2H, t), 4.19 (2H, t), 4.15 (2H, s), 2.80 (2H, s), 2.31 (2H, m), 1.42 (6H, s)

Preparation Example 42

Production of 3-(5,5-dimethyl-2-isoxazolin-3-ylsulfonylmethyl)-2-trifluoromethyl-6,7-dihydro-5H-pyrazolo[5,1-b][1,3]oxazine (Present Compound No. 3-0019)

1.25 g of m-chloroperbenzoic acid (purity: 70%, 5.1 mmoles) was added, with ice-cooling, to a solution of 0.77 g (2.3 mmoles) of 3-(6,7-dihydro-3-trifluoromethyl-5H-pyrazolo[5,1-b][1,3]oxazin-4-yl-methylthio)-5,5-dimethyl-2-isoxazoline dissolved in 20 ml of chloroform. The mixture was stirred for 1 hour and then at room temperature for 12 hours to give rise to a reaction. After confirmation of the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography to obtain 0.36 g (yield: 43%) of 3-(5,5-dimethyl-2-isoxazolin-3-ylsulfonylmethyl)-2-trifluoromethyl-6,7-dihydro-5H-pyrazolo[5,1-b][1,3]oxazine as a white powder (melting point: 151.0 to 152.0° C.).

$^1$H-NMR [CDCl$_3$/TMS, δ (ppm)]:
4.47 (2H, s), 4.40 (2H, t), 4.23 (2H, t), 3.09 (2H, s), 2.34 (2H, m), 1.50 (6H, s)

Preparation Example 43

Production of 3-(5-chloro-1-methyl-3-trifluoromethylpyrazol-4-ylmethylthio)-5,5-dimethyl-2-isoxazoline (Present Compound No. 3-0186)

5.59 g of sodium hydrosulfide hydrate (purity: 70%, 69.8 mmoles) was added, at room temperature, to a solution of 6.84 g (35.8 mmoles) of 5,5-dimethyl-3-ethanesulfonyl-2-isoxazoline dissolved in 200 ml of N,N-dimethylformamide. The mixture was stirred for 1 hour. To the reaction mixture, were added 4.94 g (35.8 mmoles) of anhydrous potassium carbonate, 5.51 g (35.8 mmoles) of Rongalit and further 9.46 g (34.1 mmoles) of 4-bromomethyl-5-chloro-1-methyl-3-trifluoromethyl-1H-pyrazole. The resulting mixture was stirred at room temperature over one night to give rise to a reaction. After confirmation of the completion of the reaction, the reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 8.97 g (yield: 80.3%) of 3-(5-chloro-1-methyl-3-trifluoromethylpyrazol-4-ylmethylthio)-5,5-dimethyl-2-isoxazoline.

Preparation Example 44

Production of 3-(5-chloro-1-methyl-3-trifluoromethylpyrazol-4-ylmethanesulfonyl)-5,5-dimethyl-2-isoxazoline (Present Compound No. 3-0039)

16.87 g of m-chloroperbenzoic acid (purity: 70%, 68.4 mmoles) was added, with ice-cooling, to a solution of 8.97 g (27.4 mmoles) of 3-(5-chloro-1-methyl-3-trifluoromethylpyrazol-4-ylmethylthio)-5,5-dimethyl-2-isoxazoline dissolved in 300 ml of chloroform. The mixture was stirred for 1 hour and then at room temperature over one night to give rise to a reaction. After the completion of the reaction, the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The solid thus obtained was washed with n-hexane to obtain 9.36 g (yield: 95.1%) of 3-(5-chloro-1-methyl-3-trifluoromethylpyrazol-4-ylmethanesulfonyl)-5,5-dimethyl-2-isoxazoline as white powder (melting point: 115.0 to 116.0° C.).

$^1$H-NMR [CDCl$_3$/TMS, δ (ppm)]:
4.63 (2H, s), 3.95 (3H, s), 3.10 (2H, s), 1.52 (6H, s)

Preparation Example 45

Production of 3-(5-difluoromethoxy-1-methyl-3-trifluoromethyl-1H-pyrazol-4-ylmethylthio-5,5-dimethyl-2-isoxazoline (Present Compound No. 3-0187)

49.4 g (0.88 mol) of powdery potassium hydroxide and 0.94 g (2.9 mmol) of tetra-n-butylammonium bromide were added at room temperature to a solution of 90.3 g (0.29 mole) of 3-(5-hydroxy-1-methyl-3-trifluoromethyl-1H-pyrazol-4-ylmethylthio)-5,5-dimethyl-2-isoxazoline dissolved in 1000 ml of tetrahydrofuran. While cooling the system to 20° C. or lower, an excess amount of chlorodifluoromethane was introduced so as to have the system saturated. Thereafter, the reaction mixture was stirred at room temperature for 17 hours. After confirmation of the completion of the reaction, the reaction solution was poured into ice water, followed by extraction with ethyl acetate. The resulting organic layer was washed with water and a saturated aqueous sodium chloride solution in this order, and then dried over anhydrous magnesium sulfate. The resulting solution was subjected to vacuum distillation to remove the solvent contained therein. The residue was purified by silica gel chromatography to obtain 66.6 g (purity: 85%, yield; 54.0%) of 3-(5-difluoromethoxy-1-methyl-3-trifluoro-1H-pyrazol-4-ylmethylthio)-5,5-dimethyl-2-isoxazoline.

Preparation Example 46

Production of 3-(5-difluoromethoxy-1-methyl-3-trifluoromethyl-1H-pyrazol-4-ylmethanesulfonyl)-5,5-dimethyl-2-isoxazoline (Present Compound No. 3-0188)

157.6 g of m-chloroperbenzoic acid (purity: 70%, 0.64 mole) was added, with ice-cooling, to a solution of 56.5 g (0.16 mole) of 3-(5-difluoromethoxy-1-methyl-3-trifluoromethyl-1H-pyrazol-4-ylmethylthio)-5,5-dimethyl-2-isoxazoline dissolved in 1000 ml of chloroform. The mixture was stirred at room temperature for 4 hours to give rise to a reaction. After the completion of the reaction, the reaction solution was filtrated to remove insoluble matters. The filtrate thus obtained was poured into ice water, followed by extraction with chloroform. The resulting organic layer was washed with a 10% aqueous sodium hydroxide solution, water, an aqueous sodium hydrogensulfite solution, and a saturated aqueous sodium chloride solution in this order and then dried over anhydrous magnesium sulfate. The resulting solution was subjected to vacuum distillation to remove the solvent contained therein. The residue was washed with n-hexane to obtain 52.7 g (yield: 86.0%) of 3-(5-difluoromethoxy-1-methyl-3-trifluoromethyl-1H-pyrazol-4-ylmethanesulfonyl)-5,5-dimethyl-2-isoxazoline as white crystals (melting point: 129.0 to 130.0° C.).

$^1$H-NMR [CDCl$_3$/TMS, δ (ppm)]:

6.83 (1H, t, J=71.9 Hz), 4.60 (2H, s), 3.88 (3H, s), 3.11 (2H, s), 1.52 (6H, s)

Preparation Example 47

Production of 3-(5-difluoromethoxy-1-ethyl-3-trifluoromethyl-1H-pyrazol-4-ylmethylthio-5,5-dimethyl-2-isoxazoline (Present Compound No. 3-0189)

30.1 g (536.6 mmol) of powdery potassium hydroxide and 0.5 g of tetra-n-butylammonium bromide were added to a solution of 34.7 g (107.3 mmoles) of 3-(1-ethyl-5-hydroxy-3-trifluoromethyl-1H-pyrazol-4-ylmethylthio)-5,5-dimethyl-2-isoxazoline dissolved in 100 ml of dichloromethane. An excess amount of chlorodifluoromethane was introduced so as to have the system saturated. Thereafter, the reaction mixture was stirred for 3 hours. After confirmation of the completion of the reaction, the reaction solution was poured into water, followed by extraction with chloroform. The resulting organic layer was washed with water and a saturated aqueous sodium chloride solution in this order, and then dried over anhydrous magnesium sulfate. The resulting solution was subjected to vacuum distillation to remove the solvent contained therein. The residue was purified by silica gel chromatography to obtain 26.3 g (yield; 65.5%) of 3-(5-difluoromethoxy-1-ethyl-3-trifluoro-1H-pyrazol-4-ylmethylthio)-5,5-dimethyl-2-isoxazoline.

Preparation Example 48

Production of 3-(5-difluoromethoxy-1-ethyl-3-trifluoromethyl-1H-pyrazol-4-ylmethanesulfonyl)-5,5-dimethyl-2-isoxazoline (Present Compound No. 3-0190)

30.5 g of m-chloroperbenzoic acid (purity: 70%, 123.9 mmoles) was added, with ice-cooling, to a solution of 18.5 g (49.6 mmoles) of 3-(5-difluoromethoxy-1-ethyl-3-trifluoromethyl-1H-pyrazol-4-ylmethylthio)-5,5-dimethyl-2-isoxazoline dissolved in 200 ml of chloroform. The mixture was stirred at room temperature over one night to give rise to a reaction. After the completion of the reaction, the reaction solution was poured into water, followed by extraction with chloroform. The resulting organic layer was washed with an aqueous sodium hydrogensulfite solution, an aqueous sodium hydrogencarbonate solution, water, and an aqueous sodium chloride solution in this order and then dried over anhydrous magnesium sulfate. The resulting solution was subjected to vacuum distillation to remove the solvent contained therein. The residue was washed with n-hexane to obtain 19.3 g (yield: 96.0%) of 3-(5-difluoromethoxy-1-ethyl-3-trifluoromethyl-1H-pyrazol-4-ylmethanesulfonyl)-5,5-dimethyl-2-isoxazoline as white powder (melting point: 98 to 100° C.).

$^1$H-NMR [CDCl$_3$/TMS, δ (ppm)]:

6.83 (1H, t, J=72.0 Hz), 4.60 (2H, s), 4.19 (2H, q), 3.11 (2H, s), 1.52 (6H, s), 1.49 (3H, t)

Preparation Examples of Intermediates

Reference Example 1

Production of 3-chloro-5,5-dimethyl-2-isoxazoline 534.0 g (4.0 moles) of N-chlorosuccinimide was gradually added, at 65 to 70° C., to a solution of 182.7 g (2.05 moles) of glyoxylic acid aldoxime dissolved in 2 liters of 1,2-dimethoxyethane. The mixture was refluxed for 1 hour with heating. Thereto were added, with ice-cooling, 1,440.0 g (14.4 moles) of potassium hydrogencarbonate and 10 ml of water. Then, 360.0 g (6.4 moles) of 2-methylpropene was added. The resulting mixture was stirred at room temperature for 24 hours to give rise to a reaction. The reaction mixture was poured into water, followed by extraction with diisopropyl ether. The resulting organic layer was washed with water and an aqueous sodium chloride solution in this order and then dried over anhydrous magnesium sulfate. The resulting solution was subjected to vacuum distillation to remove the solvent contained therein, to obtain 107.7 g (yield: 40.0%) of 3-chloro-5,5-dimethyl-2-isoxazoline as a yellow viscous liquid.

$^1$H-NMR [CDCl$_3$/TMS, δ (ppm)]:

2.93 (2H, s), 1.47 (6H, s)

Reference Example 2

Production of 3-chloro-5-ethyl-5-methyl-2-isoxazoline 61.9 g (463.4 mmoles) of N-chlorosuccinimide was gradually added, at 60° C., to a solution of 20.6 g (231.7 mmoles) of glyoxylic acid aldoxime dissolved in 500 ml of 1,2-dimethoxyethane. After the addition, the mixture was refluxed for 10 minutes with heating. Thereto were added, with ice-cooling, 50 ml (463.4 mmoles) of 2-methyl-1-butene, 98.9 g (1,622 mmoles) of potassium hydrogencarbonate and 10 ml of water. The resulting mixture was stirred for 12 hours to give rise to a reaction. The reaction mixture was poured into water, followed by extraction with n-hexane. The resulting organic layer was washed with water and an aqueous sodium chloride solution in this order and then dried over anhydrous magnesium sulfate. The resulting solution was subjected to vacuum distillation to remove the solvent contained therein, to obtain 13.9 g (yield: 40.6%) of 3-chloro-5-ethyl-5-methyl-2-isoxazoline as a yellow viscous liquid.

$^1$H-NMR [CDCl$_3$/TMS, δ (ppm)]:

2.91 (2H, ABq, J=17.0, Δv=46.1 Hz), 1.73 (2H, q), 1.42 (3H, s), 0.96 (3H, t)

Reference Example 3

Production of 3-benzylthio-5,5-dimethyl-2-isoxazoline 3.2 g (23.2 mmoles) of anhydrous potassium carbonate and 3.0 g (22.5 mmoles) of 3-chloro-5,5-dimethyl-2-isoxazoline were added, in a nitrogen atmosphere, to a solution of 2.8 g (22.5 mmoles) of benzylmercaptan dissolved in 50 ml of N,N-dimethylformamide. The mixture was stirred at 100° C. for 2 hours to give rise to a reaction. After the completion of the reaction, the reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 3.1 g (yield: 62.0%) of 3-benzylthio-5,5-dimethyl-2-isoxazoline as a yellow oily substance ($n_D^{20}$=1.5521).

$^1$H-NMR [CDCl$_3$/TMS, δ (ppm)]:
7.24-7.39 (5H, m), 4.26 (2H, s), 2.77 (2H, s), 1.40 (6H, s)

Reference Example 4

Production of 3-(2,6-difluorobenzylsulfinyl)-5-ethyl-5-methyl-2-isoxazoline 4.6 g of m-chloroperbenzoic acid (purity: 70%, 18.8 mmoles) was added, with ice-cooling, to a solution of 4.1 g (15.0 mmoles) of 3-(2,6-difluorobenzylthio)-5-ethyl-5-methyl-2-isoxazoline dissolved in 50 ml of chloroform. The mixture was stirred for 1 hour and then at room temperature for 12 hours to give rise to a reaction. After the completion of the reaction the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 1.5 g (yield: 34.8%) of 3-(2,6-difluorobenzylsulfinyl)-5-ethyl-5-methyl-2-isoxazoline as a white powder (melting point: 30° C. or less).

$^1$H-NMR [CDCl$_3$/TMS, δ (ppm)]:
7.39-7.28 (1H, m), 7.03-6.94 (2H, m), 4.38 (2H, s), 3.04 (1H, ABq, J=17.2, Δv=85.7 Hz), 3.12 (1H, s), 1.75 (2H, m), 1.44 (3H, S)+1.41 (3H, s), 0.97 (3H, m)

Reference Example 5

Production of 3-(2,6-difluorobenzylsulfonyl)-5-ethyl-5-methyl-2-isoxazoline 1.0 g of m-chloroperbenzoic acid (purity: 70%, 4.1 mmoles) was added, with ice-cooling, to a solution of 0.8 g (2.8 mmoles) of 3-(2,6-difluorobenzylsulfinyl)-5-ethyl-5-methyl-2-isoxazoline dissolved in 50 ml of chloroform. The mixture was stirred for 1 hour and then at room temperature for 12 hours to give rise to a reaction. After the completion of the reaction. the reaction mixture was poured into water, followed by extraction with chloroform. The resulting organic layer was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.6 g (yield: 75.0%) of 3-(2,6-difluorobenzylsulfonyl)-5-ethyl-5-methyl-2-isoxazoline as a white powder (melting point: 64 to 65° C.).

$^1$H-NMR [CDCl$_3$/TMS, δ (ppm)]:
7.36-7.46 (1H, m), 6.98-7.04 (2H, m), 4.73 (2H, s), 3.04 (2H, ABq, J=17.2, Δv=51.1 Hz), 1.77 (2H, q), 1.46 (3H, s), 0.97 (3H, t)

Reference Example 6

Production of 5,5-dimethyl-3-methylsulfonyl-2-isoxazoline 1.0 kg of an aqueous sodium methanethiolate solution (content: 15%, 2.14 mmoles) was dropwise added, with ice-cooling, to a solution of 143.0 g (1.07 moles) of 3-chloro-5,5-dimethyl-2-isoxazoline dissolved in 500 ml of N,N-dimethylformamide. The mixture was stirred at room temperature for 12 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 115.0 g (yield: 74.1%) of 5,5-dimethyl-3-methylthio-2-isoxazoline. This residue (741.2 mmoles) was dissolved in 1 liter of chloroform. Thereto was added, with ice-cooling, 392.0 g of m-chloroperbenzoic acid (purity: 70%, 1.59 moles). The resulting mixture was stirred for 1 hour and then at room temperature for 12 hours to give rise to a reaction. After the completion of the reaction, the separated m-chloroperbenzoic acid was removed by filtration. The resulting filtrate was washed with an aqueous sodium hydrogensulfite solution, water, an aqueous sodium hydrogencarbonate solution and an aqueous sodium chloride solution in this order and then dried over anhydrous magnesium sulfate. The resulting solution was subjected to vacuum distillation to remove the solvent contained therein. The residue was washed with diisopropyl ether to obtain 77.6 g (yield: 59.1%) of 5,5-dimethyl-3-methylsulfonyl-2-isoxazoline as a white powder (melting point: 82 to 84° C.).

$^1$H-NMR [CDCl$_3$/TMS, δ (ppm)]:
3.26 (3H, s), 3.12 (2H, s), 1.51 (6H, s)

Reference Example 7

Production of 5,5-dimethyl-3-ethylthio-2-isoxazoline 1,500 ml of an aqueous solution containing 560.0 g (9.0 moles) of ethyl mercaptan and 360.0 g (9.0 moles) of sodium hydroxide was added to a solution containing 3-chloro-5,5-dimethyl-2-isoxazoline. The mixture was stirred at 60 to 70° C. for 16 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 270.0 g of crude 5,5-dimethyl-3-ethylthio-2-isoxazoline as a dark red oily substance.

Reference Example 8

Production of 5,5-dimethyl-3-ethylsulfonyl-2-isoxazoline 270.0 g (1.7 moles) of crude oily 5,5-dimethyl-3-ethylthio-2-isoxazoline was dissolved in 1.0 liter of chloroform. Thereto was added, with ice-cooling, 1,050 g of m-chloroperbenzoic acid (purity: 70%, 6.1 moles). The resulting mixture was stirred for 1 hour and then at room temperature for 12 hours to give rise to a reaction. After confirmation of the completion of the reaction, the separated m-chloroperbenzoic acid was removed by filtration. The resulting filtrate was washed with an aqueous sodium hydrogensulfite solution, an aqueous sodium hydrogencarbonate solution, water and an aqueous sodium chloride solution in this order and then dried over anhydrous magnesium sulfate. The resulting solution was subjected to vacuum distillation to remove the solvent contained therein. The residue was washed with n-hexane to obtain 133.6 g (yield: 65.4%) of 5,5-dimethyl-3-ethylsulfonyl-2-isoxazoline as a white powder.

Reference Example 9

Production of 1-phenyl-3-trifluoromethyl-1H-pyrazol-5-ol 20 g (184.9 mmoles) of phenylhydrazine and 4 ml of concentrated hydrochloric acid were added to a solution of 34.1 g (184.9 mmoles) of ethyl trifluoroacetoacetate dissolved in 500 ml of ethanol. The mixture was refluxed for 1 hour with heating, to give rise to a reaction. After the completion of the reaction, the reaction mixture was subjected to vacuum distillation to remove the most part of the solvent contained therein. The residue was mixed with water to precipitate crystals. The crystals were collected by filtration, washed with water until the filtrate became neutral, and dried to obtain 37.1 g (yield: 87.9%) of 1-phenyl-3-trifluoromethyl-1H-pyrazol-5-ol as ocherous crystals.
$^1$H-NMR [CDCl$_3$/TMS, δ (ppm)]:
7.68-7.41 (5H, m), 5.86 (1H, s), 3.71 (1H, s)

Reference Example 10

Production of 5-chloro-1-phenyl-3-trifluoromethyl-1H-pyrazole-4-carboaldehyde 33.6 g (219.1 mmoles) of phosphorus oxychloride was added to 7.7 g (105.2 mmoles) of N,N-dimethylformamide with ice-cooling. Thereto was added, at room temperature, 20 g (87.7 mmoles) of 1-phenyl-3-trifluoromethyl-1H-pyrazol-5-ol. The resulting mixture was refluxed for 1 hour with heating, to give rise to a reaction. After the completion of the reaction, the reaction mixture was poured into water with ice-cooling, followed by extraction with chloroform. The resulting organic layer was washed with an aqueous sodium hydrogencarbonate solution and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 19.1 g (yield: 79.1%) of 5-chloro-1-phenyl-3-trifluoromethyl-1H-pyrazole-4-carboaldehyde as white crystals.
$^1$H-NMR [CDCl$_3$/TMS, δ (ppm)]:
10.06 (1H, s), 7.57 (5H, s)

Reference Example 11

Production of (5-chloro-1-phenyl-3-trifluoromethyl-1H-pyrazol-4-yl)-methanol

A solution of 0.21 g (5.5 mmoles) of lithium aluminum hydride dissolved in 70 ml of THF was cooled to −30° C. Thereto was gradually added a solution of 3 g (10.9 mmoles) of 5-chloro-1-phenyl-3-trifluoromethyl-1H-pyrazole-4-carboaldehyde dissolved in 30 ml of tetrahydrofuran. The resulting mixture was stirred at −30° C. for 30 minutes to give rise to a reaction. After the completion of the reaction, ethyl acetate was added, followed by stirring. Then, water was added, followed by stirring for a while. The reaction mixture was filtered under vacuum. The filtrate was extracted with ethyl acetate. The resulting organic layer was washed with an aqueous sodium chloride solution and then dried over anhydrous magnesium sulfate. The resulting solution was subjected to vacuum distillation to remove the solvent contained therein, to obtain 3.0 g (yield: 99.9%) of (5-chloro-1-phenyl-3-trifluoromethyl-1H-pyrazol-4-yl)-methanol as white crystals.
$^1$H-NMR [CDCl$_3$/TMS, δ (ppm)]:
7.54-7.51 (5H, m), 4.71 (2H, d) 1.79 (1H, b)

Reference Example 12

Production of 4-bromomethyl-5-chloro-1-phenyl-3-trifluoromethyl-1H-pyrazole

A solution of 3.0 g (10.9 mmoles) of (5-chloro-1-phenyl-3-trifluoromethyl-1H-pyrazol-4-yl)-methanol dissolved in 60 ml of diethyl ether was cooled to −10° C. Thereto was added 1.0 g (3.8 mmoles) of phosphorus tribromide. The mixture was stirred at room temperature for 1 hour to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 3.6 g (yield: 95.8%) of 4-bromomethyl-5-chloro-1-phenyl-3-trifluoromethyl-1H-pyrazole as white crystals.
$^1$H-NMR [CDCl$_3$/TMS, δ (ppm)]:
7.58-7.48 (5H, m), 4.48 (2H, s)

Reference Example 13

Production of 5-fluoro-1-phenyl-3-trifluoromethyl-1H-pyrazole-4-carboaldehyde 10.5 g (180.2 mmoles) of potassium fluoride was added to a solution of 33.0 g (120.1 mmoles) of 5-chloro-1-phenyl-3-trifluoromethyl-1H-pyrazole-4-carboaldehyde dissolved in 500 ml of dimethyl sulfoxide. The mixture was stirred at 100° C. for 2 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 26.5 g (yield: 85.0%) of 5-fluoro-1-phenyl-3-trifluoromethyl-1H-pyrazole-4-carboaldehyde.
$^1$H-NMR [CDCl$_3$/TMS, δ (ppm)]:
9.96 (1H, s), 7.68-7.51 (5H, m)

Reference Example 14

Production of (5-fluoro-1-phenyl-3-trifluoromethyl-1H-pyrazol-4-yl)-methanol

To a solution of 1.6 g (41.0 mmoles) of sodium borohydride dissolved in 300 ml of methanol was added, with ice-cooling, a solution of 26.5 g (102.5 mmoles) of 5-fluoro-1-phenyl-3-trifluoromethyl-1H-pyrazole-4-carboaldehyde dissolved in 200 ml of methanol. The mixture was stirred at 0° C. for 30 minutes to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 28.5 g (yield: 100%) of (5-fluoro-1-phenyl-3-trifluoromethyl-1H-pyrazol-4-yl)-methanol.

$^1$H-NMR [CDCl$_3$/TMS, δ (ppm)]:
7.65-7.41 (5H, m), 4.68 (2H, d), 1.73 (1H, t)

Reference Example 15

Production of 4-bromomethyl-5-fluoro-1-phenyl-3-trifluoromethyl-1H-pyrazole

A solution of 27.5 g (105.7 mmoles) of (5-fluoro-1-phenyl-3-trifluoromethyl-1H-pyrazol-4-yl)-methanol dissolved in 300 ml of diethyl ether was cooled to 0° C. Thereto was added 10.0 g (37.0 mmoles) of phosphorus tribromide. The mixture was stirred at room temperature for 2 hours to give rise to a reaction. After the completion of the reaction, the reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 30.3 g (yield: 88.8%) of 4-bromomethyl-5-fluoro-1-phenyl-3-trifluoromethyl-1H-pyrazole.

$^1$H-NMR [CDCl$_3$/TMS, δ (ppm)]:
7.66-7.42 (5H, m), 4.44 (2H, s)

Reference Example 16

Production of 1-tert-butyl-3-trifluoromethyl-1H-pyrazol-5-ol 373.8 g (3.0 moles) of tert-butylhydrazine hydrochloride and 50 ml of concentrated hydrochloric acid were added to a solution of 552.3 g (3.0 moles) of ethyl trifluoroacetoacetate dissolved in 1,500 ml of ethanol. The mixture was refluxed for 2 days with heating, to give rise to a reaction. After the completion of the reaction, the reaction mixture was subjected to vacuum distillation to remove the most part of the solvent contained therein. The residue was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was washed with n-hexane to obtain 369.0 g (yield: 59.1%) of 1-tert-butyl-3-trifluoromethyl-1H-pyrazol-5-ol as a white powder.

Reference Example 17

Production of 1-tert-butyl-5-chloro-3-trifluoromethyl-1H-pyrazole-4-carboaldehyde 462.0 g (3.0 moles) of phosphorus oxychloride was added to 87.7 g (1.2 moles) of N,N-dimethylformamide with ice-cooling. Thereto was added, at room temperature, 208.2 g (1.0 moles) of 1-tert-butyl-3-trifluoromethyl-1H-pyrazol-5-ol. The resulting mixture was refluxed for 10 hours with heating, to give rise to a reaction. After the completion of the reaction, the reaction mixture was poured into water, followed by extraction with chloroform. The resulting organic layer was washed with water, a 5% aqueous sodium hydroxide solution and water in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 131.5 g (yield: 21.7%) of 1-tert-butyl-5-chloro-3-trifluoromethyl-1H-pyrazole-4-carboaldehyde as white crystals.

$^1$H-NMR [CDCl$_3$/TMS, δ (ppm)]:
9.97 (1H, d), 1.76 (9H, s)

Reference Example 18

Production of (1-tert-butyl-5-chloro-3-trifluoromethyl-1H-pyrazol-4-yl)-methanol A solution of 39.9 g (156.9 mmoles) of (1-tert-butyl-5-chloro-3-trifluoromethyl-1H-pyrazole-4-carboaldehyde dissolved in 300 ml of methanol was cooled to 0° C. Thereto was gradually added 6.5 g (172.6 mmoles) of sodium borohydride. The mixture was stirred at room temperature for 3 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 37.7 g (yield: 93.6%) of (1-tert-butyl-5-chloro-3-trifluoromethyl-1H-pyrazol-4-yl)-methanol.

$^1$H-NMR [CDCl$_3$/TMS, δ (ppm)]:
4.60 (2H, d), 1.72 (9H, s), 1.58 (1H, t)

Reference Example 19

Production of 4-bromomethyl-1-tert-butyl-5-chloro-3-trifluoromethyl-1H-pyrazole

A solution of 9.2 g (35.7 mmoles) of (1-tert-butyl-5-chloro-3-trifluoromethyl-1H-pyrazol-4-yl)-methanol dissolved in 100 ml of diethyl ether was cooled to −10° C. Thereto was added 11.6 g (42.9 mmoles) of phosphorus tribromide. The mixture was stirred at room temperature overnight to give rise to a reaction. After the completion of the reaction, the reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 10.0 g (yield: 87.3%) of 4-bromomethyl-1-tert-butyl-5-chloro-3-trifluoromethyl-1H-pyrazole.

Reference Example 20

Production of (1-tert-butyl-5-chloro-3-trifluoromethyl-1H-pyrazol-4-yl)-methanethiol 43.5 g (136.1 mmoles) of 4-bromomethyl-1-tert-butyl-5-chloro-3-trifluoromethyl-1H-pyrazole was added to a solution of 21.8 g of sodium hydrosulfide hydrate (purity: 70%, 272.2 mmoles) dissolved in 300 ml of N,N-dimethylformamide. The mixture was stirred at room temperature overnight to give rise to a reaction. After the completion of the reaction, the reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 32.3 g (yield: 87.0%) of (1-tert-butyl-5-chloro-3-trifluoromethyl-1H-pyrazol-4-yl)-methanethiol.

$^1$H-NMR [CDCl$_3$/TMS, δ (ppm)]:
3.65 (2H, d), 1.90 (1H, t), 1.70 (9H, s)

Reference Example 21

Production of 1-tert-butyl-5-methoxy-3-trifluoromethyl-1H-pyrazole 15.0 g (108.4 mmoles) of anhydrous potassium carbonate and 19.3 g (135.5 mmoles) of methyl iodide were added, at room temperature, to a solution of 18.8 g (90.3 mmoles) of 1-tert-butyl-3-trifluoromethyl-1H-pyrazol-5-ol dissolved in 100 ml of N,N-dimethylformamide. The mixture was stirred for 15 hours to give rise to a reaction. After the completion of the reaction, the reaction mixture was poured into water, followed by extraction with diethyl ether. The resulting organic layer was washed with water and an aqueous sodium chloride solution in this order and then dried over anhydrous magnesium sulfate. The resulting solution was subjected to vacuum distillation to remove the solvent contained therein, to obtain 20.0 g (yield: 99.8%) of 1-tert-butyl-5-methoxy-3-trifluoromethyl-1H-pyrazole.

Reference Example 22

Production of 1-tert-butyl-4-chloromethyl-5-methoxy-3-trifluoromethyl-1H-pyrazole 5.4 g of paraformaldehyde (180.2 mmoles in terms of formaldehyde) and 20 ml of concentrated hydrochloric acid were added to a solution of 20.0 g (90.1 mmoles) of 1-tert-butyl-5-methoxy-3-trifluoromethyl-1H-pyrazole dissolved in 90 ml of acetic acid. The mixture was stirred at 60° C. for 30 minutes to give rise to a reaction. After the completion of the reaction, the reaction mixture was poured into water, followed by extraction with diisopropyl ether. The resulting organic layer was washed with water and then dried over anhydrous magnesium sulfate. The resulting solution was subjected to vacuum distillation to remove the solvent contained therein, to obtain 21.7 g (yield: 89.0%) of 1-tert-butyl-4-chloromethyl-5-methoxy-3-trifluoromethyl-1H-pyrazole.

Reference Example 23

Production of 3-methoxy-1-methyl-5-trifluoromethyl-1H-pyrazole 10.0 g (72.3 mmoles) of anhydrous potassium carbonate and 12.8 g (90.3 mmoles) of methyl iodide were added, at room temperature, to a solution of 10.0 g (60.2 mmoles) of 3-hydroxy-1-methyl-5-trifluoromethyl-1H-pyrazole dissolved in 50 ml of N,N-dimethylformamide. The mixture was stirred for 15 hours to give rise to a reaction. After the completion of the reaction, the reaction mixture was poured into water, followed by extraction with diethyl ether. The resulting organic layer was washed with water and an aqueous sodium chloride solution in this order and then dried over anhydrous magnesium sulfate. The resulting solution was subjected to vacuum distillation to remove the solvent contained therein, to obtain 9.8 g (yield: 90.7%) of 3-methoxy-1-methyl-5-trifluoromethyl-1H-pyrazole.

Reference Example 24

Production of 4-chloromethyl-3-methoxy-1-methyl-5-trifluoromethyl-1H-pyrazole 0.45 g of paraformaldehyde (15.0 mmoles in terms of formaldehyde) and 5 ml of concentrated hydrochloric acid were added to a solution of 1.00 g (5.6 mmoles) of 3-methoxy-1-methyl-5-trifluoromethyl-1H-pyrazole dissolved in 25 ml of acetic acid. The mixture was stirred at 80° C. for 2 hours to give rise to a reaction. After the completion of the reaction, the reaction mixture was poured into water and neutralized with potassium carbonate, followed by extraction with ethyl acetate. The resulting organic layer was washed with water and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.83 g (yield: 65.0%) of 4-chloromethyl-3-methoxy-1-methyl-5-trifluoromethyl-1H-pyrazole.

Reference Example 25

Production of 5-fluoro-1-methyl-3-trifluoromethyl-1H-pyrazole-4-carboaldehyde 42.0 g (711.9 mmoles) of potassium fluoride was added to a solution of 60.4 g (282.7 mmoles) of 5-chloro-1-methyl-3-trifluoromethyl-1H-pyrazole-4-carboaldehyde dissolved in 700 ml of dimethyl sulfoxide. The mixture was stirred at 120 to 140° C. for 5 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 36.8 g (yield: 66.0%) of 5-fluoro-1-methyl-3-trifluoromethyl-1H-pyrazole-4-carboaldehyde.

Reference Example 26

Production of (5-fluoro-1-methyl-3-trifluoromethyl-1H-pyrazol-4-yl)-methanol

To a solution of 3.9 g (102.6 mmoles) of sodium borohydride dissolved in 500 ml of methanol was added, with ice-cooling, a solution of 36.8 g (187.6 mmoles) of 5-fluoro-1-methyl-3-trifluoromethyl-1H-pyrazole-4-carboaldehyde dissolved in 200 ml of methanol. The resulting mixture was stirred at 0° C. for 30 minutes to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 35.4 g (yield: 95.4%) of (5-fluoro-1-methyl-3-trifluoromethyl-1H-pyrazol-4-yl)-methanol.

Reference Example 27

Production of 4-bromomethyl-5-fluoro-1-methyl-3-trifluoromethyl-1H-pyrazole

A solution of 35.4 g (178.7 mmoles) of 5-fluoro-1-methyl-3-trifluoromethyl-1H-pyrazole-4-methanol dissolved in 500 ml of diethyl ether was cooled to −30° C. Thereto was added 54.0 g (199.5 mmoles) of phosphorus tribromide. The mixture was stirred at room temperature for 12 hours to give rise to a reaction. After confirmation of the completion of the reaction, the reaction mixture was poured into water, followed by extraction with diethyl ether. The resulting organic layer was washed with water and an aqueous sodium chloride solution and then dried over anhydrous magnesium sulfate. The resulting solution was subjected to vacuum distillation to remove the solvent contained therein, to obtain 31.4 g (yield: 80.8%) of 4-bromomethyl-5-fluoro-1-methyl-3-trifluoromethyl-1H-pyrazole.

Reference Example 28

Production of (ethoxycarbonyl)malondialdehyde 12.6 g of sodium hydride (purity: 60%, 525.0 mmoles) was washed with diethyl ether by decantation several times and then made into a solution in 500 ml of diethyl ether. Thereto were added, in a nitrogen current at 0 to 10° C., 194 g (2.6 moles) of ethyl formate and 50 g (262.0 mmoles) of ethyl 3,3-diethoxy-propionate. The resulting mixture was stirred at room temperature for 15 hours to give rise to a reaction. After confirmation of the completion of the reaction, the reaction mixture was poured into water, followed by washing with diethyl ether. The resulting aqueous layer was allowed to have a pH of 1 with hydrochloric acid, followed by extraction with dichloromethane. The resulting organic layer was washed with an aqueous sodium chloride solution and then dried over anhydrous magnesium sulfate. The resulting solution was subjected to vacuum distillation to remove the solvent contained therein, to obtain 37.6 g (yield: 100%) of crude (ethoxycarbonyl)malondialdehyde as a dark red oily substance.

$^1$H-NMR [CDCl$_3$/TMS, δ (ppm)]:
9.09 (2H, s), 5.26 (1H, s), 4.27 (2H, q), 1.28 (3H, t)

Reference Example 29

Production of ethyl 1H-pyrazole-4-carboxylate 6.2 g (193 mmoles) of hydrazine was added, with ice-cooling, to a solution of 27.6 g (192 mmoles) of (ethoxycarbonyl)malondialdehyde dissolved in 150 ml of ethanol. The mixture was stirred at room temperature for 17 hours to give rise to a reaction. The reaction mixture was subjected to vacuum distillation to remove the ethanol contained therein. The residue was purified by silica gel column chromatography (developing solvent: dichloromethane-ethyl acetate mixed solvent) to obtain 19.4 g (72.4%) of ethyl 1H-pyrazole-4-carboxylate as yellow crystals.

$^1$H-NMR [CDCl$_3$/TMS, δ (ppm)]:
8.08 (2H, s), 5.30 (1H, s), 4.31 (2H, q), 1.36 (3H, t)

Reference Example 30

Production of ethyl 1-ethyl-1H-pyrazole-4-carboxylate 3.7 g (26.8 mmoles) of anhydrous potassium carbonate and 4.2 g (26.6 mmoles) of ethyl iodide were added to a solution of 1.5 g (10.7 mmoles) of ethyl 1H-pyrazole-4-carboxylate dissolved in 50 ml of N,N-dimethylformamide. The mixture was stirred at room temperature for 20 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 1.6 g (yield: 88.9%) of ethyl 1-ethyl-1H-pyrazole-4-carboxylate as a yellow oily substance.

$^1$H-NMR [CDCl$_3$/TMS, δ (ppm)]:
7.90 (2H, s), 4.28 (2H, q), 4.18 (2H, q), 1.51 (3H, t), 1.35 (3H, t)

Reference Example 31

Production of ethyl 3,5-dichloro-1-ethyl-1H-pyrazole-4-carboxylate

In a glass sealed tube were placed 1.6 g (9.5 mmoles) of ethyl 1-ethyl-1H-pyrazole-4-carboxylate and 5.1 g (38.3 mmoles) of N-chlorosuccinimide. There were allowed to react at 160° C. for 6 hours. After the completion of the reaction, the reaction mixture was cooled to room temperature, washed with carbon tetrachloride and chloroform, and filtered under vacuum. The resulting filtrate (organic layer) was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 1.0 g (yield: 44.2%) of ethyl 3,5-dichloro-1-ethyl-1H-pyrazole-4-carboxylate as a yellow oily substance.

$^1$H-NMR [CDCl$_3$/TMS, δ (ppm)]:
4.36 (2H, q), 4.21 (2H, q), 1.44 (3H, t), 1.38 (3H, t)

Reference Example 32

Production of (3,5-dichloro-1-ethyl-1H-pyrazol-4-yl)methanol

A solution of 0.16 g (4.2 mmoles) of lithium aluminum hydride dissolved in 70 ml of tetrahydrofuran was cooled to −50° C. Thereto was gradually added dropwise a solution of 1.0 g (4.2 mmoles) of ethyl 3,5-dichloro-1-ethyl-1H-pyrazole-4-carboxylate dissolved in 30 ml of tetrahydrofuran. The mixture was stirred at −50° C. for 3 hours to give rise to a reaction. After confirmation of the completion of the reaction, ethyl acetate was added, followed by stirring for a while. Water was added, followed by stirring for a while. The resulting mixture was filtered under vacuum. The filtrate was extracted with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.82 g (yield: 100%) of (3,5-dichloro-1-ethyl-1H-pyrazol-4-yl)methanol as a brown oily substance.

$^1$H-NMR [CDCl$_3$/TMS, δ (ppm)]:
4.52 (2H, s), 4.16 (2H, q), 1.43 (3H, t)

Reference Example 33

Production of 4-bromomethyl-3,5-dichloro-1-ethyl-1H-pyrazole

A solution of 0.82 g (4.2 mmoles) of (3,5-dichloro-1-ethyl-1H-pyrazol-4-yl)methanol dissolved in 50 ml of diethyl ether was cooled to −30° C. Thereto was added 1.3 g (4.8 mmoles) of phosphorus tribromide. The mixture was stirred at room temperature for 12 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.9 g (yield: 81.8%) of 4-bromomethyl-3,5-dichloro-1-ethyl-1H-pyrazole as a yellow oily substance.

$^1$H-NMR [CDCl$_3$/TMS, δ (ppm)]:
4.33 (2H, s), 4.13 (2H, q), 1.43 (3H, t)

Reference Example 34

Production of 3-difluoromethyl-1-methyl-1H-pyrazol-5-ol 8.3 g (180.6 mmoles) of methylhydrazine and 5 ml of concentrated hydrochloric acid were added to a solution of 30.0 g (180.6 mmoles) of ethyl difluoroacetoacetate dissolved in 200 ml of ethanol. The mixture was refluxed for 2 days with heating, to give rise to a reaction. After the completion of the reaction, the reaction mixture was subjected to vacuum distillation to remove the most part of the solvent contained therein. The residue was poured into water. The mixture was allowed to have a pH of 4 using citric acid and extracted with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 8.9 g (yield: 33.3%) of 3-difluoromethyl-1-methyl-1H-pyrazol-5-ol.

Reference Example 35

Production of 5-chloro-3-difluoromethyl-1-methyl-1H-pyrazole-4-carboaldehyde 41.6 g (270.1 mmoles) of phosphorus oxychloride was added, with ice-cooling, to 7.9 g (108.0 mmoles) of N,N-dimethylformamide. Thereto was added, at room temperature, 8.0 g (54.0 mmoles) of 3-difluoromethyl-1-methyl-1H-pyrazol-5-ol. The mixture was refluxed for 4 hours with heating, to give rise to a reaction. After the completion of the reaction, the reaction mixture was poured into water, followed by extraction with chloroform. The resulting organic layer was washed with water, a 5% aqueous sodium hydroxide solution and water in this order and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 7.7 g (yield: 73.3%) of 5-chloro-3-difluoromethyl-1-methyl-1H-pyrazole-4-carboaldehyde as white crystals.

$^1$H-NMR [CDCl$_3$/TMS, δ (ppm)]:
9.96 (1H, s), 6.90 (1H, t, J=53.6 Hz), 3.93 (3H, s)

Reference Example 36

Production of (5-chloro-3-difluoromethyl-1-methyl-1H-pyrazol-4-yl)-methanol

A solution of 7.2 g (37.0 mmoles) of 5-chloro-3-difluoromethyl-1-methyl-1H-pyrazole-4-carboaldehyde dissolved in 100 ml of methanol was cooled to 0° C. Thereto was gradually added 2.1 g (55.5 mmoles) of sodium borohydride. The mixture was stirred at room temperature for 3 hours to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 3.8 g (yield: 52.1%) of (5-chloro-3-difluoromethyl-1-methyl-1H-pyrazol-4-yl)-methanol.

$^1$H-NMR [CDCl$_3$/TMS, δ (ppm)]:
6.70 (1H, t, J=40.8 Hz), 4.63 (2H, s), 3.86 (3H, s), 1.79 (1H, br)

Reference Example 37

Production of 4-bromomethyl-5-chloro-3-difluoromethyl-1-methyl-1H-pyrazole

A solution of 2.0 g (10.0 mmoles) of (5-chloro-3-difluoromethyl-1-methyl-1H-pyrazol-4-yl)-methanol dissolved in 50 ml of diethyl ether was cooled to −10° C. Thereto was added 1.0 g (3.5 mmoles) of phosphorus tribromide. The mixture was stirred at room temperature overnight to give rise to a reaction. After the completion of the reaction, the reaction mixture was poured into ice water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 2.6 g (yield: 100.0%) of 4-bromomethyl-5-chloro-3-difluoromethyl-1-methyl-1H-pyrazole.

Reference Example 38

Production of Trifluoroacetaldehyde Oxime Etherate 24.1 g (347.0 mmoles) of hydroxylamine hydrochloride and 160 ml of water were added to a solution of 50.0 g (347.0 mmoles) of trifluoroacetaldehyde hemiethyl acetal dissolved in 80 ml of methanol. Thereto was dropwise added, with ice-cooling, 80.0 g of a 50% aqueous sodium hydroxide solution (1.7 moles). After the completion of the dropwise addition, the resulting mixture was stirred at room temperature for 6 hours to give rise to a reaction. After the completion of the reaction, 10% hydrochloric acid was added for pH adjustment to 6. The resulting mixture was extracted with diethyl ether. The extract was subjected to vacuum distillation to remove the solvent contained therein. The residue was subjected to distillation to obtain 24.7 g (yield: 38.0%) of trifluoroacetaldehyde oxime etherate.

Reference Example 39

Production of Trifluoroacetohydroximoyl Bromide Etherate

A solution of 38.8 g (218.0 mmoles) of N-bromosuccinimide dissolved in 125 ml of N,N-dimethylformamide was added, with ice-cooling, to a solution of 24.7 g (131.7 mmoles) of trifluoroacetaldehyde oxime etherate dissolved in 50 ml of N,N-dimethylformamide. The mixture was stirred at room temperature for 3 hours to give rise to a reaction. After the completion of the reaction, the reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein. The residue was subjected to distillation to obtain 33.3 g (yield: 95.0%) of trifluoroacetohydroximoyl bromide etherate as a brown oily substance.
$^1$H-NMR [CDCl$_3$/TMS, δ (ppm)]:
9.30 (1H, s)

Reference Example 40

Production of 4-ethoxycarbonyl-5-methyl-3-trifluoromethylisoxazole 2.8 g (51.3 mmoles) of sodium methoxide was added to a solution of 6.7 g (51.3 mmoles) of ethyl acetoacetate dissolved in 80 ml of methanol. Thereto was added, with ice-cooling, a solution of 5.0 g (18.8 mmoles) of trifluorohydroximoyl bromide etherate dissolved in 20 ml of methanol. The resulting mixture was stirred at room temperature for 3 hours to give rise to a reaction. After the completion of the reaction, the reaction mixture was subjected to vacuum distillation to remove the solvent contained therein. Water was added to the residue, followed by extraction with chloroform. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.9 g (yield: 69.0%) of 4-ethoxycarbonyl-5-methyl-3-trifluoromethylisoxazole as a colorless oily substance.
$^1$H-NMR [CDCl$_3$/TMS, δ (ppm)]:
4.36 (2H, q), 2.77 (3H, s), 1.37 (3H, t)

Reference Example 41

Production of (5-methyl-3-trifluoromethylisoxazol-4-yl)-methanol

A solution of 0.16 g (4.2 mmoles) of lithium aluminum hydride dissolved in 15 ml of THF was cooled to 0° C. Thereto was gradually added a solution of 0.93 g (4.2 mmoles) of 4-ethoxycarbonyl-5-methyl-3-trifluoromethylisoxazole dissolved in 15 ml of THF. The mixture was stirred at 0° C. for 1 hour to give rise to a reaction. After the completion of the reaction, ethyl acetate was added, followed by stirring for a while. Water was added, followed by stirring for a while. The reaction mixture was filtered under vacuum. The filtrate was extracted with diethyl ether. The resulting organic layer was washed with an aqueous sodium chloride solution and then dried over anhydrous magnesium sulfate. The resulting solution was subjected to vacuum distillation to remove the solvent contained therein, to obtain 0.5 g (yield: 60.0%) of (5-methyl-3-trifluoromethylisoxazol-4-yl)-methanol.
$^1$H-NMR [CDCl$_3$/TMS, δ (ppm)]:
4.60 (2H, d), 2.54 (3H, s), 1.66 (1H, br)

Reference Example 42

Production of 4-bromomethyl-5-methyl-3-trifluoromethylisoxazole

A solution of 0.45 g (2.5 mmoles) of (5-methyl-3-trifluoromethylisoxazol-4-yl)-methanol dissolved in 10 ml of diethyl ether was cooed to 0° C. Thereto was added 0.2 g (8.9 mmoles) of phosphorus tribromide. The mixture was stirred at room temperature for 1 hour to give rise to a reaction. After the completion of the reaction, the reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain 0.5 g (yield: 74.0%) of 4-bromomethyl-5-methyl-3-trifluoromethylisoxazole.
$^1$H-NMR [CDCl$_3$/TMS, δ (ppm)]:
4.31 (2H, d), 2.51 (3H, s)

Reference Example 43

Production of (5-chloro-3-methyl-isothiazol-4-yl)-methanol

A solution of 2.06 g (10.0 mmoles) of ethyl 5-chloro-3-methyl-isothiazole-4-carboxylate dissolved in 10 ml of THF was dropwise added, at –30° C., to a solution of 0.42 g (11.0 mmoles) of lithium aluminum hydride dissolved in 10 ml of THF. The mixture was stirred at the same temperature for 1 hour to give rise to a reaction. After confirmation of the completion of the reaction, ethyl acetate was added to the reaction mixture. The resulting mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 1.50 g (yield: 91.5%) of (5-chloro-3-methyl-isothiazol-4-yl)-methanol.

Reference Example 44

Production of 4-chloromethyl-5-chloro-3-methylisothiazole 3.26 g (27.44 mmoles) of thionyl chloride was added, at room temperature, to a solution of 1.50 g (9.15 mmoles) of (5-chloro-3-methyl-isothiazol-4-yl)-methanol dissolved in 10 ml of chloroform. The mixture was stirred for 3 hours to give rise to a reaction. After confirmation of the completion of the reaction, the reaction mixture was subjected to vacuum distillation to remove the solvent contained therein, to obtain 1.67 g (yield: quantitative) of 4-chloromethyl-5-chloro-3-methylisothiazole.

Reference Example 45

Production of methyl 4-trifluoromethylnicotinate 6.7 g (48.6 mmoles) of anhydrous potassium carbonate and 6.9 g (48.6 mmoles) of methyl iodide were added to a solution of 4.6 g (24.1 mmoles) of 4-trifluoromethylnicotinic acid dissolved in 70 ml of N,N-dimethylformamide. The mixture was stirred at room temperature for 12 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 2.77 g (yield: 56.1%) of methyl 4-trifluoromethylnicotinate as a yellow oily substance.

$^1$H-NMR [CDCl$_3$/TMS, δ (ppm)]:
9.11 (1H, s), 8.92 (1H, d), 7.64 (1H, d), 3.99 (3H, s)

Reference Example 46

Production of (4-trifluoromethylpyridin-3-yl)-methanol

A solution of 0.37 g (9.7 mmoles) of lithium aluminum hydride dissolved in 100 ml of THF was cooled to −50° C. Thereto was gradually added dropwise a solution of 2.0 g (9.8 mmoles) of methyl 4-trifluoromethylnicotinate dissolved in 30 ml of THF. The mixture was stirred at −50° C. for 3 hours to give rise to a reaction. After confirmation of the completion of the reaction, ethyl acetate was added, followed by stirring for a while. Water was added, followed by stirring for a while. The reaction mixture was filtered under vacuum. The filtrate was extracted with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 0.6 g (yield: 35.3%) of (4-trifluoromethylpyridin-3-yl)-methanol as a yellow oily substance.

$^1$H-NMR [CDCl$_3$/TMS, δ (ppm)]:
9.00 (1H, s), 8.73 (1H, d), 7.51 (1H, d), 4.95 (2H, s)

Reference Example 47

Production of 3-bromomethyl-4-trifluoromethylpyridine

A solution of 0.6 g (3.4 mmoles) of (4-trifluoromethylpyridin-3-yl)-methanol dissolved in 50 ml of diethyl ether was cooed to −30° C. Thereto was added 1.4 g (5.2 mmoles) of phosphorus tribromide. The mixture was stirred at room temperature for 12 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein, to obtain 0.61 g (yield: 75.3%) of 3-bromomethyl-4-trifluoromethylpyridine as a yellow oily substance.

$^1$H-NMR [CDCl$_3$/TMS, δ (ppm)]:
8.88 (1H, s), 8.73 (1H, d), 7.54 (1H, d), 4.63 (2H, s)

Reference Example 48

Production of 5-bromo-4-hydroxy-6-trifluoromethylpyrimidine 77.5 g (945.0 mmoles) of anhydrous sodium acetate was added, at room temperature, to a solution of 49.2 g (300.0 mmoles) of 4-hydroxy-6-trifluoromethylpyrimidine dissolved in 600 ml of acetic acid. Thereto was gradually added 50.3 g (315 mmoles) of bromine at 45° C. The resulting mixture was stirred at the same temperature for 3 hours to give rise to a reaction. After confirmation of the completion of the reaction, the reaction mixture was subjected to vacuum distillation to remove the solvent contained therein. The residue was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was washed with n-hexane to obtain 38.9 g (yield: 53.4%) of 5-bromo-4-hydroxy-6-trifluoromethylpyrimidine.

Reference Example 49

Production of 5-bromo-4-chloro-6-trifluoromethylpyrimidine 24.3 g (100.0 mmoles) of 5-bromo-4-hydroxy-6-trifluoromethylpyrimidine was suspended in 18.5 g (120.0 mmoles) of phosphorus oxychloride. The mixture was stirred at 100° C. for 2 hours to give rise to a reaction. After confirmation of the completion of the reaction, the reaction mixture was poured into water gradually, followed by extraction with chloroform. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 21.5 g (yield: 82.4%) of 5-bromo-4-chloro-6-trifluoromethylpyrimidine.

Reference Example 50

Production of 5-bromo-4-methoxy-6-trifluoromethylpyrimidine 16.7 ml of sodium methoxide (a 28% methanol solution, 86.4 mmoles) was added, at room temperature, to a solution of 21.5 g (82.2 mmoles) of 5-bromo-4-chloro-6-trifluoromethylpyrimidine dissolved in 100 ml of methanol. The mixture was stirred to give rise to a reaction. After confirmation of the completion of the reaction, the reaction mixture was subjected to vacuum distillation to remove the solvent contained therein. The residue was poured into water, followed by extraction with chloroform. The resulting organic layer was washed with water and an aqueous sodium chloride solution in this order and then dried over anhydrous magnesium sulfate. The resulting solution was subjected to vacuum distillation to remove the solvent contained therein. The residue was washed with n-hexane to obtain 19.2 g (yield: 91.0%) of 5-bromo-4-methoxy-6-trifluoromethylpyrimidine.

Reference Example 51

Production of
5-bromo-4-ethoxy-6-trifluoromethylpyrimidine 0.94 g (13.77 mmoles) of sodium ethoxide was added, at room temperature, to a solution of 3.00 g (11.48 mmoles) of 5-bromo-4-chloro-6-trifluoromethylpyrimidine dissolved in 50 ml of ethanol. The mixture was stirred to give rise to a reaction. After confirmation of the completion of the reaction, the reaction mixture was subjected to vacuum distillation to remove the solvent contained therein. The residue was poured into water, followed by extraction with chloroform. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 2.44 g (yield: 82.9%) of 5-bromo-4-ethoxy-6-trifluoromethylpyrimidine.

Reference Example 52

Production of 4-methoxy-6-trifluoromethylpyrimidine-5-carboaldehyde 30.0 ml of n-butyllithium (a 1.6 moles/liter n-hexane solution, 48.0 mmoles) was gradually added, at −65 to −60° C., to a solution of 10.3 g (40.0 mmoles) of 5-bromo-4-methoxy-6-trifluoromethylpyrimidine dissolved in 100 ml of tetrahydrofuran. The mixture was stirred for 30 minutes. Thereto was added 3.6 g (48.0 mmoles) of ethyl formate at the same temperature. The resulting mixture was stirred at the same temperature for 3 hours to give rise to a reaction. The reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 1.3 g (yield: 15.8%) of 4-methoxy-6-trifluoromethylpyrimidine-5-carboaldehyde.

$^1$H-NMR [CDCl$_3$/TMS, δ (ppm)]:
10.41 (1H, q), 8.91 (1H, s), 4.18 (3H, s)

Reference Example 53

Production of 4-ethoxy-6-trifluoromethylpyrimidine-5-carboaldehyde

A solution of 5.76 g (21.3 mmoles) of 5-bromo-4-ethoxy-6-trifluoromethylpyrimidine dissolved in 250 ml of THF was cooled to −78° C. Thereto was dropwise added 22.6 ml of n-butyllithium (a 1.6 moles/liter n-hexane solution, 36.1 mmoles). The mixture was stirred for 40 minutes. Thereto was added 2.7 g (45.1 mmoles) of methyl formate. The resulting mixture was stirred for 1.5 hours to give rise to a reaction. After the completion of the reaction, an aqueous ammonium chloride solution was added. The mixture was extracted with diethyl ether. The resulting organic layer was washed with an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 3.82 g (yield: 81.6%) of 4-ethoxy-6-trifluoromethylpyrimidine-5-carboaldehyde.

$^1$H-NMR [CDCl$_3$/TMS, δ (ppm)]:
10.41 (1H, s), 8.95 (1H, s), 4.63 (2H, q), 1.48 (3H, t)

Reference Example 54

Production of (4-methoxy-6-trifluoromethylpyrimidin-5-yl)-methanol 0.24 g (6.3 mmoles) of sodium borohydride was gradually added, at room temperature, to a solution of 1.3 g (6.3 mmoles) of 4-methoxy-6-trifluoromethylpyrimidine-5-carboaldehyde dissolved in 30 ml of methanol. The mixture was stirred for 3 hours to give rise to a reaction. After confirmation of the completion of the reaction, the reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 0.42 g (yield: 32.1%) of (4-methoxy-6-trifluoromethylpyrimidin-5-yl)-methanol $^1$H-NMR [CDCl$_3$/TMS, δ (ppm)]:
8.93 (1H, s), 4.81 (2H, s), 4.13 (3H, s), 2.26 (1H, br)

Reference Example 55

Production of (4-ethoxy-6-trifluoromethylpyrimidin-5-yl)-methanol

A solution of 3.82 g (17.2 mmoles) of 4-ethoxy-6-trifluoromethylpyrimidine-5-carboaldehyde dissolved in 50 ml of methanol was added, with ice-cooling, to a solution of 1.7 g (45.7 mmoles) of sodium borohydride dissolved in 50 ml of methanol. The mixture was stirred at 0° C. for 1 hour to give rise to a reaction. After the completion of the reaction, the reaction mixture was poured into water, followed by extraction with ethyl acetate. The resulting organic layer was washed with an aqueous sodium chloride solution and then dried over anhydrous magnesium sulfate. The resulting solution was subjected to vacuum distillation to remove the solvent contained therein, to obtain 3.77 g (yield: 97.8%) of (4-ethoxy-6-trifluoromethylpyrimidin-5-yl)-methanol $^1$H-NMR [CDCl$_3$/TMS, δ (ppm)]:
8.80 (1H, s), 4.81 (2H, s), 4.59 (2H, q), 2.28 (1H, b), 1.48 (3H, t)

Reference Example 56

Production of 5-chloromethyl-4-methoxy-6-trifluoromethylpyrimidine 1.19 g (10.1 mmoles) of thionyl chloride was added, at room temperature, to a solution of 0.42 g (2.02 mmoles) of (4-methoxy-6-trifluoromethylpyrimidin-5-yl)-methanol. The mixture was stirred for 3 hours to give rise to a reaction. After confirmation of the completion of the reaction, the reaction mixture was subjected to vacuum distillation to remove the solvent contained therein, to obtain 0.45 g (yield: quantitative) of 5-chloromethyl-4-methoxy-6-trifluoromethylpyrimidine.

Reference Example 57

Production of
5-bromomethyl-4-ethoxy-6-trifluoromethylpyrimidine

A solution of 3.77 g (17.0 mmoles) of (4-ethoxy-6-trifluoromethylpyrimidin-5-yl)-methanol dissolved in 50 ml of diethyl ether was cooled to 0° C. Thereto was added 2.0 g (7.2 mmoles) of phosphorus tribromide. The mixture was stirred at room temperature for 1 hour. The resulting salt was dissolved using methanol. The resulting mixture was stirred for 1 hour to give rise to a reaction. The reaction mixture was poured into water, followed by extraction with diethyl ether. The resulting organic layer was washed with an aqueous sodium chloride solution and then dried over anhydrous magnesium sulfate. The resulting solution was subjected to vacuum distillation to remove the solvent contained therein, to obtain crude 5-bromomethyl-4-ethoxy-6-trifluoromethylpyrimidine.

$^1$H-NMR [CDCl$_3$/TMS, δ (ppm)]:
8.79 (1H, s), 4.61 (2H, q), 4.55 (2H, s), 1.49 (3H, t)

Reference Example 58

Production of 4-methoxy-6-trifluoromethylpyrimidine-5-carboaldehyde 30.0 ml (48.0 mmol) of n-butyllithium (1.6 mol/l n-hexane solution) was slowly added to 100 ml of tetrahydrofuran solution containing 10.3 g (40.0 mmol) of 5-bromo-4-methoxy-6-trifluoromethylpyrimidine at −65 to −60° C., and the resultant mixture was stirred at 30 minutes. Further, 3.6 g (48.0 mmol) of ethyl formate was added thereto at the same temperature, and the mixture was stirred for 3 hours at the same temperature. The resultant reaction solution was poured into water and was extracted with ethyl acetate. The organic phase thus obtained was washed with water and an aqueous sodium chloride solution in this order, and then dried over anhydrous magnesium sulfate. The resultant solution was subjected to vacuum distillation to remove the solvent contained therein. The residue was purified by silica gel column chromatography to obtain 1.3 g (yield: 15.8%) of 4-methoxy-6-trifluoromethylpyrimidine-5-carboaldehyde.

$^1$H-NMR [CDCl$_3$/TMS δ (ppm)] 10.41 (1H, q) 8.98 (1H, s), 4.18 (3H, s)

Reference Example 59

Production of
(2-chloro-4-methylpyridin-3-yl)methanol

A solution of 1.9 g (10.0 mmoles) of methyl 2-chloro-4-methylnicotinate dissolved in 5.0 ml of THF was gradually added, at −65 to −60° C., to a suspension of 0.4 g (10.0 mmoles) of lithium aluminum hydride in 30 ml of tetrahydrofuran. The mixture was stirred for 30 minutes and at −20° C. for 1 hour to give rise to a reaction. The reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein. The residue was purified by silica gel column chromatography to obtain 0.6 g (yield: 38.2%) of (2-chloro-4-methylpyridin-3-yl)methanol.

$^1$H-NMR [CDCl$_3$/TMS, δ (ppm)]:
8.19 (1H, d), 7.08 (1H, d), 4.85 (2H, s), 2.49 (3H, s)

Reference Example 60

Production of
3-acetyl-4-chloromethyl-2,5-dichlorothiophene 33 ml of titanium tetrachloride (a 2 moles/liter dichloromethane solution, 66.0 mmoles) was dropwise added, at 10° C. with ice-cooling, to a solution of 5.0 g (32.4 mmoles) of 3-acetyl-2,5-dichlorothiophene dissolved in 26 ml (323.0 mmoles) of chloromethyl methyl ether. The mixture was stirred at room temperature for 2 hours to give rise to a reaction. After the completion of the reaction, the reaction mixture was poured into ice water, followed by extraction with chloroform. The resulting organic layer was washed with sodium bicarbonate, water and an aqueous sodium chloride solution in this order and then dried over anhydrous magnesium sulfate. The resulting solution was subjected to vacuum distillation to remove the solvent contained therein. The residue was purified by silica gel column chromatography (developing solvent: hexane/ethyl acetate=9/1) to obtain 2.6 g (yield: 39.7%) of 3-acetyl-4-chloromethyl-2,5-dichlorothiophene as yellow crystals.

$^1$H-NMR [CDCl$_3$/TMS, δ (ppm)]:
4.70 (2H, s), 2.56 (3H, s), 2.54 (3H, s), 2.39 (3H, s)

Reference Example 61

Production of 3-bromo-2-bromomethylbenzofuran 2.7 g (15.3 mmoles) of N-bromosuccinimide and 0.4 g (2.7 mmoles) of azobisisobutyronitrile were added to a solution of 2.8 g (13.3 mmoles) of 3-bromo-2-methylbenzofuran dissolved in 30 ml of monochlorobenzene. The mixture was stirred at 80° C. for 30 minutes to give rise to a reaction. After confirmation of the disappearance of the raw materials, the reaction mixture was cooled to room temperature. The insolubles were removed by filtration. The filtrate was subjected to vacuum distillation to remove the solvent contained therein. The residue was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein, to obtain 3.0 g (yield: 79.0%) of 3-bromo-2-bromomethylbenzofuran.

Reference Example 62

Production of ethyl
1-difluoromethyl-1H-pyrazole-4-carboxylate 6.0 g (43.5 mmoles) of anhydrous potassium carbonate was added to a solution of 3.0 g (21.4 mmoles) of ethyl 1H-pyrazole-4-carboxylate dissolved in 100 ml of N,N-dimethylformamide. Thereinto was blown chlorodifluoromethane. The resulting mixture was stirred at 130 to 140° C. for 3 hours to give rise to a reaction. After confirmation of the completion of the reaction, the reaction mixture was poured into water, followed by extraction with ethyl acetate. The resulting organic layer was washed with water and an aqueous sodium chloride solution and then dried over anhydrous magnesium sulfate. The resulting solution was subjected to vacuum distillation to remove the solvent contained therein. The residue was purified by silica gel column chromatography (developing solvent: hexane-ethyl acetate mixed solvent) to obtain 1.67 g (yield: 41.0%) of ethyl 1-difluoromethyl-1H-pyrazole-4-carboxylate as a colorless transparent oily substance.

$^1$H-NMR [CDCl$_3$/TMS, δ (ppm)]:

8.32 (1H, s), 8.04 (1H, s), 7.20 (1H, t), 4.32 (2H, q), 1.37 (3H, t)

Now, Working Examples are illustrated below. In the Examples, "part" means "part by weight".

Formulation 1

Wettable Powder

5 Parts of compound No. 3-0002 and 40 parts of cyanazine were mixed with 0.5 part of polyoxyethylene octylphenyl ether, 0.5 part of a sodium salt of an alkylnaphthalenesulfonic acid-formalin condensate, 12 parts of diatomaceous earth and 42 parts of clay. The mixture was mixed and pulverized to obtain a wettable powder.

The amount of the herbicidal composition of the present invention varies depending on a mixing ratio, weather conditions, a form of formulation, an application time, an application method, an application place, a target weed, a target crop or the like, but is usually from 50 to 1500 g per hectare as a total amount of active ingredients. In a case of an emulsion, a wettable powder, a suspension or the like, a predetermined amount is diluted with water in an amount of from 100 to 1000 liters per hectare to be applied.

The effect of the herbicidal composition of the present invention is illustrated by the following Application Examples.

Application Example 1

Test for Herbicidal Effect by Upland Field Soil Treatment

An upland field soil was filled in a plastic pot of 11 cm each of length, width and depth. Seeds of corn, green foxtail (*Setaria viridis*) and common lambsquarters (*Chenopodium album* L.) were sowed, followed by covering with the same soil. The wettable powder produced in accordance with Formulation 1 was weighed so as to provide active ingredients in a predetermined amount, and was diluted with water and sprayed uniformly on the soil surface using a small sprayer, in an amount of 100 liters per 10 acres. Then, growing was made in a greenhouse, and the herbicidal effect of each wettable powder was examined at the 30th day from the treatment in accordance with the standard shown in Table 15. The results are shown in Tables 16 and 17.

TABLE 15

| Index | Herbicidal effect (extent of growth inhibition) or phytotoxicity |
|---|---|
| 10 | Herbicidal effect of growth inhibition or phytotoxicity of 100% |
| 9 | Herbicidal effect or phytotoxicity of from 90 to 99% |
| 8 | Herbicidal effect or phytotoxicity of from 80 to 89% |
| 7 | Herbicidal effect or phytotoxicity of from 70 to 79% |
| 6 | Herbicidal effect or phytotoxicity of from 60 to 69% |
| 5 | Herbicidal effect or phytotoxicity of from 50 to 59% |
| 4 | Herbicidal effect or phytotoxicity of from 40 to 49% |
| 3 | Herbicidal effect or phytotoxicity of from 30 to 39% |
| 2 | Herbicidal effect or phytotoxicity of from 20 to 29% |

TABLE 15-continued

| Index | Herbicidal effect (extent of growth inhibition) or phytotoxicity |
|---|---|
| 1 | Herbicidal effect or phytotoxicity of from 10 to 19% |
| 0 | Herbicidal effect or phytotoxicity of from 0 to 9% |

TABLE 16

| | | Herbicidal effect | | |
|---|---|---|---|---|
| Compound | Amounts of active ingredient (g a.i./ha) | Corn | Green foxtail (*Sataria viridis*) | Common lambsquarter (*Chenopodium album L.*) |
| 3-0002 | 32 | 0 | 5 | 2 |
| Cyanazine | 500 | 0 | 1 | 2 |
| 3-0002 + Cyanazine | 32 + 500 | 0 | 10 | 7 |
| 3-0004 | 32 | 0 | 3 | 2 |
| Cyanazine | 500 | 0 | 1 | 2 |
| 3-0004 + Cyanazine | 32 + 500 | 0 | 9 | 7 |
| 3-0005 | 32 | 0 | 2 | 2 |
| Cyanazine | 500 | 0 | 1 | 2 |
| 3-0005 + Cyanazine | 32 + 500 | 0 | 9 | 6 |
| 3-0010 | 16 | 0 | 2 | 2 |
| Cyanazine | 500 | 0 | 1 | 2 |
| 3-0010 + Cyanazine | 16 + 500 | 0 | 10 | 8 |
| 3-0011 | 16 | 0 | 3 | 2 |
| Cyanazine | 500 | 0 | 1 | 2 |
| 3-0011 + Cyanazine | 16 + 500 | 0 | 10 | 8 |
| 3-0012 | 16 | 0 | 2 | 1 |
| Cyanazine | 500 | 0 | 1 | 2 |
| 3-0012 + Cyanazine | 16 + 500 | 0 | 9 | 7 |
| 3-0013 | 16 | 0 | 2 | 2 |
| Cyanazine | 500 | 0 | 1 | 2 |
| 3-0013 + Cyanazine | 16 + 500 | 0 | 9 | 7 |
| 3-0014 | 32 | 0 | 2 | 2 |
| Cyanazine | 500 | 0 | 1 | 2 |
| 3-0014 + Cyanazine | 32 + 500 | 0 | 9 | 8 |
| 3-0015 | 32 | 0 | 3 | 3 |
| Cyanazine | 500 | 0 | 1 | 2 |
| 3-0015 + Cyanazine | 32 + 500 | 0 | 9 | 8 |
| 3-0016 | 16 | 0 | 3 | 3 |
| Cyanazine | 500 | 0 | 1 | 2 |
| 3-0016 + Cyanazine | 16 + 500 | 0 | 10 | 9 |
| 3-0017 | 16 | 0 | 3 | 3 |
| Cyanazine | 500 | 0 | 1 | 2 |
| 3-0017 + Cyanazine | 16 + 500 | 0 | 9 | 9 |
| 3-0018 | 16 | 0 | 3 | 3 |
| Cyanazine | 500 | 0 | 1 | 2 |
| 3-0018 + Cyanazine | 16 + 500 | 0 | 10 | 9 |
| 4-0001 | 32 | 0 | 2 | 1 |
| Cyanazine | 500 | 0 | 1 | 2 |
| 4-0001 + Cyanazine | 32 + 500 | 0 | 8 | 7 |

TABLE 17

| | | Herbicidal effect | | |
|---|---|---|---|---|
| Compound | Amounts of active ingredient (g a.i./ha) | Corn | Green foxtail (*Sataria viridis*) | Common lambsquarter (*Chenopodium album L.*) |
| 4-0002 | 32 | 0 | 3 | 2 |
| Cyanazine | 500 | 0 | 1 | 2 |
| 4-0002 + Cyanazine | 32 + 500 | 0 | 9 | 7 |
| 2-0001 | 32 | 0 | 2 | 1 |
| Cyanazine | 500 | 0 | 1 | 2 |
| 2-0001 + Cyanazine | 32 + 500 | 0 | 8 | 7 |
| 8-0001 | 16 | 0 | 2 | 1 |
| Cyanazine | 500 | 0 | 1 | 2 |
| 8-0001 + Cyanazine | 16 + 500 | 0 | 9 | 7 |
| 3-0039 | 16 | 0 | 3 | 3 |

TABLE 17-continued

| Compound | Amounts of active ingredient (g a.i./ha) | Herbicidal effect | | |
| --- | --- | --- | --- | --- |
| | | Corn | Green foxtail (Sataria viridis) | Common lambsquarter (Chenopodium album L.) |
| Cyanazine | 500 | 0 | 1 | 2 |
| 3-0039 + Cyanazine | 16 + 500 | 0 | 10 | 9 |
| 3-0188 | 16 | 0 | 3 | 2 |
| Cyanazine | 500 | 0 | 1 | 2 |
| 3-0188 + Cyanazine | 16 + 500 | 0 | 10 | 9 |
| 3-0190 | 16 | 0 | 3 | 1 |
| Cyanazine | 500 | 0 | 1 | 2 |
| 3-0190 + Cyanazine | 16 + 500 | 0 | 10 | 9 |

Application Example 2

Test for Herbicidal Effect by Upland Field Soil Treatment

An upland field soil was filled in a plastic pot of 11 cm each of length, width and depth. Seeds of corn and velvetleaf (*Abutilon theophrasti* Medic) were sowed, followed by covering with the same soil. The wettable powder produced in accordance with Formulation 1 was weighed so as to provide active ingredients in a predetermined amount, and was diluted with water and sprayed uniformly on the soil surface using a small sprayer, in an amount of 100 liters per 10 acres. Then, growing was made in a greenhouse, and the herbicidal effect of each wettable powder was examined at the 30th day from the treatment in accordance with the standard shown in Table 15. The results are shown in Table 18.

TABLE 18

| Compound | Amounts of active ingredient (g a.i./ha) | Corn | Velvetleaf (Abutilon theophrasti Medic) |
| --- | --- | --- | --- |
| Compound 3-188 | 16 | 0 | 2 |
| Compound 3-188 | 32 | 0 | 2 |
| Atrazine | 125 | 0 | 1 |
| Compound-3188 Atrazine | 16-125 | 0 | 7 |
| Compund 3-188 Atrazine | 32-125 | 0 | 10 |

INDUSTRIAL APPLICABILITY

The herbicidal composition of the present invention, which comprises a compound of the formula (I) and at least one compound selected from Group A, achieves not a simple total herbicidal activity but a synergistic herbicidal effect. Thus, the composition of the present invention achieves an excellent herbicidal effect at a small dose to various weeds growing on an upland field in a wide term range of from before germination to growing season, such as gramineous weeds including barnyardgrass (*Echinochloa crusglii* var. *crus-galli*), crabgrass (*Digitaria ciliaris*), green foxtail (*Setaria viridis*), annual bluegrass (*Poa annua*), johnsongrass (*Sorghum halepense* Pers.), blackgrass (*Alopecurus myosuroides*), wild oats (*Avena fatua*), and the like, broad leaf weeds including pale persicaria (*Polygonum lapathifolia*), slender amaranth (*Amaranthus viridis*), common lambsquarters (*Chenopodium album* L.), common chickweed (*Stellaria media* Villars), velvetleaf (*Abutilon theophrasti* Medic), prickly sida (*Sida spinosa* L.), Hemp sesbania (*Sesbania exaltata* Cory), common ragweed (*Ambrosia artemisiifolia*), morningglory, and the like, and annual and perennial sedge weeds including purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

Further, the composition of the present invention achieves an excellent herbicidal effect at a small dose to various weeds growing on a paddy field in a wide term range of from before germination to growing season, such as annual weeds including watergrass (*Echinochloa oryzicola*), smallflower umbrella plant (*Cyperus difformis*), konagi (*Monochoria vaginalis*), aze-na (*Lindernia procumbens*), and the like and perennial weeds including mizu-gayatsuri (*Cyperus serotinus*), kuroguwai (*Eleocharis kuroguwai*), inu-hotaru-i (*Scirpus juncoides*), and the like.

On the other hand, the herbicidal composition of the present invention is safe to aimed crop, particularly safe to rice, wheat, barley, corn, grain sorghum, soybeans, cotton, sugar beet, turf, fruit trees, and the like.

The invention claimed is:
1. A herbicidal composition which comprises
    i) an isoxazoline derivative represented by the following general formula (I) or a salt

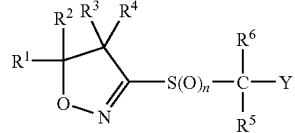

Formula (I)

wherein $R^1$ and $R^2$ are independently a hydrogen atom, a C1 to C10 alkyl group, a C3 to C8 cycloalkyl group or a C3 to C8 cycloalkyl C1 to C3 alkyl group; or $R^1$ and $R^2$ may be bonded to each other to form a C3 to C7 spiro ring together with the carbon atoms to which they bond;
$R^3$ and $R^4$ are independently a hydrogen atom, a C1 to C10 alkyl group or a C3 to C8 cycloalkyl group; or $R^3$ and $R^4$ may be bonded to each other to form a C3 to C7 spiro ring together with the carbon atoms to which they bond; or $R^1$, $R^2$, $R^3$ and $R^4$ may form a 5- to 8-membered ring together with the carbon atoms to which they bond;
$R^5$ and $R^6$ are independently a hydrogen atom or a C1 to C10 alkyl group;
Y is a 5- to 6-membered aromatic heterocyclic group or condensed aromatic heterocyclic group having one or more hetero atoms selected from a nitrogen atom, an oxygen atom and a sulfur atom; the heterocyclic group may be substituted with 0 to 6 same or different groups selected from the following substituent group α; when the heterocyclic group is substituted at the two adjacent positions with two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group, all selected from the substituent group α, the two groups may form, together with the atoms to which they bond, a 5- to 8-membered ring which may be substituted with 1 to 4 halogen atoms; the hetero atom of the heterocyclic group, when it is a nitrogen atom, may be oxidized to become N-oxide;

n is an integer of 0 to 2;

wherein said substituent group α is selected from the group consisting of hydroxyl group; thiol group; halogen atoms; C1 to C10 alkyl groups; C1 to C10 alkyl groups each mono-substituted with a group selected from the following substituent group β, C1 to C4 haloalkyl groups; C3 to C8 cycloalkyl groups; C1 to C10 alkoxy groups; C1 to C10 alkoxy groups each mono-substituted with a group selected from the following substituent group γ; C1 to C4 haloalkoxy groups; C3 to C8 cycloalkyloxy groups; C3 to C8 cycloalkyl C1 to C3 alkyloxy groups; C1 to C10 alkylthio groups; C1 to C10 alkylthio groups each mono-substituted with a group selected from the substituent group γ; C1 to C4 haloalkylthio groups; C2 to C6 alkenyl groups; C2 to C6 alkenyloxy groups; C2 to C6 alkynyl groups; C2 to C6 alkynyloxy groups; C1 to C10 alkylsulfinyl groups; C1 to C10 alkylsulfinyl groups each mono-substituted with a group selected from the substituent group γ; C1 to C10 alkylsulfonyl groups; C1 to C10 alkylsulfonyl groups each mono-substituted with a group selected from the substituent group γ; C1 to C4 haloalkylsulfinyl groups; C1 to C10 alkylsulfonyloxy groups each mono-substituted with a group selected from the substituent group γ; C1 to C4 haloalkylsulfonyl groups; C1 to C10 alkylsulfonyloxy groups; C1 to C4 haloalkylsulfonyloxy groups; optionally substituted phenyl group; optionally substituted phenoxy group; optionally substituted phenylthio group; optionally substituted aromatic heterocyclic groups; optionally substituted aromatic heterocyclic oxy groups; optionally substituted aromatic heterocyclic thio groups; optionally substituted phenylsulfinyl groups; optionally substituted phenylsulfonyl groups; optionally substituted aromatic heterocyclic sulfonyl groups; optionally substituted phenylsulfonyloxy groups; acyl groups; C1 to C4 haloalkylcarbonyl groups; optionally substituted benzylcarbonyl group; optionally substituted benzoyl group; carboxyl group; C1 to C10 alkoxycarbonyl groups; optionally substituted benzyloxycarbonyl group; optionally substituted phenoxycarbonyl group; cyano group; carbamoyl group (its nitrogen atom may be substituted with same or different groups selected from C1 to C10 alkyl groups and optionally substituted phenyl group); C1 to C6 acyloxy groups; C1 to C4 haloalkylcarbonyloxy groups; optionally substituted benzylcarbonyloxy group; optionally substituted benzoyloxy group; nitro group; and amino group (its nitrogen atom may be substituted with same or different groups selected from C1 to C10 alkyl groups, optionally substituted phenyl group, C1 to C6 acyl groups, C1 to C4 haloalkylcarbonyl groups, optionally substituted benzylcarbonyl group, optionally substituted benzoyl group, C1 to C10 alkylsulfonyl group, C1 to C4 haloalkylsulfonyl groups, optionally substituted benzylsulfonyl group, and optionally substituted phenylsulfonyl group);

wherein said substituent group β is selected from the group consisting of hydroxyl group; C3 to C8 cycloalkyl groups (which may be substituted with halogen atom or alkyl group); C1 to C10 alkoxy groups; C1 to C10 alkylthio groups; C1 to C10 alkylsulfonyl groups; C1 to C10 alkoxycarbonyl groups; C2 to C6 haloalkenyl groups; amino group (its nitrogen atom may be substituted with same or different groups selected from C1 to C10 alkyl groups, C1 to C6 acyl groups; C1 to C4 haloalkylcarbonyl groups, C1 to C10 alkylsulfonyl groups and C1 to C4 haloalkylsulfonyl groups); carbamoyl group (its nitrogen atom may be substituted with same or different C1 to C10 alkyl groups); C1 to C6 acyl groups; C1 to C4 haloalkylcarbonyl groups; C1 to C10 alkoxyimino groups; cyano group; optionally substituted phenyl group; and optionally substituted phenoxy group;

wherein said substituent group γ is selected from the group consisting of

C1 to C10 alkoxycarbonyl groups; optionally substituted phenyl group; optionally substituted aromatic heterocyclic groups; cyano group; and carbamoyl group (its nitrogen atom may be substituted with same or different C1 to C10 alkyl groups); and ii) at least one compound selected from the group consisting of atrazine, simazine, cyanazine, isoxaflutole, mesotrione, flumetsulam, imazethapyr, imazapyr, dicamba, clopyralid, prosulfuron, halosulfuron-methyl, rimsulfuron, bentazone, carfentrazone-ethyl, metribuzin, thifensulfuron-methyl, nicosulfuron, primisulfuron, cloransulam-methyl, glufosinate, glyphosate, glyphosate-trimesium, pendimethalin, linuron, prometryn, diflufenican, flumioxazin, and metolachlor, wherein the herbicidal composition has a synergistic herbicidal effect in comparison to the herbicidal effect of the isoxaline derivative (i) and the compound (ii) alone.

2. The herbicidal composition according to claim 1, wherein $R^1$ and $R^2$ may be the same or different and are each a methyl group or an ethyl group; and $R^3$, $R^4$, $R^5$ and $R^6$ are each a hydrogen atom.

3. The herbicidal composition according to claim 1, wherein Y is a 5- or 6-membered aromatic heterocyclic group having a hetero atom selected from a nitrogen atom, an oxygen atom and a sulfur atom.

4. The herbicidal composition according to claim 3, wherein Y is a thienyl group, a pyrazolyl group, an isoxazolyl group, an isothiazolyl group, a pyridyl group or a pyrimidinyl group.

5. The herbicidal composition according to claim 4, wherein Y is a thiophen-3-yl group, a pyrazol-4-yl group, a pyrazol-5-yl group, an isoxazol-4-yl group, an isothiazol-4-yl group, a pyridyn-3-yl group or a pyrimidin-5-yl group.

6. The herbicidal composition according to claim 5, wherein Y is a thiophen-3-yl group and the thiophene ring is substituted with the substituent group α at the 2- and 4-positions.

7. The herbicidal composition according to claim 5, wherein Y is a pyrazol-4-yl group and the pyrazole ring is substituted at the 3- and 5-positions with the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (its nitrogen atom may be substituted with same or different groups selected from C1 to C10 alkyl groups and optionally substituted phenyl group), or an amino group (its nitrogen atom may be substituted with same or different groups selected from C1 to C10 alkyl groups, an optionally substituted phenyl group, acyl groups, C1 to C4 haloalkylcarbonyl groups, an optionally substituted benzylcarbonyl group, an optionally substituted benzoyl group, C1 to C10 alkylsulfonyl groups, C1 to C4 haloalkylsulfonyl groups, an optionally substituted benzylsulfonyl group and an optionally substituted phenylsulfonyl group).

8. The herbicidal composition according to claim 5, wherein Y is a pyrazol-5-yl group and the pyrazole ring is substituted at the 4-position with the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (its nitrogen atom may be substituted with same or different groups selected from C1 to C10 alkyl groups and an optionally substituted phenyl group), or an amino group (its nitrogen atom may be substituted with same or different groups selected from C1 to C10 alkyl groups, an optionally substituted phenyl group, acyl groups, C1 to C4 haloalkylcarbonyl groups, an optionally substituted benzylcarbonyl group, an optionally substituted benzoyl group, C1 to C10 alkylsulfonyl groups, C1 to C4 haloalkylsulfonyl groups, an optionally substituted benzylsulfonyl group and an optionally substituted phenylsulfonyl group).

9. The herbicidal composition according to claim 5, wherein Y is an isoxazol-4-yl group and the isoxazole ring is substituted with the substituent group α at the 3- and 5-positions.

10. The herbicidal composition according to claim 5, wherein Y is an isothiazol-4-yl group and the isothiazole ring is substituted with the substituent group α at the 3- and 5-positions.

11. The herbicidal composition according to claim 5, wherein Y is a pyridin-3-yl group and the pyridine ring is substituted with the substituent group α at the 2- and 4-positions.

12. The herbicidal composition according to claim 5, wherein Y is a pyrimidin-5-yl group and the pyrimidine ring is substituted with the substituent group α at the 4- and 6-positions.

13. The herbicidal composition according to claim 1, wherein n is an integer of 2.

14. The herbicidal composition according to claim 1, wherein the compound ii) is at least one compound selected from the group consisting of atrazine, cyanazine, simazine and prometryn.

15. The herbicidal composition according to claim 1, wherein the compound ii) is at least one compound selected from the group consisting of glyphosate, glufosinate, linuron and flumetsulam.

16. A herbicidal composition which comprises i) the isoxazoline derivative or a salt thereof is a compound as defined in claim 7 and the compound ii) is at least one compound selected from the group consisting of atrazine, cyanazine, simazine, prometryn, glyphosate, glufosinate, linuron, flumetsulam, metribuzin, isoxaflutole, mesotrione, diflufenican, pendimethalin and flumioxazin.

17. A herbicidal composition which comprises i) the isoxazoline derivative or a salt thereof is a compound as defined in claim 7 and the compound ii) is at least one compound selected from the group consisting of atrazine, cyanazine, simazine and prometryn.

18. A herbicidal composition which comprises i) the isoxazoline derivative or a salt thereof is a compound as defined in claim 7 and the compound ii) is at least one compound selected from the group consisting of glyphosate, glufosinate, linuron and flumetsulam.

19. The herbicidal composition according to claim 1, wherein the compound ii) is comprised in an amount of from 0.001 to 100 parts by weight to 1 part by weight of i) an isoxazoline derivative represented by the Formula (I) or a salt thereof.

20. The herbicidal composition according to claim 1, which is used as an agrochemical product comprising i) an isoxazoline derivative of the Formula (I) or a salt thereof and the compound ii) in a total amount of from 0.5 to 90 wt %.

21. The herbicidal composition according to claim 1, wherein, when applied to soil, the herbicidal composition has a greater herbicidal effect than the cumulative herbicidal effect of the isoxaline derivative (i) and the compound (ii) alone.

22. The herbicidal composition according to claim 17, wherein, when applied to soil, the herbicidal composition has a greater herbicidal effect than the cumulative herbicidal effect of the isoxaline derivative (i) and the compound (ii) alone.

23. The herbicidal composition according to claim 18, wherein, when applied to soil, the herbicidal composition has a greater herbicidal effect than the cumulative herbicidal effect of the isoxaline derivative (i) and the compound (ii) alone.

24. The herbicidal composition according to claim 1, wherein the compound (ii) is at least one of cyanazine and atrazine, and when applied to soil the herbicidal composition has a greater herbicidal effect than the cumulative herbicidal effect of the isoxaline derivative (i) and the compound (ii) alone.

25. The herbicidal composition according to claim 7, wherein the composition comprises atrazine and, when applied to soil, the herbicidal composition has a greater herbicidal effect than the cumulative herbicidal effect of the isoxaline derivative (i) and the compound (ii) alone.

26. An herbicidal composition, comprising:
i) the following compound of formula:

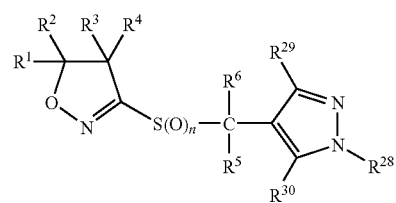

wherein $R^1$ and $R^2$ are methyl; $R^3$ and $R^4$ are hydrogen atoms; n is 2; $R^5$ and $R^6$ are hydrogen atoms; $R^{28}$ is methyl; $R^{29}$ is $CF_3$; and $R^{30}$ is difluoromethoxy; and at least one herbicidally active compound selected from the group consisting of thifensulfuron-methyl, isoxaflutole, flumetsulam, glyphosate, pendimethalin, diflufenican, flumioxazin, linuron, and prometryn, wherein the herbicidal composition has a synergistic herbicidal effect in comparison to the herbicidal effect of the isoxaline derivative (i) and the herbicidally active compound (ii) alone.

27. The herbicidal composition of claim 26, wherein the component i) is present in an amount of 5 parts by weight and component ii) is present in an amount of 40 parts by weight based on the total weight of the composition.

28. The herbicidal composition of claim 27, further comprising:

0.5 part of polyoxyethylene octylphenyl ether, 0.5 part of a sodium salt of an alkylnaphthalenesulfonic acid-formalin condensate, 12 parts of diatomaceous earth and 42 parts of clay.

* * * * *